United States Patent [19]

McDonald et al.

[11] Patent Number: 5,962,419
[45] Date of Patent: Oct. 5, 1999

[54] PEPTIDE AND PEPTIDE ANALOG PROTEASE INHIBITORS

[75] Inventors: Ian Alexander McDonald; Elisabeth Albrecht; Benito Munoz; Blake Alan Rowe; Robert Steven Siegel, all of San Diego; Steven Lee Wagner, Del Mar, all of Calif.

[73] Assignee: SIBIA Neurosciences, Inc., La Jolla, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/442,514

[22] Filed: May 17, 1995

Related U.S. Application Data

[63] Continuation of application No. 08/369,422, Jan. 6, 1995, Pat. No. 5,804,560.

[51] Int. Cl.[6] .................................................. A61K 38/05
[52] U.S. Cl. .............................. 514/19; 514/18; 530/331; 562/575
[58] Field of Search ........................................ 514/18, 19

[56] References Cited

U.S. PATENT DOCUMENTS

| | | |
|---|---|---|
| 4,044,126 | 8/1977 | Cook et al. .............................. 424/243 |
| 4,364,923 | 12/1982 | Cook et al. ................................ 424/46 |
| 4,414,209 | 11/1983 | Cook et al. .............................. 424/243 |
| 4,472,305 | 9/1984 | Hansen et al. .................... 260/112.5 R |
| 4,666,829 | 5/1987 | Glenner et al. ............................ 435/6 |
| 4,701,407 | 10/1987 | Appel ........................................ 435/4 |
| 4,840,935 | 6/1989 | Wagnon et al. ........................... 514/18 |
| 4,845,079 | 7/1989 | Luly et al. ................................ 514/18 |
| 5,015,570 | 5/1991 | Scangos et al. ............................ 435/6 |
| 5,034,376 | 7/1991 | Hoover ..................................... 514/18 |
| 5,039,511 | 8/1991 | Quay et al. ............................... 424/1.1 |
| 5,081,284 | 1/1992 | Higuchi et al. .......................... 560/159 |
| 5,164,371 | 11/1992 | Edwards et al. .......................... 514/18 |
| 5,200,339 | 4/1993 | Abraham ................................. 435/212 |
| 5,213,962 | 5/1993 | van Nostrandt et al. ................ 435/7.1 |
| 5,218,100 | 6/1993 | Muller-Hill et al. .................. 536/23.5 |
| 5,221,665 | 6/1993 | Skiles ....................................... 514/18 |
| 5,223,633 | 6/1993 | Hoppe et al. ............................. 556/95 |
| 5,231,000 | 7/1993 | Majocha et al. ........................ 435/701 |
| 5,232,928 | 8/1993 | Skiles ..................................... 514/291 |
| 5,242,932 | 9/1993 | Gandy et al. ............................ 514/313 |
| 5,270,165 | 12/1993 | van Nostrandt et al. ................ 435/7.1 |
| 5,284,828 | 2/1994 | Hemmi et al. ............................ 514/18 |
| 5,348,963 | 9/1994 | Gandy et al. ............................ 514/313 |
| 5,374,623 | 12/1994 | Zimmerman et al. .................... 514/17 |
| 5,427,931 | 6/1995 | Van Nostrand et al. ............. 435/70.2 |
| 5,430,022 | 7/1995 | Hemmi et al. ............................ 514/18 |
| 5,436,229 | 7/1995 | Ruterbories et al. ..................... 514/18 |
| 5,441,870 | 8/1995 | Seubert et al. .......................... 435/7.1 |
| 5,470,833 | 11/1995 | Ishikawa et al. ......................... 514/18 |
| 5,496,928 | 3/1996 | Ishikawa et al. ........................ 530/331 |
| 5,508,167 | 4/1996 | Roses et al. ............................... 435/6 |
| 5,538,845 | 7/1996 | Knops et al. .............................. 435/6 |
| 5,547,841 | 8/1996 | Marrotta et al. ........................... 435/6 |
| 5,578,451 | 11/1996 | Nishimoto ............................... 435/7.1 |
| 5,593,846 | 1/1997 | Schenk et al. ........................... 435/7.9 |
| 5,604,102 | 2/1997 | McConlogue et al. .................. 435/7.1 |
| 5,605,811 | 2/1997 | Seubert et al. ............................ 435/29 |
| 5,612,486 | 3/1997 | McConlogue et al. ..................... 800/2 |
| 5,631,168 | 5/1997 | Growdon et al. ......................... 436/71 |
| 5,643,726 | 7/1997 | Tanzi et al. ................................. 435/6 |
| 5,652,092 | 7/1997 | Vitek et al. ................................. 435/4 |
| 5,656,477 | 8/1997 | Vitek et al. .............................. 435/325 |
| 5,703,209 | 12/1997 | Vitek et al. .............................. 530/350 |
| 5,766,846 | 6/1998 | Schlossmacher et al. .................. 435/6 |
| 5,797,853 | 8/1998 | Musha et al. ............................ 600/544 |

FOREIGN PATENT DOCUMENTS

| | | |
|---|---|---|
| 1161431 | 1/1984 | Canada . |
| 0068551 | 6/1982 | European Pat. Off. .................. 103/50 |
| 0252057 | 6/1987 | European Pat. Off. . |
| 0266950 | 10/1987 | European Pat. Off. .......... C07K 5/02 |
| 0285159 | 3/1988 | European Pat. Off. . |
| 0287909 | 4/1988 | European Pat. Off. . |
| 0363284 | 10/1989 | European Pat. Off. . |
| 363635 | 2/1990 | European Pat. Off. . |
| 0364344 | 4/1990 | European Pat. Off. . |
| 0391714 | 4/1990 | European Pat. Off. . |
| 0393457 | 4/1990 | European Pat. Off. . |
| 0410411 | 1/1991 | European Pat. Off. . |
| 0444856 | 2/1991 | European Pat. Off. . |
| 0457195 | 5/1991 | European Pat. Off. .......... C07K 5/02 |
| 0460679 | 6/1991 | European Pat. Off. .......... C07K 5/02 |
| 0504938 | 3/1992 | European Pat. Off. . |
| 0528629 | 8/1992 | European Pat. Off. .......... C07K 5/06 |
| 543310A2 | 11/1992 | European Pat. Off. ................. 271/20 |
| 543310A3 | 11/1992 | European Pat. Off. ................. 271/20 |
| 0564946 | 3/1993 | European Pat. Off. . |
| 0569777 | 4/1993 | European Pat. Off. .......... C12Q 1/37 |
| 578978A1 | 6/1993 | European Pat. Off. ....................... 5/6 |
| 0580161 | 7/1993 | European Pat. Off. . |
| 0582143 | 7/1993 | European Pat. Off. . |
| 615969A1 | 3/1994 | European Pat. Off. ................. 271/22 |
| 0613007 | 8/1994 | European Pat. Off. . |
| 0623592 | 11/1994 | European Pat. Off. . |
| 0623627 | 11/1994 | European Pat. Off. . |
| 0627400 | 12/1994 | European Pat. Off. . |
| 0644198 | 3/1995 | European Pat. Off. . |
| 0652009 | 5/1995 | European Pat. Off. . |
| 6345722 | 12/1994 | Japan . |
| 8803951 | 11/1987 | WIPO . |
| 9005138 | 11/1989 | WIPO . |
| 9012871 | 4/1990 | WIPO . |
| 9015331 | 5/1990 | WIPO . |
| 9104339 | 9/1990 | WIPO . |
| 9115773 | 4/1991 | WIPO . |
| 9209699 | 11/1991 | WIPO . |
| 9200521 | 1/1992 | WIPO . |
| 9214696 | 2/1992 | WIPO ..................................... 271/22 |
| 9203542 | 3/1992 | WIPO . |
| 9207068 | 4/1992 | WIPO . |
| 9307296 | 10/1992 | WIPO . |
| 9220357 | 11/1992 | WIPO . |
| 9310459 | 11/1992 | WIPO . |
| 9316101 | 1/1993 | WIPO . |
| 9321526 | 3/1993 | WIPO . |
| 9513084 | 11/1993 | WIPO . |
| 9400095 | 1/1994 | WIPO . |
| 9401772 | 1/1994 | WIPO . |
| 9409370 | 4/1994 | WIPO . |
| 9413798 | 6/1994 | WIPO . |
| 9421625 | 9/1994 | WIPO . |
| 9423756 | 10/1994 | WIPO . |
| 9500535 | 1/1995 | WIPO . |
| 9500537 | 1/1995 | WIPO . |
| 9505177 | 2/1995 | WIPO . |

| | | |
|---|---|---|
| 9505192 | 2/1995 | WIPO . |
| 9507079 | 3/1995 | WIPO . |
| 9509838 | 4/1995 | WIPO ......................... C07C 271/22 |
| 9521855 | 8/1995 | WIPO ............................ C07K 5/062 |
| 9524914 | 9/1995 | WIPO ............................ A61K 38/00 |
| 9839967 | 9/1998 | WIPO . |

OTHER PUBLICATIONS

Cooper, et al., "X–ray Studies of Aspartic Proteinase–Statine Inhibitor Complexes," *Biochemistry*, 28:8596–8603 (1989).

O'Donnell, et al., "Synthesis of β,γ–Unsaturated Amino Acid Derivatives by Alkyne Carbometalation–Palladium Catalyzed Coupling with 2–Aza–π–Allyl Palladium Complexes," *Tetrahedron Letters*, 35(50):9383–9386 (1994).

Ocain and Rich, "α–keto amide inhibitors of aminopeptidases," *J. Med. Chem.*, 35:451–456 (1992).

Van Nostrandt, et al., "Immunopurification and protease inhibitory properties of protease nexin–2/amyloid β–protein precursor," *J. Biol. Chem.*, 265(17): 9591–9594 (1990).

Higgins, et al., "Early Alzheimer disease–like histopathology increases in frequency with age in mice transgenic for β–APP751," *Proc. Natl. Acad. Sci. USA*, 92:4402–4406 (1995).

Borman, "Diverse strategies emerge for diagnosing Alzheimer's disease", *C&EN*, pp. 33–34 (1996).

de Lustig et al., "Peripheral markers and diagnostics criteria in Alzheimer's disease: Critical evaluations", *Rev. Neurosci.* 5:213–225 (1994).

Dresse et al., "Towards a pharmacological approach of alzheimer's disease based on the molecular biology of the amyloid precursor protein (APP)", *Life Sci* 35(25/26):2179–2187 (1994).

English language Abstract of Japanese Patent No. 6345722 (Dialog(R)File 351:Derwent WPI Accession No.: 95–070275).

Kazmaier, "Introduction of Allylic Side Chains onto Peptides by Pd(O)–Catalyzed "Ester Enolate Claisen Rearrangement"" *J. Org. Chem.*59:6667 (1994).

Price et al., "Alzheimer disease and the prion disorders amyloid β–protein and prion protein amyloidoses", *Proc. Natl. Acad. Sci. USA* 90:6381–6384 (1993).

Selkoe, "Normal and abnormal biology of the β–amyloid precursor protein", *Annu. Rev. Neurosci.* 17:489–517 (1994).

Sham et al., "Highly potent and specific inhibitors of human renin", *FEB* 220(2):299–301 (1987).

Sisodia et al., "Cellular and molecular biology of alzheimer's disease and animal models", *Neurodegenerative Diseases* 5(1):59–68 (1995).

Smith and Anderson, "The molecular pathology of Alzheimer's disease: are we any closer to understanding the neurodegenerative process?" *Neuropathol. Appl. Neurobiol.* 20(4):322–338 (1994).

Almkvist et al., Cerebrospinal fluid levels of α–secretase––cleaved soluble amyloid precursor protein mirror cognition in a swedish family with Alzheimer disease and a Gene mutation, *Arch. Neurol.* 54:641–644 (1997).

Siman et al., Proteolytic processing of β–Amyloid precursor by calpain I, *J. Neurosci.* 10(7):2400–2411 (1990).

Anderson et al, "Differential induction of immediate early gene proteins in cultured neurons by β–amyloid (Aβ): Association of c–jun with Aβ–induced apoptosis," *J. Neurochem.* 65 (4):1487–1498 (1995).

Asami–Odaka et al., "Long amyloid β–protein secreted from wild–type human neuroblastoma IMR–32 cells," *Biochemistry* 34:10272–10278 (1995).

Barry et al., "Protection against mycoplasma infection using expression–library immunization," *Nature* 377:632–635 (1995).

Checler, "Processing of the β–amyloid precursor protein and its regulation in Alzheimer's disease," *J. Neurochem.* 65(4):1431–1444 (1995).

Le et al, "β–amyloid$_{1-40}$ increases expression of β–amyloid precursor protein in neuronal hybrid cells," *J. Neurochem.* 65(5):2373–2376 (1995).

Mahdi et al., "Protease nexin/amyloid β–protein precursor inhibits factor Xa in the prothrombinase complex," *J. Biol. Chem.* 270(40):23468–23474 (1995).

Mark et al., "Amyloid β–peptide impairs ion–motive ATPase activities: Evidence for a role in loss of neuronal $Ca^{2+}$ homeostasis and cell death," *J. Neurosci.* 15(9):6239–6249 (1995).

Moss et al., "Peptidometric inhibitors of herpes simplex virus ribonucleotide reductase: A new class of antiviral agents," *J. Med. Chem.* 38:3617–3623 (1995).

Pike et al., "Amino–terminal deletions enhance aggregation of β–amyloid peptides in vitro," *J. Biol. Chem.* 270(41):23895–23898 (1995).

Thaisrivongs et al., "Structure–based design of novel HIV protease inhibitors: Carboxamide–containing 4–hydroxycoumarins and 4–hydroxy–2–pyrones as potent nonpeptidic inhibitors," *J. Med. Chem.* 38:3624–3637 (1995).

Wang et al., "A novel matrix attachment region DNA binding motif identified using a random phage peptide library," *J. Biol. Chem.* 270(40):23239–23242 (1995).

Xu et al., "Regulated formation of Golgi secretory vesicles containing Alzheimer's β–amyloid precursor protein," *J. Biol. Chem.* 270(40):23243–23245 (1995).

Yoshimoto et al., "NACP, the precursor protein of the non–amyloid β/A4 protein (Aβ) component of Alzheimer's disease amyloid, binds Aβ and stimulates Aβ aggregation," *Proc. Natl. Acad. Sci. USA* 92:9141–9145 (1995).

Angelastro, et al., "Inhibition of Human Neutrophil Elastase with Peptidyl Electrophilic Ketones," *J. Med. Chem.*, 37:4538–4554 (1994).

Angliker, et al., "Inactivation of calpain by peptidyl fluoromethyl ketones," *J. Med. Chem.*, 35:216–220 (1992).

Arnér, et al., "1–Chloro–2,4–dinitrobenzene is an Irreversible Inhibitor of Human Thioredoxin Reductase," *J. Biol. Chem.*, 270(8):3479–3482 (1995).

Bodanszky and Bodanszky, "I. Protecting Groups 5. The tert.Butyloxycarbonyl (Boc) Group," *The Practice of Peptide Synthesis*, Springer–Verlag, pp. 18–20 (1984).

Bradbury, et al., "1,2,4–Triazolo[4,3–α]pyrazine Derivatives with Human Renin Inhibitory Activity," *J. Med. Chem.*, 33:2335–2342 (1990).

Breaux and Bender, "The binding of specific and non–specific aldehyde substrate analogs to α–chymotrypsin," *FEBS Letters*, 56(1):81–84 (1975).

Buxbaum, et al., "Cholinergic agonists and interleukin 1 regulate processing and secretion of the Alzheimer β/A4 amyloid protein precursor," *Proc. Natl. Acad. Sci. USA*, 89:10075–10078 (1992).

Cai, et al., "Release of excess amyloid β protein from a mutant amyloid β protein precursor," *Science*, 259:514–516 (1993).

Caporaso, et al., "Chloroquine inhibits intracellular degradation but not secretion of Alzheimer β/A4 amyloid precursor protein," *Proc. Natl. Acad. Sci. USA*, 89:2252–2256 (1992).

Citron, et al., "Mutation of the β–amyloid precursor protein in familial Alzheimer's disease increases β–protein production," *Nature*, 360:672–674 (1992).

Cooper, et al., "X-ray Crystallographic Analysis of Inhibition of Endothiapepsin by Cyclohexyl Renin Inhibitors," *Biochemistry*, 31:8142–8150 (1992).

Crawford, et al., "The design of peptidyldiazomethane inhibitors to distinguish between the cysteine proteinases calpain II, cathepsin L and cathepsin B," *J. Biochem.*, 253:751–758 (1988).

Crawford, "Protein and peptide inhibitors of calpains," *Intracellular Calcium–Dependent Proteolysis*, Chapter 5, pp. 75–89.

Davis, et al., "A double–blind, placebo–controlled multicenter study of tacrine for Alzheimer's disease," *New England J. of Med.*, 327(18):1253–1259 (1992).

De Strooper, et al., "Basolateral Secretion of Amyloid Precursor Protein in Madin–Darby Canine Kidney Cells is Disturbed by Alterations of Intracellular pH and by Introducing a Mutation Associated with Familial Alzheimer's Disease," *J. Biol. Chem.*, 270(8):4058–4065 (1995).

Dess and Martin, "Readily accessible 12–I–5$^1$ oxidant for the conversion of primary and secondary alcohols to aldehydes and ketones," *J. Org. Chem.*, 48:4155–4156 (1983).

Dolle, et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme–Peptide Inhibitor Binding," *J. Med. Chem.*, 37(23):3863–3866 (1994).

Esch, et al., "Cleavage of amyloid β peptide during constitutive processing of its precursor," *Science*, 24:1122–1124 (1990).

Farlow, et al., "Low cerebrospinal–fluid concentrations of soluble amyloid β–protein precursor in hereditary Alzheimer's disease," *Lancet*, 340:453–454 (1992).

Figueiredo–Pereira, et al., "Comparison of the effect of calpain inhibitors on two extralysosomal proteinases: The multicatalytic proteinase complex and m–calpain," *J. Neurochemistry*, 62(5):1989–1994 (1994).

Figueiredo–Pereira, et al., "A new inhibitor of the chymotrypsin–like activity of the multicatalytic proteinase complex (20S proteasome) induces accumulation of ubiquitin–protein conjugates in a neuronal cell," *J. Neurochemistry*, 63(4):1578–1581 (1994).

Folstein, et al., "Mini–mental state"—"A practical method for grading the cognitive state of patients for the clinician," *J. Psychiat. Res.*, 12:189–198 (1975).

Francis, et al., "Soluble β–amyloid precursor protein and pyramidal neuron loss," *Lancet*, 341:431 (1993).

Gisin, "The preparation of Merrifield–resins through total esterification with cesium salts," *Helvetica Chimica Acta*, 56(5):1476–1482 (1973).

Glenner and Wong, "Alzheimer's disease: Initial report of the purification and characterization of a novel cerebrovascular amyloid protein," *Biochem. and Biophys. Res. Comm.*, 120(3):885–890 (1984).

Grubb, et al., "Abnormal metabolism of γ–trace alkaline microprotein—The basic defect in hereditary cerebral hemorrhage with amyloidosis," *N. England J. of Med.*, 311(24):1547–1549 (1984).

Haas, et al., "Targeting of cell–surface β–amyloid precursor protein to lysosomes: alternative processing into amyloid––bearing fragments," *Nature*, 357:500–503 (1992).

Hardy, "The genetics of Alzheimer's disease," *Neurosci. Facts*, 3:65 (1992).

Hardy and Higgins, "Alzheimer's disease: The amyloid cascade hypothesis," *Science*, 256:184–185 (1992).

Harris, et al., "Characterization of a Continuous Fluorogenic Assay for Calpain L. Kinetic Evaluation of Peptide Aldehydes, Halomethyl Ketones and (Acyloxy)Methyl Ketones as Inhibitors of the Enzyme," *Bioorg. & Med. Chem. Lett.*, 5(4):393–398 (1995).

Henrikkson, et al., "Analysis and quantitation of the β–amyloid precursor protein in the cerebrospinal fluid of Alzheimer's disease patients with a monoclonal antibody–based immunoassay," *J. Neurochem.*, 56(3):1037–1042 (1991).

Imperiali and Abeles, "Inhibition of Serine Proteases by Peptidyl Fluoromethyl Ketones," *Biochemistry*, 25:3760–3767 (1985).

Inoue, et al., "Inhibition of degradation of 3–hydroxy–3–methylglutaryl–coenzyme A reductase in Vivo by cysteine protease inhibitors," *J. Biol. Chem.*, 266(20):13311–13317 (1991).

Inoue, et al., "Cellular detoxification of tripeptidyl aldehydes by an aldo–keto reductase," *J. Biol. Chem.*, 268(8):5894–5898 (1993).

Ito, et al., "Synthetic study of peptide aldehydes," *Chem. Pharm. Bull.*, 23(12):3106–3113 (1975).

Ito, et al., "Peptide aldehydes inhibiting chymotrypsin," *Biochem. and Biophys. Res. Comm.*, 49(2):343–349 (1972).

Iwanowicz, et al., "Retro–binding tripeptide thrombin active–site inhibitors: Discovery, synthesis, and molecular modeling," *J. Med. Chem.*, 37(14):2122–2124 (1994).

Kaiser, et al., "Color test for detection of free terminal amino groups in the solid–phase synthesis of peptides," *Analyt. Biochem.*, 34:595–598 (1970).

Kapoor, "Recent trends in the synthesis of linear peptides," *J. Pharm. Sci.*, 59(1):1–27 (1970).

Kowall, et al., "An in vivo model for the neurodegenerative effects of β amyloid and protection by substance P," *Proc. Natl. Acad. Sci. USA*, 88:7247–7251 (1991).

Krishnamurti, et al., "Preparation of Trifluoromethyl and Other Perfluoroalkyl Compounds with (Perfluoroalkyl)trimethylsilanes," *J. Org. Chem.*, 56:984–989 (1991).

Lai, et al., "Characterization of Sorting Signals in the β–Amyloid Precursor Protein Cytoplasmic Domain," *J. Biol. Chem.*, 270(8):3565–3573 (1995).

Lamb, et al., Introduction and expression of the 400 kilobase precursor amyloid protein gene in transgenic mice *Nature Genet.*, 5:22–29 (1993).

Lannfelt, et al., "Low frequency of the APP 670/671 mutation in familial Alzheimer's disease in Sweden," *Neurosci. Letters*, 153:85–87 (1993).

Lannfelt, et al., "Amyloid precursor protein mutation causes Alzheimer's disease in a Swedish family," *Neurosci. Letters*, 168:254–256 (1994).

Lehninger, "The amino acid building blocks of proteins," *Biochemistry (2d Ed.) The Molecular Basis of Cell Structure and Function*, pp. 71–92.

Levy, et al., Mutation of the Alzheimer's disease amyloid gene in hereditary cerebral hemorrhage, Dutch type, *Science*, 248:1124–1126 (1990).

Linderman, et al., "Unique Inhibition of a Serine Esterase," *Tetrahedron Letters*, 34(20):3227–3230 (1993).

Marx, "Major setback for Alzheimer's models," *Science*, 25:1200–1202 (1992).

Matsumoto and Fujiwara, "Abnormal and deficient processing of β–amyloid precursor protein in familial Alzheimer's disease lymphoblastoid cells," *Biochem. and Biophys. Res. Comm.*, 175(2):361–365 (1991).

McKhann, et al., "Clinical diagnosis of Alzheimer's disease: Report of the NINCDS–ADRDA work group under the auspices of Department of Health and Human Services Task Force on Alzheimer's Disease," *Neurology*, 34:939–944 (1984).

Mjalli, et al., "Activated Ketones as Potent Reversible Inhibitors of Interleukin–1β Converting Enzyme," *Bioorg. & Med. Chem. Lett.*, 4(16):1965–1968 (1994).

Mullan, et al., "A pathogenic mutation for probable Alzheimer's disease in the APP gene at the N–terminus of β–amyloid," *Nature Genetics*, 1:345–347 (1992).

Murrell, et al., "A mutation in the amyloid precursor protein associated with hereditary Alzheimer's disease," *Science*, 254:97–99 (1991).

Oleksyszyn and Powers, "Irreversible Inhibition of Serine Proteases by Peptidyl Derivatives of α–Aminoalkylphosphonate Diphenyl Esters," *Biochem. and Biophys. Res. Comm.*, 161(1):143–149 (1989).

Oleksyszyn and Powers, "Irreversible Inhibition of Serine Proteases by Peptide Derivatives of (α–Aminoalkyl)phosphonate Diphenyl Esters," *Biochemistry*, 30:485–493 (1991).

Orlowski, et al., "Evidence for the presence of five distinct proteolytic components in the pituitary multicatalytic proteinase complex. Properties of two components cleaving bonds on the carboxyl side of branched chain and small neutral amino acids," *Biochemistry*, 32(6):1563–1572 (1993).

Palmert, et al., "Soluble derivatives of the β amyloid protein precursor in cerebrospinal fluid: Alterations in normal aging and in Alzheimer's disease," *Neurology*, 40:1028–1034 (1990).

Patel, et al., "Activated Ketone Based Inhibitors of Human Renin," *J. Med. Chem.*, 36(17):2431–2447 (1993).

Patel, et al., "Peptidic trifluoromethyl alcohols and ketones: A general synthesis and application as renin inhibitors," *Tetrahedron Letters*, 29(37):4665–4668 (1988).

Pearson and Choi, "Expression of the human β–amyloid precursor protein gene from a yeast artificial chromosome in transgenic mice," *Proc. Natl. Acad. Sci. USA*, 90:10578–10582 (1993).

Peters, "Proteasomes: Protein degradation machines of the cell," *TIBS*, pp. 377–382 (1994).

Powers, et al., "Mechanism–Based Isocoumarin Inhibitors for Serine Proteases: Use of Active Site Structure and Substrate Specificity in Inhibitor Design," *J. Cell Biochem.*, 39(1)pp. 33–46 (1989).

Prior, et al., "Quantitative changes in the amyloid βA4 precursor protein in Alzheimer cercbrospinal fluid," *Neuroscience Letters*, 124:69–73 (1991).

Quon, et al., "Formation of β–amyloid protein deposits in brains of transgenic mice," *Nature*, 352:239–241 (1991).

Rao, et al., "Specificity in the Binding of Inhibitors to the Active Site of Human/Primate Aspartic Proteinases: Analysis of $P_2$–$P_1$–$P_1'$–$P_2'$ Variations," *J. Med. Chem.*, 36:2614–2620 (1993).

Revesz, et al., "Synthesis of P1 Aspartate–Based Peptide Acyloxymethyl and Fluoromethyl Ketones as Inhibitors of Interleukin–1β–Converting Enzyme," *Tetrahedron Letters*, 35(52):9693–9696 (1994).

Rich, "Inhibitors of cysteine proteinases," *Proteinase Inhibitors* Barrett and Salvesen (Eds.) Elsevier Science Publishers BV (Biomedical Division), pp. 153–178 (1986).

Roberts, et al., "1,2,4–Triazolo[4,3–α]pyrazine Derivatives with Human Renin Inhibitory Activity," *J. Med. Chem.*, 33:2326–2334 (1990).

Rock, et al., "Inhibitors of the proteasome block the degradation of most cell proteins and the generation of peptides presented on MHC Class I Molecules," *Cell*, 78:761–771 (1994).

Rosenberg, et al., "Studies Directed toward the Design of Orally Active Renin Inhibitors," *J. Med. Chem.*, 36:449–459 (1993).

Saito, et al., "Widespread activation of calcium–activated neutral proteinase (calpain) in the brain in Alzheimer disease: A potential molecular basis for neuronal degeneration," *Proc. Natl. Acad. Sci. USA*, 90:2628–2632 (1993).

Sasaki, et al., "Inactivation of calpain I and calpain II by specificity–oriented tripeptidyl chloromethyl ketones[1]," *J. Biochem.*, 99(1):173–179 (1986).

Schechter and Berger, "On the size of the active site in proteases. I. Papain," *Biochem. and Biophys. Res. Comm.*, 27(2):157–162 (1967).

Scheibel, et al., "Protease inhibitors and antimalarial effects," *Malaria and the Red Cell*, pp. 131–142 (1984).

Selkoe, "Amyloid protein and Alzheimer's disease," *Scientific American*, pp. 68–78 (1991).

Selkoe, "Physiological production of the β–amyloid protein and the mechanism of Alzheimer's disease," *TINS*, 16(10):403–409 (1993).

Seubert, et al., "Isolation and quantification of soluble Alzheimer's β–peptide from biological fluids," *Nature*, 359:325–327 (1992).

Seubert, et al., "Secretion of β–amyloid precursor protein cleaved at the amino terminus of the β–amyloid peptide," *Nature*, 361:260–263 (1993).

Sharma, et al., "Peptide transport by the multidrug resistance pump," *J. Biol. Chem.*, 267(9):5731–5734 (1992).

Sherwood, et al., "In vivo inhibition of cyclin B degradation and induction of cell–cycle arrest in mammalian cells by the neutral cysteine protease inhibitor N–acetylleucylleucylnorleucinal," *Proc. Natl. Acad. Sci. USA*, 90:3353–3357 (1993).

Skiles, et al., "Inhibition of Human Leukocyte Elastase (HLE) by N–Substituted Peptidyl Trifluoromethyl Ketones," *J. Med. Chem.*, 35(4);641–662 (1992).

Suzuki, et al., "An increased percentage of long amyloid β protein secreted by familial amyloid β protein precursor (βAPP$_{717}$) mutants," *Science*, 264:1336–1340 (1994).

Tsujinaka, et al., Synthesis of a new cell penetrating calpain inhibitor (calpeptin), *Biochem. and Biophys. Res. Comm.*, 153(3): 1201–1208 (1988).

Van Nostrandt, et al., "Protease nexin–II, a potent anti–chymotrypsin, shows identity to amyloid β–protein precursor," *Nature*, 341:546–549 (1989).

Van Nostrandt, et al., "Decreased levels of soluble amyloid β–protein precursor in cerebrospinal fluid of live Alzheimer disease patients," *Proc. Natl. Acad. Sci. USA*, 89:2251–2555 (1992).

Van Nostrandt, et al., "Alzheimer's disease and hereditary cerebral hemorrhage with amyloidosis–Dutch type share a decrease in cerebrospinal fluid levels of amyloid β–protein precursor," *Annals of Neurology*, 32(2):215–218 (1992).

Veale, et al., "Nonpeptidic Inhibitors of Human Leukocyte Elastase. 5. Design, Synthesis, and X–ray Crystallography of a Series of Orally Active 5–Aminopyrimidin–6–one–Containing Trifluoromethyl Ketones," *J. Med. Chem.*, 38:98–108 (1995).

Vinitsky, et al., "Inhibition of the chymotrypsin–like activity of the pituitary multicatalytic proteinase complex," *Biochemistry*, 31(39):9421–9428 (1992).

Wagner, et al., "Decreased levels of soluble amyloid β–protein precursor are associated with Alzheimer's disease in concordant and discordant monozygous twin pairs," *Annals of Neurology*, 36(2):215–220 (1994).

Wagner and McDonald, "Treating Alzheimer's disease with amyloid β–peptide inhibitors," *Biotech. Report*, pp. 106–107 (1994/1995).

Wang and Yuen, "Calpain inhibition: An overview of its therapeutic potential," *TiPS*, 15:412–419 (1994).

Wang, et al., "Secretion of the β/A4 amyloid precursor protein," *J. Biol. Chem.*, 266(25):16960–16964 (1991).

Wang, "Developing selective inhibitors of calpain," *TiPS*, 11:139–142 (1990).

*Primary Examiner*—Cecilia J. Tsang
*Assistant Examiner*—David Lukton

*Attorney, Agent, or Firm*—Stephanine L. Seidman; Heller Ehrman White & McAuliffe

[57] ABSTRACT

Methods of use of compounds for the treatment of disorders characterized by the cerebral deposition of amyloid are provided. Among the compounds provided for use in the methods are those of the formula:

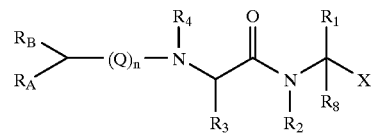

in which $R_1$ is preferably 2-methylpropenyl, 2-butenyl, cyclohexyl or cyclohexylmethyl; $R_2$, $R_4$, and $R_8$ are each preferably independently methyl or ethyl; $R_3$ is preferably iso-butyl or phenyl; Q is preferably —C(O)—; $R_B$ is preferably iso-butyl; $R_A$ is —$(T)_m$—$(D)_m$—$R_1$, in which T is preferably oxygen or NH, m is 0 or 1, and D is preferably $C_{1-4}$ alkyl or $C_{2-4}$ alkenyl; and X is preferably an aldehyde, α-ketoester or α-ketoamide.

17 Claims, No Drawings

PEPTIDE AND PEPTIDE ANALOG PROTEASE INHIBITORS

This is a continuation of application Ser. No. 08/369,422, filed Jan. 6, 1995, now U.S. Pat. No. 5,804,560.

FIELD OF THE INVENTION

This invention relates to peptidyl compounds useful for a variety of physiological end-use applications. More specifically, di- and tripeptide analogs that are useful in the treatment of neurodegenerative disease states and in the treatment of the degeneration of the neuronal cytoskeleton are provided.

SUMMARY OF THE INVENTION

Di- and tri-peptide compounds and methods of treating certain disorders, particularly cognitive disorders, and methods of inhibiting proteases are provided. The methods use compounds having formulae:

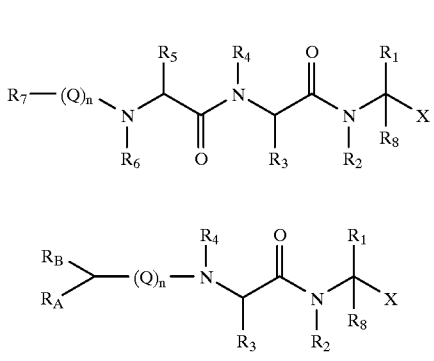

or the hydrates and isosteres, diastereomeric isomers and mixtures thereof, or pharmaceutically acceptable salts thereof in which:

$R_1$, $R_2$, $R_3$, $R_4$, $R_5$, $R_6$, $R_7$, $R_8$, $R_A$, $R_B$, X, Q and n are selected from among (i), (ii), (iii), (iv), (v), (vi), (vii) or (viii) as follows: (i) $R_1$, $R_3$, $R_5$, and $R_B$, are each independently selected from a side chain of a naturally occurring α-amino acid, H, alkyl, preferably lower ($C_{1-6}$) alkyl, alkenyl, preferably $C_{2-10}$ alkenyl, alkynyl, preferably $C_{2-6}$ alkynyl, aryl, aralkyl, aralkenyl, aralkynyl, heteroaryl, heteroaralkyl, heteroaralkenyl, Y-substituted aryl, aralkyl, aralkenyl, aralkynyl, and Z-substituted heteroaryl, heteroaralkyl, heteroaralkenyl, in which Y is selected from halogen, lower alkyl, alkoxy, OH, haloalkyl, preferably $CF_3$, $NO_2$, nitrile, S-alkyl, phenyl, and —NRR, R is H or alkyl, preferably lower alkyl, OH and halo-lower alkyl, particularly $CF_3$, Z is lower alkyl, preferably $C_{1-4}$ alkyl, or halo lower alkyl, preferably $C_{1-4}$ haloalkyl, more preferably $CF_3$;

$R_2$, $R_4$, $R_6$, and $R_8$ are each independently selected from among H and lower alkyl, preferably $C_{1-4}$ alkyl;

$R_7$ is selected from among $C_{1-6}$ alkyl, aryl, alkenyl, 9-fluoroenyl, aralkyl, aralkenyl, aralkynyl the aryl groups are unsubstituted or are substituted with Z;

Q is selected from among —C(O)—, —O—C(O), —S(O)$_2$— and HN—C(O)—;

n is zero or one;

$R_A$ is —(T)$_m$—(D)$_m$—$R_1$ in which T is O or NH, and D is $C_{1-4}$ alkyl or $C_{2-4}$ alkene; and m is zero or one;

X is selected from —(CH$_2$)$_r$C(O)H, —(CH$_2$)$_r$C(O) haloalkyl, —(CH$_2$)$_r$C(O)(CH$_2$)$_r$CHN$_2$, —C(CH$_2$)$_r$(O)C(CH$_2$)$_r$(O)OR$_D$, —(CH$_2$)$_r$C(O)(CH$_2$)$_r$C(O)NR$_D$R$_D$, —(CH$_2$)$_r$C≡N, —(CH$_2$)$_r$C(OH)(CH$_2$)$_r$C(O)U, —(CH$_2$)$_r$C(OH)CH$_2$C(O)U, —(CH$_2$)$_r$C(O)W and —(CH$_2$)$_r$C(O)CH$_2$W, in which: R$_D$ is selected from among H, alkyl, preferably lower alkyl, more preferably $C_{1-4}$ alkyl, phenyl, benzyl, and phenethyl; U is —OR$_D$ or —NR$_D$R$_D$, and W is —OR$_D$, —SR$_D$, and —NR$_D$R$_D$, or heterocyclic moiety, preferably containing 4–6, more preferably 5 or 6 members in the ring, and preferably one or two heteroatoms, selected from O, S, or N, in the ring, and r is 0–5, preferably 0–3, more preferably 0 or 1, most preferably 0; or (ii) $R_1$, $R_2$, $R_3$, $R_4$, $R_5$, $R_8$, X and Y are selected as in (i), (iv) or (v);

V is OH, halogen, lower alkyl, preferably methyl or ethyl or halogen-substituted lower alkyl, preferably methyl or ethyl, and is preferably preferably OH;

n is zero; and $R_6$ and $R_7$ are each independently selected as follows:
(a) from lower alkyl, preferably $C_{1-3}$ alkyl, or lower alkyl linked to a heteroatom, preferably $C_{1-3}$ alkyl, with the proviso that there is at least one carbon atom between the N to which $R_6$ and $R_7$ are each is attached and the heteroatom, and
(b) $R_6$ and $R_7$ are unsubstituted or substituted with one or more substituents selected from Y or preferably V, which is selected from OH, halogen, lower alkyl, preferably methyl or ethyl, or halogen-substituted lower alkyl, preferably methyl or ethyl, and is more preferably OH, and
(c) together with the atoms to which each is attached form a heterocyclic moiety, preferably a 5–6 atomed heterocyclic moiety, more preferably selected from among morpholino, thiomorpholino, pyrrolidinyl, or V-substituted pyrrolidinyl, particularly 4-hydroxy pyrrolidinyl; or (iii) $R_1$, $R_2$, $R_3$, $R_4$, $R_5$, $R_8$, $R_A$, X and $R_B$ are selected as in (i);

V is as defined in (ii);

Q is C(O);

n is one; and $R_6$ and $R_7$ are each independently selected as follows:
(a) from carbonyl (C=O), phenyl, a heteroatom, lower alkyl, preferably $C_{1-3}$ alkyl, or lower alkyl linked to a heteroatom, preferably $C_{1-3}$ alkyl, and
(b) each is unsubstituted or substituted with Y, preferably with V, and
(c) together with the atoms to which they are attached form a cyclic moiety, preferably a 4–6 membered cyclic or 8–12 membered bicylic moiety, and
(d) $R_6$ and $R_7$ are selected with the proviso that when two or more heteroatoms are present there is a carbon atom between the heteroatoms; and
(e) when the moiety is a heterocycle, it is preferably succinimide, phthalimide or maleimide; or (iv) $R_3$, $R_4$, $R_5$, $R_6$, $R_7$, $R_A$, $R_B$, Q, X and n are as defined in any of (i)–(iii) or (v)–(viii), V is as defined in (ii);

$R_8$ is H; and $R_1$ and $R_2$ are each independently selected as follows:
(a) from lower alkyl, preferably $C_{1-4}$ alkyl, or lower alkyl linked to a heteroatom, preferably $C_{1-4}$ alkyl, or a heteroatom, with the proviso when more than one heteroatom is present, there is at least one carbon atom between each heteroatom, and
(b) $R_1$ and $R_2$ are unsubstituted or substituted with Y, preferably with V, and (c) together with the atoms to which they are attached form a heterocyclic moiety, preferably a 4–6 membered heterocyclic moiety, that is preferably morpholino, thiomorpholino, pyrrolidinyl, or V-substituted pyrrolidinyl, particularly 4-hydroxy pyrrolidinyl; or (v) $R_1$, $R_2$, $R_5$, $R_6$, $R_7$, $R_8$, $R_A$, $R_B$, X, Q and n are as defined in any of (i)–(iv) or (vi)–(viii);

V is as defined in (ii);

$R_3$ and $R_4$ are each independently selected as follows:
(a) from lower alkyl, preferably $C_{1-4}$ alkyl, or lower alkyl linked to a heteroatom, preferably $C_{1-4}$ alkyl, or a heteroatom, with the proviso when more than one heteroatom is present, there is at least one carbon atom between each heteroatom, and
(b) is unsubstituted or substituted with Y, preferably with V, and
(c) together with the atoms to which they are attached form a heterocyclic moiety, preferably a 4–6 membered heterocyclic moiety, that is preferably morpholino, thiomorpholino, pyrrolidinyl, or V-substituted pyrrolidinyl, particularly 4-hydroxy pyrrolidinyl; or (vi) $R_1$, $R_2$, $R_3$, $R_4$, $R_7$, $R_8$, Q, X and n are as defined in any of (i), (iv) or (v);

V is as defined in (ii);

$R_5$ and $R_6$ are each independently selected as follows:
(a) from lower alkyl, preferably $C_{1-4}$ alkyl, or lower alkyl linked to a heteroatom, preferably $C_{1-4}$ alkyl, or a heteroatom, with the proviso that when more than one heteroatom is present, there is at least one carbon atom between each heteroatom, and
(b) $R_5$ and $R_6$ are unsubstituted or substituted with Y, preferably with V, and
(c) together with the atoms to which they are attached form a heterocyclic moiety, preferably a 4–6 membered heterocyclic moiety, that is preferably morpholino, thiomorpholino, pyrrolidinyl, or V-substituted pyrrolidinyl, particularly 4-hydroxy pyrrolidinyl; or (vii) $R_1$, $R_2$, $R_3$, $R_4$, $R_6$, $R_8$ and X are selected as in (i) (iv) or (v);

V is as defined in (ii);

n is zero; and $R_5$ and $R_7$ are each independently selected as follows:
(a) from lower alkyl, preferably $C_{1-4}$ alkyl, or lower alkyl linked to a heteroatom, preferably $C_{1-4}$ alkyl, or a heteroatom, with the proviso that when more than one heteroatom is present, there is at least one carbon atom between each heteroatom, and
(b) $R_5$ and $R_7$ are unsubstituted or substituted with Y, preferably with V, and
(c) together with the atoms to which they are attached form a heterocyclic moiety, preferably a 4–6 membered heterocyclic moiety, that is preferably morpholino, thiomorpholino, pyrrolidinyl, or V-substituted pyrrolidinyl, particularly 4-hydroxy pyrrolidinyl; or (viii) $R_1$, $R_2$, $R_3$, $R_4$, $R_5$, $R_8$, X and Y are selected as in (i), (iv) or (v);

V is as defined in (ii);

$R_6$ and $R_7$, which are defined as in (ii), together with the atoms to which each is attached form a bicyclic heterocycle or cyclic moiety, preferably, when n is zero, a reduced isoquinoline, and is preferably 1,2,3,4, tetrahydroisoquinoline;

in all instances, unless specified, the carbon chains, which may be straight or branched, contain from 1 to about 12 carbons preferably 1 to 6, and most preferably 4–6 carbons, and the cyclic moieties preferably contain one ring or two fused rings with from 3 to 16 atoms, preferably 4 to 12, with 4 to 6 in each ring, in the ring structures.

Unless otherwise stated, the α-amino acids of the compounds of formulae I and II are preferably in their L-configuration. In their preferred configuration with reference to a particular compound, $R_1$ is S, $R_3$ is S, and $R_5$ is R/S. Also, a compound of these formulae may be in free form, e.g., an amphoteric form, or a salt form, e.g., an acid addition or an anionic salt. A compound may be converted to its salt or base form in an art-known manner, one from another. Preferred salts are trifluoracetate, hydrochloride, sodium, potassium or ammonium salts, although the scope of the salts embraced is not limited thereto, the scope being extended to include all of those salts known to be used in the art of chemistry.

Compounds are also provided herein. These compounds may be used in the methods. The compounds have formulae I or II as defined above, but with the proviso that, when the compounds have formula (I): (1) at least one of the amino acid residues in the resulting tri-peptide is a non-naturally-occurring α-amino acid or at least one of the $R_1$, $R_3$ and $R_5$ is not a side chain of a naturally-ocurring amino acid; and (2) when X is an aldehyde, the non-naturally occurring amino acid (or side chain thereof) is other than norleucine or norvaline, and when the compounds have formula (II) and X is an aldehyde, $R_1$ cannot be the side chain of norleucine or norvaline.

In some embodiments the compounds of formula (II) are also selected such that: (1) at least one of the amino acid residues in the resulting dipeptide is a non-naturally-occurring α-amino acid or at least one of the $R_1$ and $R_3$ is not a side chain of a naturally-ocurring amino acid; and (2) when X is an aldehyde, the non-naturally occurring amino acid (or side chain thereof) is other than norleucine or norvaline.

In certain preferred embodiments, the compounds have formulae I or II, particularly formula I, as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) when $R_1$ is the side chain from a non-naturally occuring amino acid, it is not the side chain of norleucine or norvaline.

In other preferred embodiments, the compounds have formulae I or II, particularly when the compounds have formula I, as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) none of $R_1$, $R_3$ and $R_5$ is the side chain of norleucine or norvaline.

The compounds provided herein are preferred for use in the methods, particularly the methods of treatment of cognitive disorders.

Pharmaceutical compositions containing a compound of formulae (I) and (II) are provided. In particular, pharmaceutical compositions formulated for single dosage administration are provided.

Methods of treatment of diseases, particularly cognitive disorders are provided and are effected by administering an effective amount of the pharmaceutical compositions. In particular, methods of treating a patient suffering from a neurodegenerative disease selected from among Alzheimer's disease, cognition deficits, Down's Syndrome, Parkinson's disease, cerebral hemorrhage with amyloidosis, dementia pugilistica, head trauma and any disorder characterized by an accumlation of plaques in the brain, by administering to the patient a therapeutically effective amount of a compound of formulae (I) and (II) or compounds of formulae (I) and (II) in which $R_1$, $R_3$, $R_5$ and $R_B$ can all be side chains of naturally-occurring amino acids are provided.

Methods of treating a patient suffering from a disease state characterized by the degeneration of the cytoskeleton arising from a thrombolytic or hemorrhagic stroke by administering a therapeutically effective amount of a compound of formulae (I) and (II) are provided.

Assays for detecting compounds that modulate the processing of amyloid precursor protein (APP) and other related proteins are also provided. In particular, assays that detect a relative decrease in the amount of amyloidogenic Aβ peptide produced by cultured cells that express APP, such as cultured human glioblastoma cell lines that have been transfected with DNA encoding either a wild-type 695 amino acid isoform of APP or a mutein of APP are provided. A positive in vitro assay occurs when: (1) there is a decrease in the ~4-kDa amyloid β-protein (Aβ) in the medium relative to control cultures; and/or (2) the relative amount of soluble APP (referred to as sAPP, also sβPP and total soluble APP) in the medium increases; and/or (3) there is a decrease in the amount of C-terminal fragments of APP larger than 9 kDa in the cell lysate as a result of differential processing; and/or (4) there is an increase in the amount of α-sAPP in the medium relative to control cultures.

Methods of detecting markers indicative of neurodegenerative disorders characterized by deposition of cerebral amyloid by detecting a decrease in the ratio of α-sAPP to total sAPP or a decrease in the amount of α-sAPP in a sample of CSF compared to such ratio or amount in control CSF from individuals who do not have this disorder or compared to predetermined standard ratios and amounts, are also provided herein.

Methods of identifying compounds that are effective for treating patients with neurodegenerative disorders characterized by deposition of cerebral amyloid by administering the compound to a subject and detecting an increase in the ratio of α-sAPP to total sAPP or an increase in the amount of α-sAPP in a sample of CSF from the subject compared to such ratio or amount in a sample of CSF prior to administering the compound are also provided herein.

DETAILED DESCRIPTION AND PREFERRED EMBODIMENTS

Unless defined otherwise, all technical and scientific terms used herein have the same meaning as is commonly understood by one of skill in the art to which this invention belongs. All patents and publications referred to herein are incorporated by reference.

As used herein, the term "alkyl" includes the straight, branched-chain and cyclic manifestations thereof, the number of carbon atoms is generally specified. Where not specified the alkyl groups preferably contain from about 1 up to about 10 or 12, more preferably 1 to 6 or 7, and most preferably 4 to 6 carbons. Exemplary of such moieties are methyl, ethyl, propyl, cyclopropyl, isopropyl, n-butyl, t-butyl, sec-butyl, cyclobutyl, pentyl, cyclopentyl, n-hexyl, n-nonal, n-decyl, cyclohexyl, cyclohexylmethyl, cyclohexylethyl, and the like. Lower alkyl refers to alkyl groups containing six or fewer carbon atoms.

As used herein, heteroatoms are selected from O, N or S.

The term "aryl" within the definitions of X, $R_B$, $R_1$, $R_3$, $R_5$, and $R_7$ includes carbocyclic and heterocyclic moieties. Preferred aralkyl and aryl moieties are phenyl, benzyl, phenethyl, 1- and 2-naphthalmethyl, 1- and 2-naphthyl, 2-, 3-, 4-pyridyl, 2- and 3-furyl, 1- and 2-indenyl, 1- and 2-thiophenyl, imidazolyl, indolyl, 2- and 3-thienyl, indole-3-ethyl and the residue of 1,2,3,4,tetrahydroisoquinoline. Other carbocycles are such fused moieties as pentalenyl, indenyl, naphthaleneyl, naphthylmethyl, azulenyl, heptalenyl, acenaphthylenyl, 9-fluorenyl, phenalenyl, phenanthrenyl, anthracenyl, triphenylenyl, pyrenyl, chryrsenyl, and naphthacenyl. Exemplary of alkynyl is propynyl. Exemplary of alkenyl moieties are 2-methyl-2-propenyl, 2-methyl-1-propenyl, propenyl, 1-butenyl, 2-butenyl, 3-butenyl, 2,2-difluoroethenyl, as well as those straight and branched chained moieties having up to two double bonds. Cyclic carbon moieties preferably contain one or two fused rings typically from 3 up to about 16, preferably 4 up to about 12 carbons.

Haloalkyl embraces such moieties as $CF_3$, —$CF_2H$, —$CFH_2$, $CH_2Cl$ and $CH_2Br$ and other halo substituted lower alkyls. Exemplary of aryloxyalkenyl and aryloxyalkynyl moieties of $R_A$ are phenoxymethyl, $CF_3$-substituted phenoxymethyl, benzyloxymethyl, phenoxybutyr-2-ene, 1-phenyl-1-propene, $CF_3$-phenoxybutyr-2-ene, $CF_3$-benzyloxymethyl, these moieties are preferred when $R_A$ is other than $R_1$.

In those instances in which a substituent, such as the $R_1$, $R_3$, and/or $R_5$ moiety, embrace the residue -or side chain- of a naturally occurring α-amino acid, it is to be noted that each α-amino acid has a characteristic "R-group," the R-group being the residue -or side chain- attached to the α-carbon atom of the amino acid. For example, the residue of glycine is H, for alanine it is methyl, for valine it is isopropyl. The specific residues of the naturally occurring α-amino acids are well known to those of skill in this art [see, e.g., A. L. Lehninger, *Biochemistry: The Molecular Basis of Cell Structure and Function*, 1970 (or any edition thereafter), Worth Publishers, NY, see, particularly Chapter 4).

As used herein, the residues of naturally occurring α-amino acids are the residues of those 20 α-amino acids found in nature which are incorporated into protein by the specific recognition of the charged tRNA molecule with its cognate mRNA codon in humans.

As used herein, the moieties in the peptide analogs provided herein are designated according to the system of nomenclature in which the binding region of a proteinase is considered as a series of subsites, S, along the surface of the enzyme [see, Schecter and Berger (*Biochem. Biophys. Res. Comm.*, 27, 157–162 (1967)]. Each subsite binds an individual peptide residue, P. This originally designed for papain, has been adapted to other proteases. Thus, for convenience and in keeping with the customary peptide designations, the moiety bearing the $R_1$ side chain (or residue) is designated as the $P_1$ moiety, the moiety bearing the $R_3$ side chain (or residue) is designated as the $P_2$ moiety, and that which bears the $R_5$ moiety is designated as the $P_3$ moiety.

The N-terminal capping moieties represented by the $R_7$—$(Q)_n$— and $(R_B)$—$CH(R_A)$—$(Q)_n$— include those moieties that protect molecules from degradation by aminopeptidases and include, but are not limited to, such generic groupings as arylcarbonyl, alkylcarbonyl, alkoxycarbonyl, aryloxycarbonyl, aralkyloxycarbonyl, aralkylsulfonyl, alkylsulfonyl, arylsulfonyl, and other equivalently functioning groups known in the art.

As defined particularly for the capping groups herein, either individually or as a part of a larger group, "alkyl" means a linear, cyclic, or branched-chain aliphatic moiety of 1 to 20 carbon atoms; "aryl" means an aromatic moiety, e.g., phenyl, of 6 to 18 carbon atoms, unsubstituted or substituted with one or more alkyl, substituted alkyl, nitro, alkoxy, or halo groups; "substituted alkyl" means an alkyl group having a substituent containing a heteroatom or heteroatoms such as N, O, or S; "halo" means Cl or Br; and "alkaryl" means an aryl moiety of 6 to 19 carbon atoms having an aliphatic substituent, and, optionally, other substituents such as one or more alkyl, substituted alkyl, alkoxy or amino groups.

Examples of suitable N-terminal blocking groups include, but are not limited to, formyl, t-butyloxycarbonyl, isopropyloxycarbonyl, allyloxycarbonyl, acetyl, trifluoracetyl, methyl, ethyl, benzyl, benzoyl, acetoacetyl, chloroacetyl, succinyl, phthaloxy, phenoxycarbonyl, methoxysuccinyl, p-methoxybenzenesulfonyl, p-toluenesulfonyl, isovaleroyl, methanesulfonyl, benzyloxycarbonyl, substituted benzyloxycarbonyl, adipyl, suberyl, phthalamido-, morpholino-, azelayl, dansyl, tosyl, 2,4-dinitrophenyl, fluorenyl-methoxycarbonyl, methoxyazelayl, methoxyadipyl, methoxysuberyl, 1-adamantanesulfonyl, 1-adamantaneacetyl, 2-carbobenzoyl, phenylacetyl, t-butylacetyl, bis[(1-methyl) methyl]acetyl, and thioproline.

As used herein, an effective amount of a compound for treating a disorder is an amount that is sufficient to ameliorate, or in some manner reduce a symptom or stop or reverse progression of a condition. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography [TLC], gel electrophoresis and high performance liquid chromatography [HPLC], used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, pharmaceutical activity refers to the activity of the compounds herein to treat a disorder.

As used herein, the $IC_{50}$ refers to an amount, concentration or dosage of a particular compound that achieves a 50% inhibition of a maximal response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon In vivo administration, is metabolized or otherwise converted to the biologically, pharmaceutically or therapeutically active form of the compound. To produce a pro-drug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is identified, those of skill in the pharmaceutical art generally can design prodrugs of the compound [see, e.g., Nogrady (1985) *Medicinal Chemistry A Biochemical Approach*, Oxford University Press, New York, pages 388–392].

As used herein, amyloid precursor protein (APP) is the progenitor of deposited amyloidogenic Aβ peptides (Aβ) found in the senile plaques in patients with diseases, such as Alzheimer's disease (AD), that are characterized by such deposition. α-sAPP is an alternative cleavage product of APP; its formation precludes formation of Aβ.

As used herein, Cha is cyclohexylalanine.

As used herein, the abbreviations for any substituent groups, protective groups, amino acids and other compounds, are, unless indicated otherwise, in accord with their common usage, recognized abbreviations, or the IUPAC-IUB Commission on Biochemical Nomenclature [see, (1972) *Biochem.* 11:1726].

A. The Tri- and Dipeptide Analogs

Compounds of formulae (I) and (II):

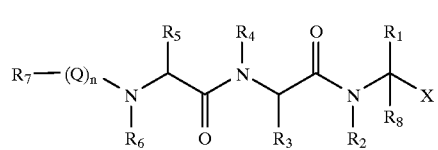

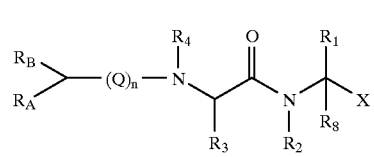

or the hydrates and isosteres, diastereomeric isomers and mixtures thereof, or pharmaceutically acceptable salts thereof are provided, but with the proviso that, when the compounds have formula (I): (1) at least one of the amino acid residues in the resulting tri-peptide is a non-naturally-occurring α-amino acid or at least one of the $R_1$, $R_3$ and $R_5$ is not a side chain of a naturally-ocurring amino acid; and (2) when X is an aldehyde, the non-naturally occurring amino acid (or side chain thereof) is other than norleucine or norvaline, and when the compounds have formula (II) and X is an aldehyde, $R_1$ cannot be norleucine or norvaline.

In some embodiments the compounds of formula (II) are also selected such that: (1) at least one of the amino acid residues in the resulting dipeptide is a non-naturally-occurring α-amino acid or at least one of the $R_1$ and $R_3$ is not a side chain of a naturally-ocurring amino acid; and (2) when X is an aldehyde, the non-naturally occurring amino acid (or side chain thereof) is other than norleucine or norvaline.

In certain preferred embodiments, the compounds have formulae (I) or (II), particularly formula (I), as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) when $R_1$ is the side chain from a non-naturally occuring amino acid, it is not the side chain of norleucine or norvaline.

In other preferred embodiments, the compounds have formulae (I) or (II), particularly formula (I), as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) none of $R_1$, $R_3$ and $R_5$ is the side chain of norleucine or norvaline.

$R_1$, $R_2$, $R_3$, $R_4$, $R_5$, $R_6$, $R_7$, $R_8$, $R_A$, $R_B$, X, Q and n are selected from among (i), (ii), (iii), (iv), (v), (vi), (vii) or (viii) as described above.

Preferred among these compounds, defined with any of the provisos, are those in which:

$R_1$ is preferably a straight or branched chain carbon chain containing 2 to 6 carbons and one unsaturated, preferably a double bond, or is a cyclic moiety containing from 5 to 6 members, and is more preferably 2-methyl propene, 2-butene, cyclohexyl, lower alkyl-substituted cyclohexyl or cyclohexylmethyl;

$R_2$, $R_4$, and $R_8$ are each independently selected from among H or $C_{1-4}$ alkyl, and more preferably methyl or ethyl;

$R_3$ is $C_{1-4}$ alkyl, phenyl, benzyl, naphthyl, hydroxyphenyl, 1-aminobutyl, acetamide, and more preferably iso-butyl, benzyl or phenyl;

$R_5$ is $C_{1-4}$ alkyl, and more preferably iso-butyl;

$R_6$ is H or $C_{1-4}$ alkyl, and more preferably H or methyl;

$R_7$—$(Q)_n$ is acyl, benzyloxycarbonyl (Cbz), 9-fluorenylmethylcarbonate (Fmoc), Ac, Boc, tosyl, with Cbz, Ac and Fmoc being more preferred, and Cbz and Ac most preferred;

Q is —C(O)—, —S(O)$_2$— and —O—C(O), with —C(O)— and —O—C(O) being more preferred, and —O—C(O) most preferred;

$R_B$ is $C_{1-4}$ alkyl or $C_{2-4}$ alkenyl, and more preferbly iso-butyl;

$R_A$=—$(T)_m$—$(D)_m$—$R_1$, in which T is oxygen, or nitrogen, with oxygen being more preferred, and D is $C_{1-4}$ alkyl or $C_{2-4}$ alkenyl, with a mono-unsaturated $C_{3-4}$ alkenyl being more preferred; and X is aldehyde, α-ketoester, α-ketoamide, trifluoromethylketone, diazomethylketone, or nitrile, with an aldehyde, α-ketoester or α-ketoamide being more preferred.

Also among preferred compounds are those of formula (II) in which $R_B$ and $R_A$ and the atom to which each is attached and $(Q)_n$ form (2SR)-N-[(2S)-2-benzoxy-4-methylpentanoyl] or (2SR)-N-[(2R)-[2-(1'-phenyl-1'-propene)-4-methylpentanoyl or valeroyl.

When $R_1$, $R_3$, and $R_5$ are a side-chain from other than a residue of a naturally occurring α-amino acid, it is preferred that such moiety is a straight or branched carbon chain, preferably containing at least one unsaturated bond, preferably a double bond, and 2 to 10, preferably 4 to 7, more preferably 4–6 carbon atoms in the chain, such as, but not limited to, 2-methyl propene and 2-butene, or is a cylic moiety, preferably containing 4–6 members, more preferably is cyclohexylmethyl. The resulting residues including such moieties include, but are not limited to, 2-amino-4-methyl-4-pentenoic acid, 2-amino-4-hexenoic acid, cyclohexylalanine and cyclohexylglycine, with (2S)-2-amino-4-methyl-4-pentenoic acid and (2S)-2-amino-4-hexenoic acid being preferred.

When the compounds are used in the methods of treating neurodegenerative diseases and cognitive disorders provided herein, the side chains from norvaline and leucine are also preferred.

In particular, preferred compounds are those in which at least one of $R_1$, $R_3$, and $R_5$ is 2-methyl-propene, 2-butene, cyclohexyl or cyclohexylmethyl. More preferred are those in which $R_1$, $R_3$, and $R_5$ are 2-methyl-propene, 2-butene, cyclohexyl or cyclohexylmethyl, and X is C(O)H, C(O)—C(O)OR$_D$, C(O)—C(O)—NR$_D$R$_D$, C(O)CHN$_2$, C(O)CF$_3$, or C≡N.

Preferred heterocyclic ring moieties containing $R_1$ and $R_2$ and the atoms to which they are attached, when $R_8$ is H, are morpholino, thiomorpholino, pyrrolidinyl, or V-substituted pyrrolidinyl, particularly 4-hydroxy pyrrolidinyl.

Preferred heterocyclic ring moieties containing $R_6$ and $R_7$ and the atoms to which they are attached when $(Q)_n$ is a carbonyl group are selected from among succinimide, phthalimide or maleimide, with phthalimide being more preferred.

Preferred heterocyclic ring moieties containing $R_6$ and $R_7$ and the atoms to which they are attached when n in $(Q)_n$ is zero are morpholino, thiomorpholino, pyrrolidinyl, V-substituted pyrrolidinyl, particularly 4-hydroxy pyrrolidinyl, or 1,2,3,4-tetrahydroisoquinoline.

Preferred moieties, when n is zero, and when $R_3$ and $R_4$ or $R_5$ and $R_7$, and taken together with the atoms to which they are attached, form heterocyclic moieties are morpholino, thiomorpholino, pyrrolidinyl, or V-substituted pyrrolidinyl, particularly 4-hydroxy pyrrolidinyl.

The following are among the preferred compounds provided herein: N-Ac-L-Leu-L-Leu-DL-cyclohexylalaninal; (2SR)-N-Cbz-L-Leu-L-Leu N-[2-(4-methyl-4-pentenal)] amide; (2SR)-H-L-Leu N-[2-(ethyl 4-methyl-4-pentenoate)] amide hydrochloride; (2SR)-N-[(2S)-2-benzoxy-4-methylpentanoyl]-L-Leu N-[2-(4-methyl-4-pentenal)] amide; (2SR)-N-[(2R)-[2-(1'-phenyl-1'-propene)-4-methylpentanoyl]]-L-Leu-N-[2-(4-methyl-4-pentenal)] amide; N-Cbz-L-Leu-L-Leu-DL-cyclohexylglycinal; (2SR)-N-Ac-L-Leu-L-Leu N [2-(trans-4-hexenal)]amide; (2SR)-N-Ac-L-Leu-L-Leu N-[2-(4-methyl-4-pentenal)] amide; (2SR)-N-Cbz-L-Leu-L-Phe-DL-cyclohexylalaninal; and (2SR)-N-Cbz-L-Leu-L-Phe-N-[2-(4-methyl-4-pentenal)]amide.

The following are among the preferred compounds for use in the methods herein: N-Cbz-L-Leu-L-Leu-DL-(methyl) norleucinal; N-Ac-L-Leu-L-Leu-DL-cyclohexylalaninal; (2S)-N-Ac-L-Leu-L-Leu N-[2-(pentanenitrile)]amide; N-Cbz-L-Leu-L-Leu-DL-Nle-CO$_2$Et; N-Cbz-L-Leu-L-Leu-DL-Nle-CO$_2$H; N-Cbz-L-Leu-L-Leu-DL-Nle-CONHEt; (2SR)-N-Cbz-L-Leu-L-Leu N-[2-(4-methyl-4-pentenal)] amide; (2S)-N-Cbz-L-Leu-L-LeuN-[2-(thiazole-oxo-pentyl]amide; N-Ac-L-Leu-L-Leu-L-Nle-COCHN$_2$; (3SR)-N-Ac-L-Leu-L-Leu N-[3-(1,1,1-trifluoro-2-oxo-heptyl)] amide; (2SR)-H-L-Leu N-[2-(ethyl 4-methyl-4-pentenoate)]

amide hydrochloride; (2SR)-N-[(2S)-2-benzoxy-4-methylpentanoyl]-L-Leu N-[2-(4-methyl-4-pentenal)] amide; (2SR)-(3S)-N-Cbz-L-Leu-Leu N-[3-(2-hydroxy-heptanoic acid)]amide; (2SR)-(3S)-N-Cbz-L-Leu-L-LeuN-[3-(methyl 2-hydroxy-heptanoate)]amide; (2SR)-(3S)-N-Cbz-L-Leu-L-Leu N-[3-(benzyl 2-hydroxy-heptamide)] amide; (3SR)-(4S)-N-Cbz-L-Leu-L-Leu N-[4-(benzyl 3-hydroxy-octamide)]amide; (3S)-N-Cbz-L-Leu-L-Leu N-[3-(1-furfylthio-2-oxoheptane]amide; (2SR)-N-[(2R)-[2-(1'-phenyl-1'-propene)-4-methylpentanoyl]]-L-Leu-N-[2-(4-methyl-4-pentenal)]amide; N-Cbz-L-Pro-L-Leu-L-norleucinal; N-Cbz-L-Leu-L-Leu-DL-cyclohexylglycinal; N-Fmoc-Leu-L-Leu-DL-norleucinal;(2SR)-N-Ac-L-Leu-L-LeuN[2-(trans-4-hexenal)]amide;N-Ac-L-Leu-L-Phe-DL-norleucinal; N-Cbz-L-Leu-L-Leu-L-norleucinal; (2SR)-N-Ac-L-Leu-L-Leu N-[2-(4-methyl-4-pentenal) ]amide; N-Cbz-L-Leu-L-(methyl)Leu-DL-norleucinal; N-Dansyl-L-Leu-L-Leu-DL-norleucinal; N-Ac-L-Phe-L-Leu-DL-norleucinal; (2SR)-N-Cbz-L-Leu-L-Phe-DL-cyclohexylalaninal; and (2SR)-N-Cbz-L-Leu-L-Phe-N-[2-(4-methyl-4-pentenal)]amide.

Also provided herein are the α-ketoesters and α-ketoamides of any of the above listed compounds. Further intended for use herein are any of the above-listed compounds in which $R_2$ and/or $R_4$ and/or $R_6$ are methyl (i.e., the N-mehtyl derivatives of the compounds).

B. Synthesis of the Tri- and Dipeptide Analogs

1. Reaction schemes

The following reaction schemes are depicted to illustrate the construction of the peptides provided herein and to illustrate the variety of reactions that may be used to prepare the intermediates from which compounds of formulae I and II may be prepared.

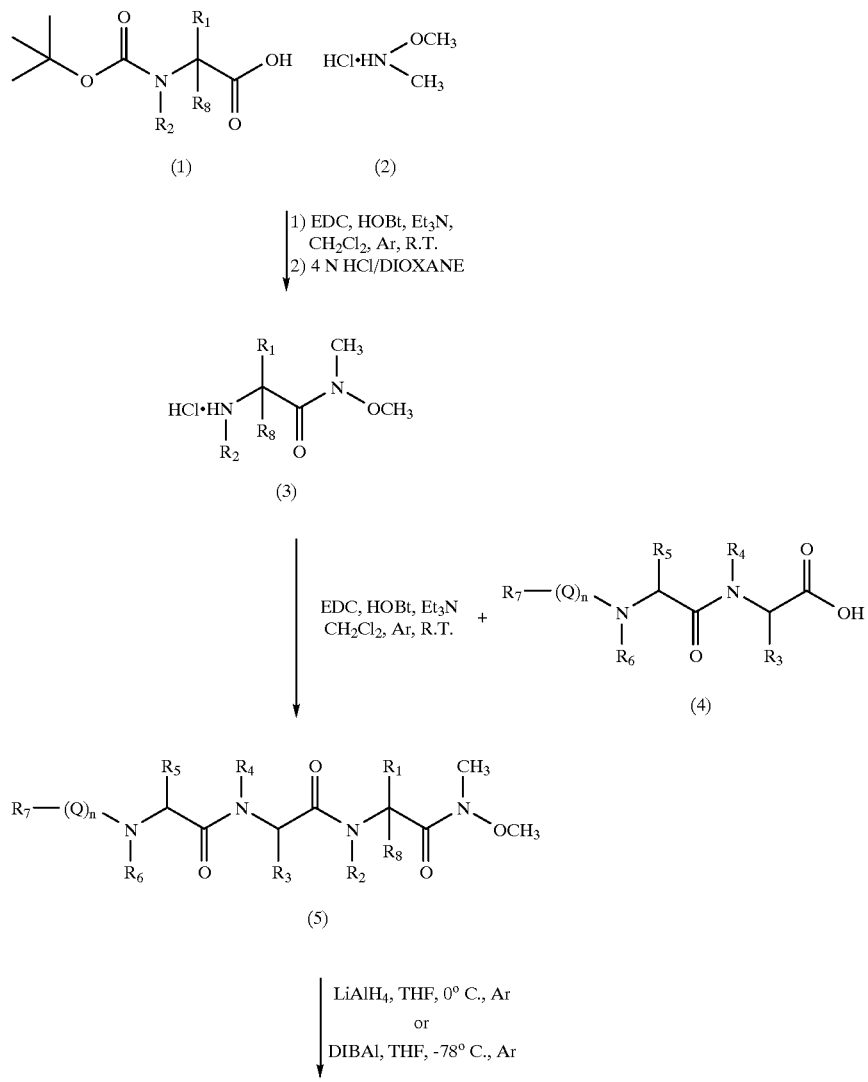

REACTION SCHEME A

-continued
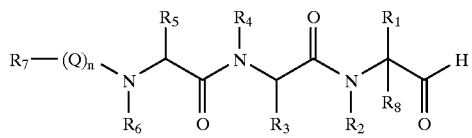
(6)
wherein the $R_1$, $R_2$, $R_3$, $R_4$, $R_5$, $R_6$, $R_7$, $R_8$ and $(Q)_n$ are as defined above.
REACTION SCHEME B
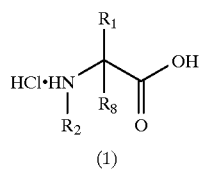
(1)
↓ HCl(g), ROH
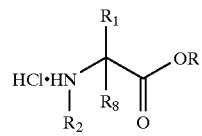
(2)
↓ EDC, HOBt, Et$_3$N, CH$_2$Cl$_2$, Ar, R.T.
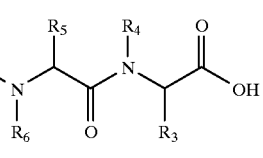
(A-4)
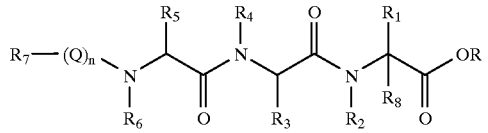
(3)
↓ LiBH$_4$, THF, 0° C., Ar

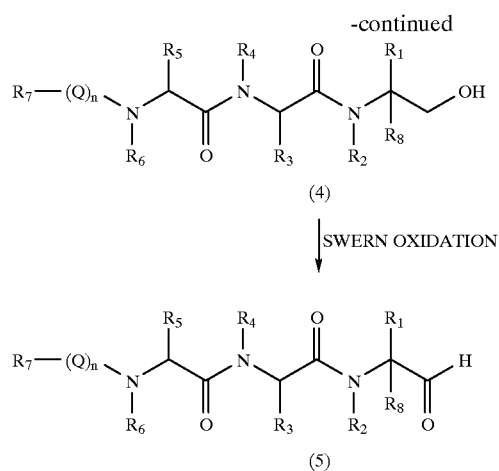
wherein the $R_1$, $R_2$, $R_3$, $R_4$, $R_5$, $R_6$, $R_7$, $R_8$ and $(Q)_n$ are as defined above.
REACTION SCHEME C
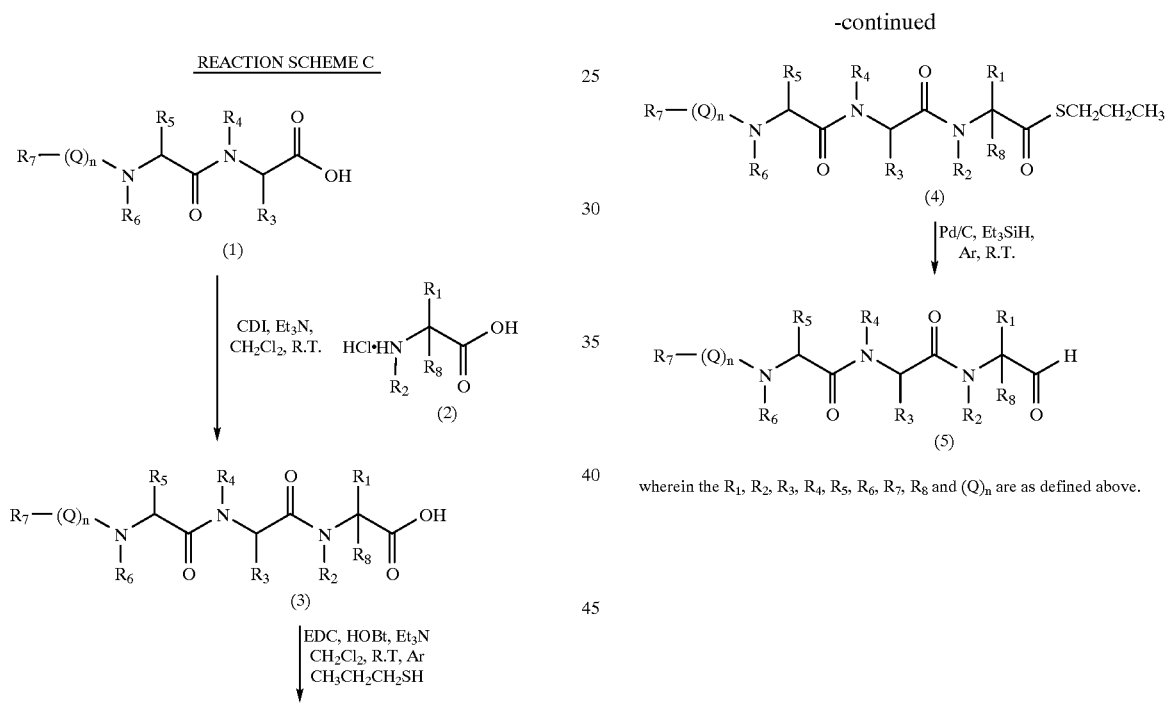
wherein the $R_1$, $R_2$, $R_3$, $R_4$, $R_5$, $R_6$, $R_7$, $R_8$ and $(Q)_n$ are as defined above.

REACTION SCHEME D
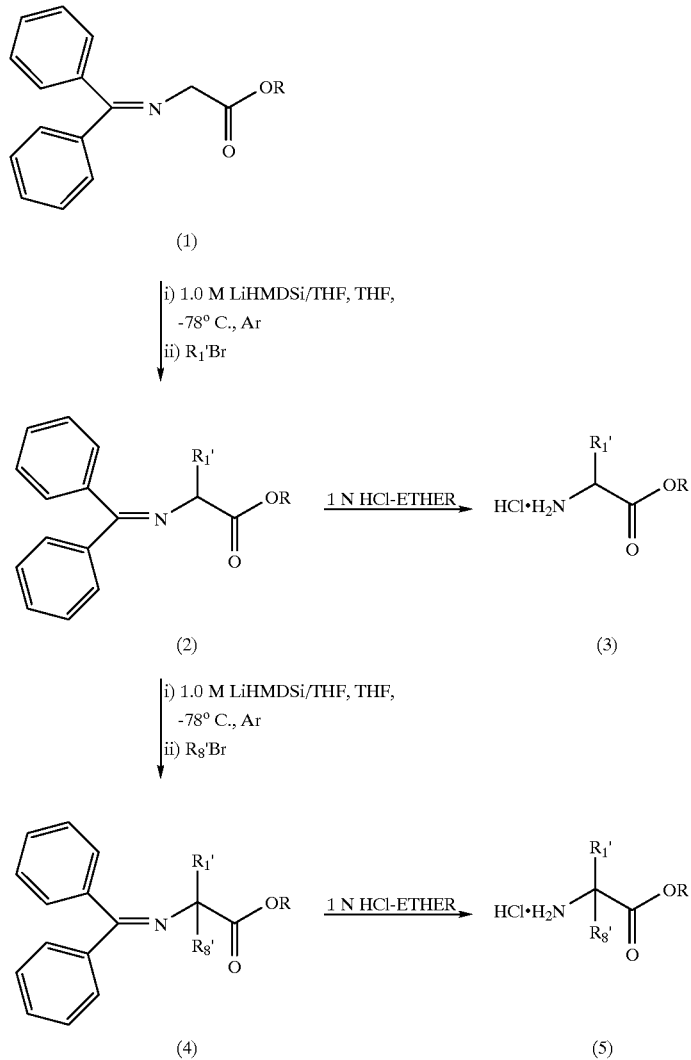
wherein $R_1'$ is a moiety of $R_1$ which is not a side chain of natural α- amino acid, $R_8'$ is $C_{1-4}$ alkyl, R is methyl or ethyl.

REACTION SCHEME E
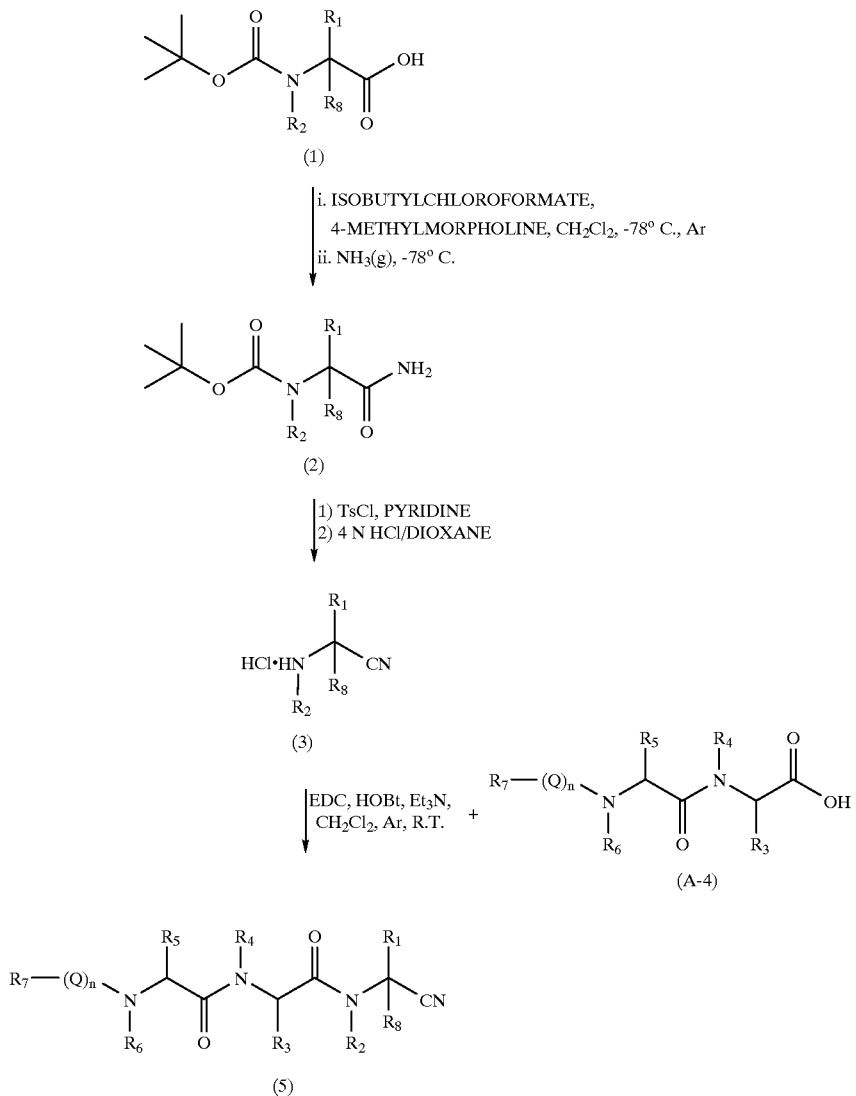
wherein the $R_1$, $R_2$, $R_3$, $R_4$, $R_5$, $R_6$, $R_7$, $R_8$ and $(Q)_n$ are as defined above.

REACTION SCHEME F
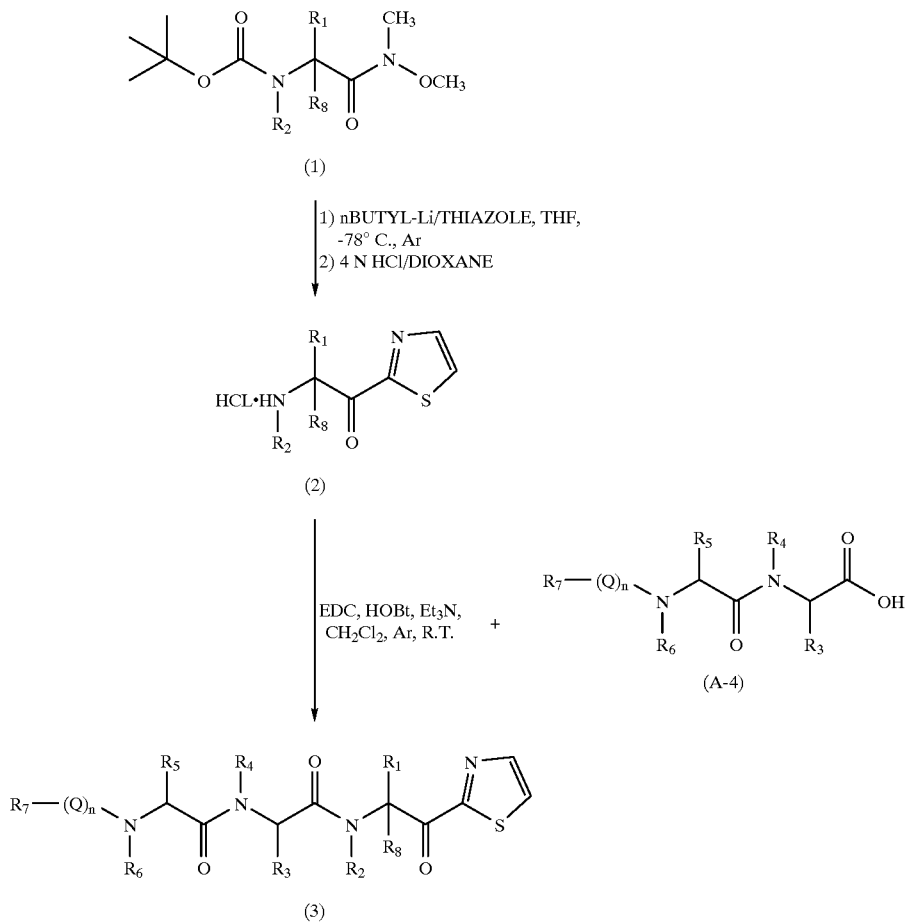
wherein the $R_1$, $R_2$, $R_3$, $R_4$, $R_5$, $R_6$, $R_7$, $R_8$ and $(Q)_n$ are as defined above.
REACTION SCHEME G
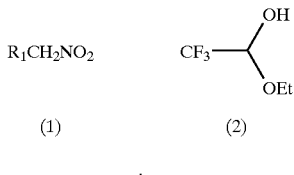

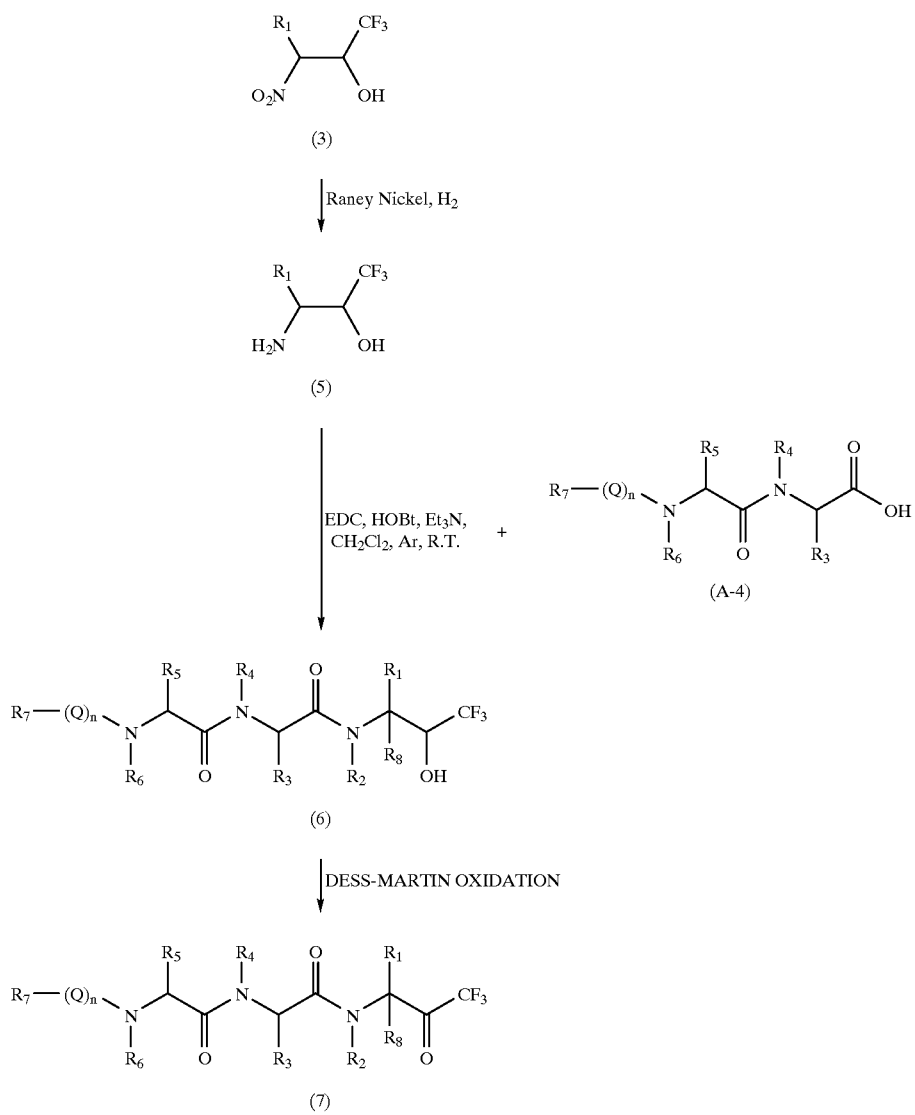
wherein the $R_1$, $R_2$, $R_3$, $R_4$, $R_5$, $R_6$, $R_7$, $R_8$ and $(Q)_n$ are as defined above.

REACTION SCHEME H
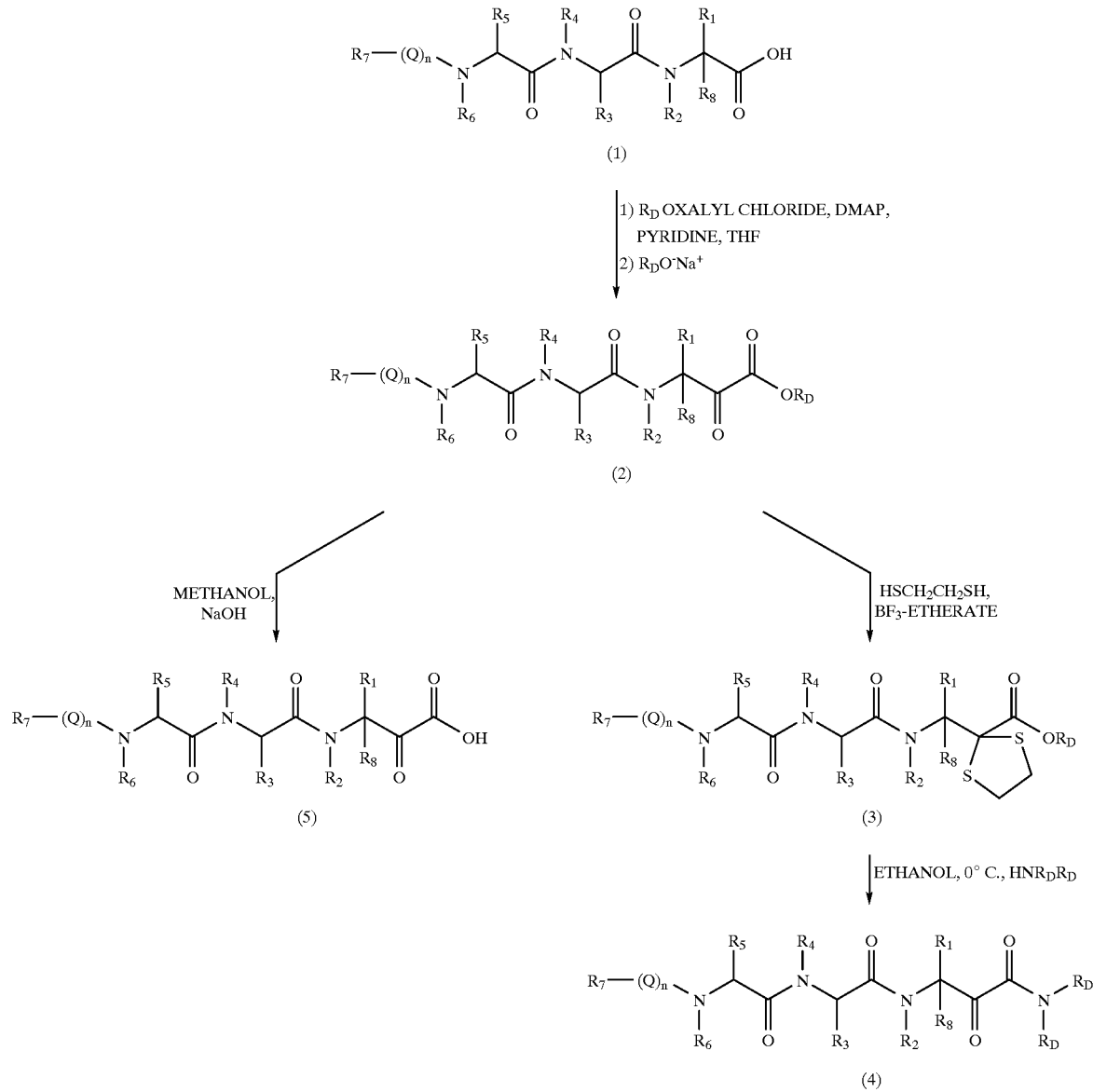
wherein the $R_1$, $R_2$, $R_3$, $R_4$, $R_5$, $R_6$, $R_7$, $R_8$ and $(Q)_n$ are as defined above.
wherein $R_D$ is hydrogen, methyl, ethyl or benzyl.

REACTION SCHEME I
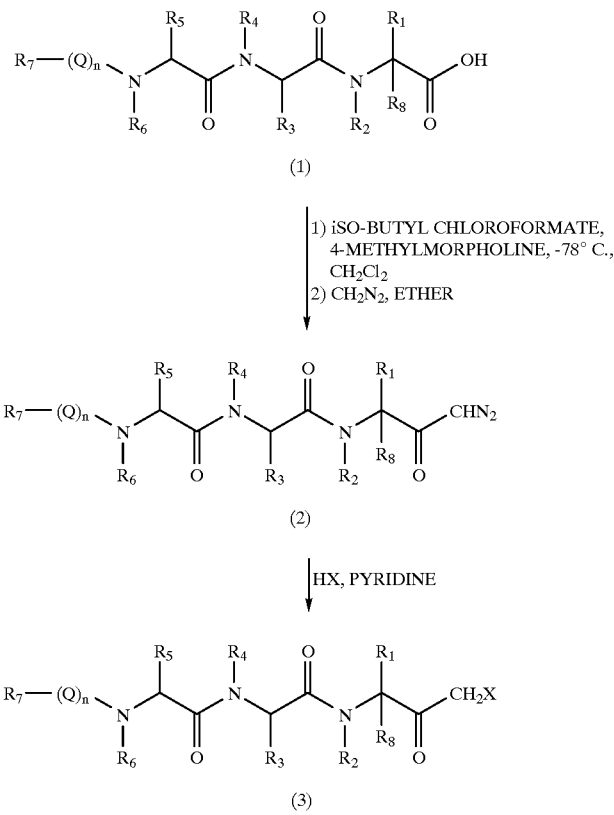
wherein the $R_1$, $R_2$, $R_3$, $R_4$, $R_5$, $R_6$, $R_7$, $R_8$ and $(Q)_n$ are as defined above.
wherein X is F, Cl or Br.

REACTION SCHEME J
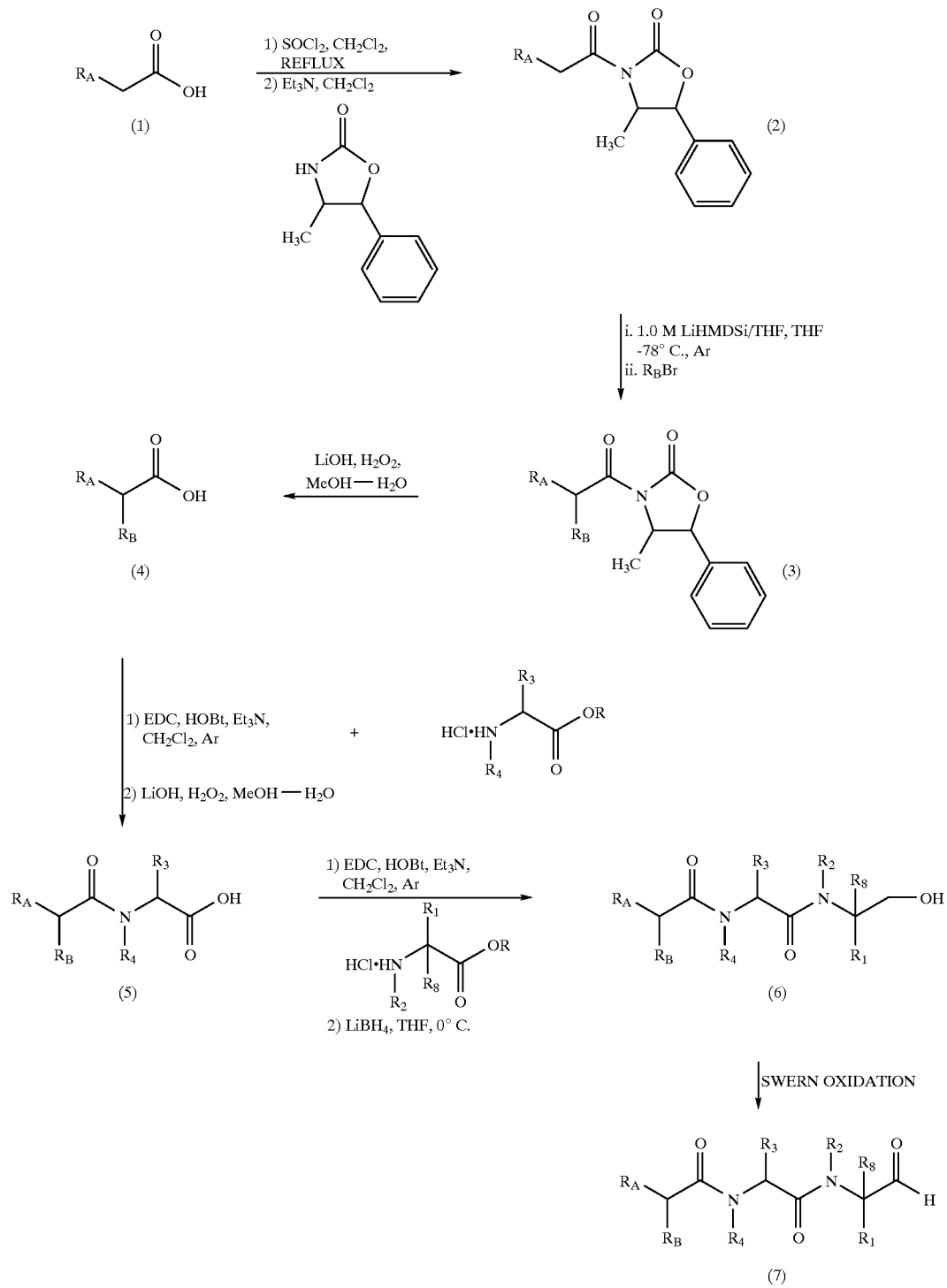
wherein the $R_1$, $R_2$, $R_3$, $R_4$, $R_8$, $R_A$ and $R_B$ are as defined above.

REACTION SCHEME L
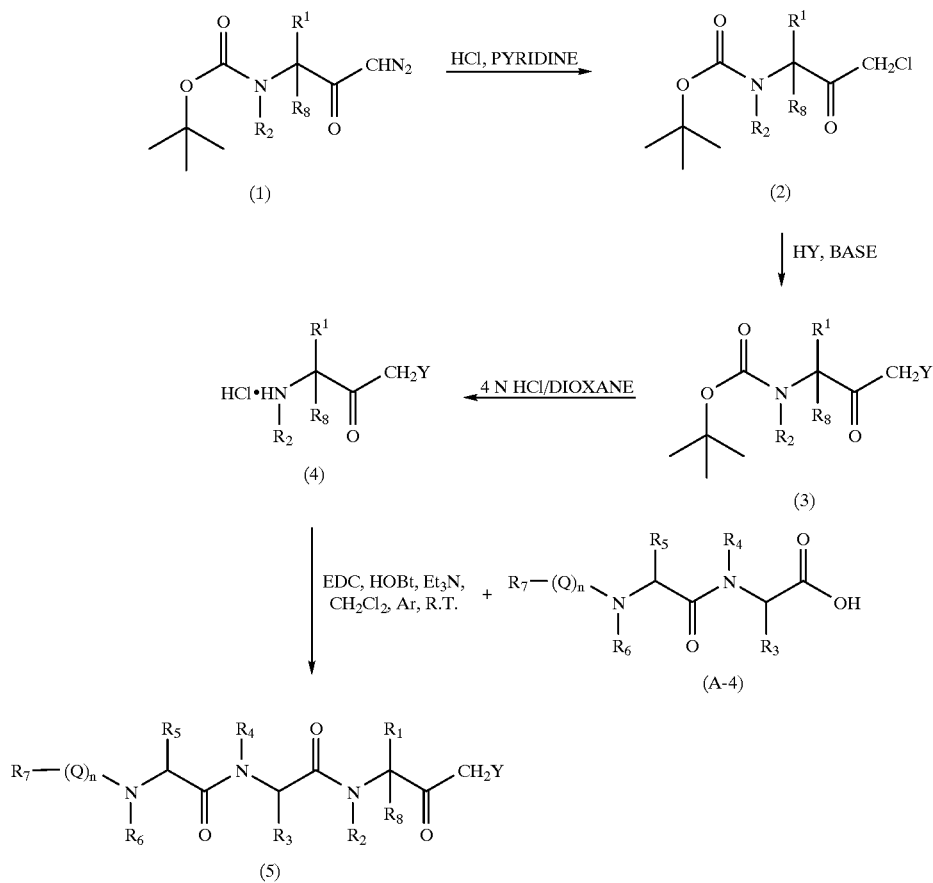
wherein Y is $OR_D$, $SR_D$, $NR_DR_D$ or a 5-6 ring atomed heterocycle aryl having at least one ring atom being O, S or N, and $R_1$, $R_2$, $R_3$, $R_4$, $R_5$, $R_6$, $R_7$, $R_8$ and $(Q)_n$ are as previously defined.

REACTION SCHEME M
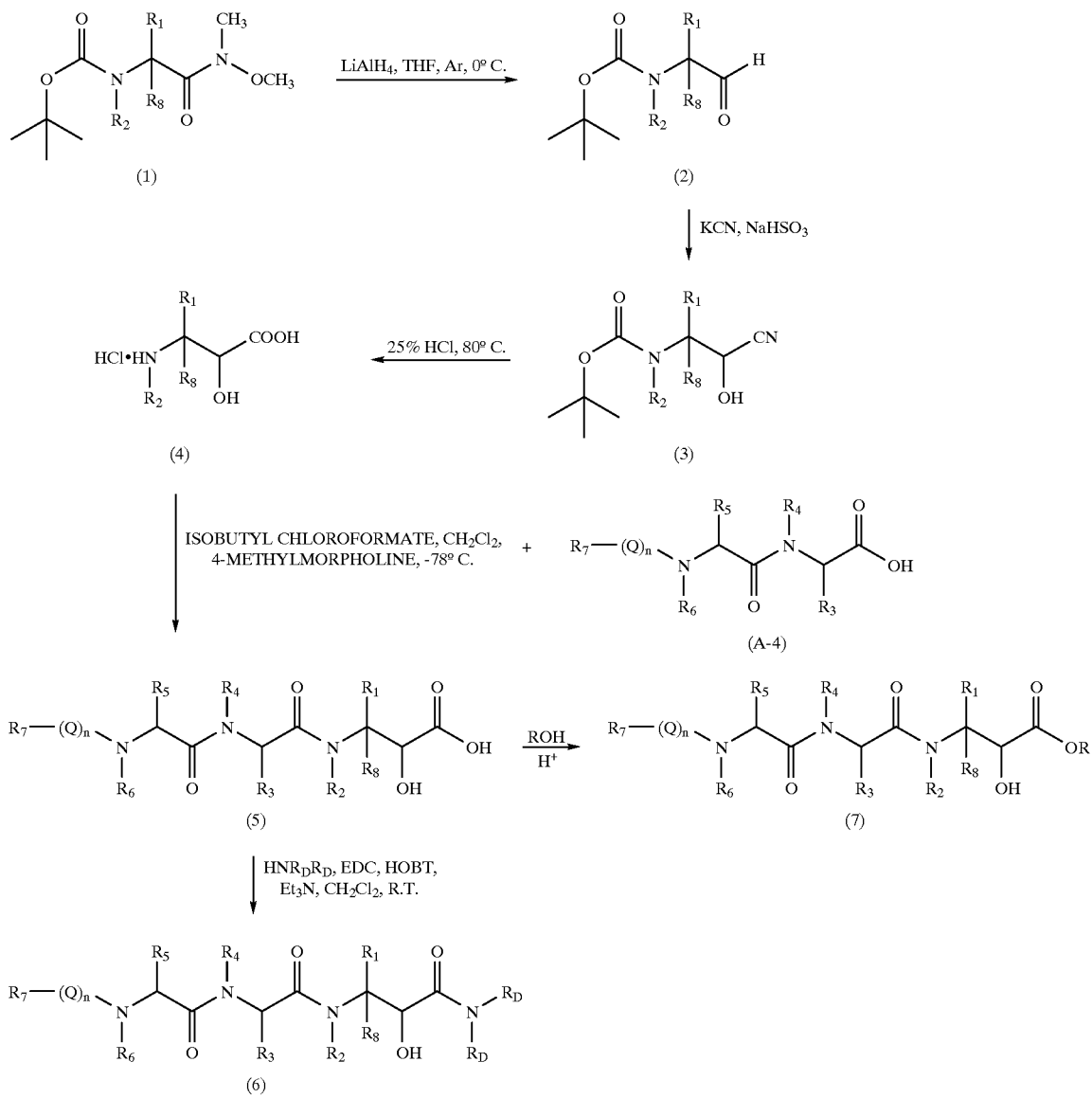
wherein the $R_1$, $R_2$, $R_3$, $R_4$, $R_5$, $R_6$, $R_7$, $R_8$ and $(Q)_n$ are as defined above.
wherein $R_D$ is $C_{1-6}$ alkyl, phenyl, benzyl or hydrogen.
ALTERNATIVELY
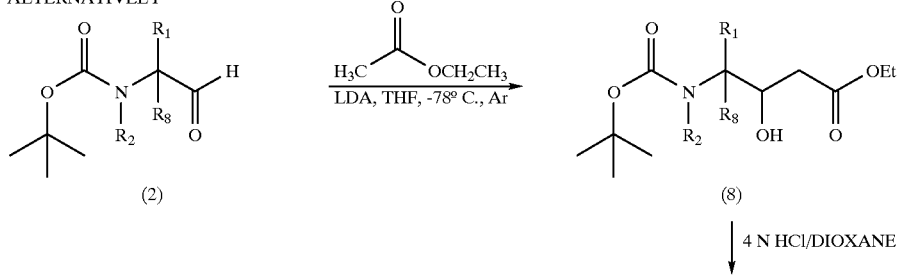

REACTION SCHEME N

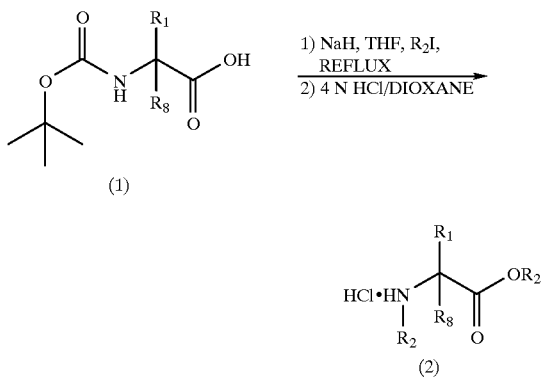

wherein the $R_1$, $R_2$, and $R_8$ are as defined above.

Alternative methods for preparing aldehydes are depicted in Reaction Schemes A, B and C. In Scheme A, the process is initiated by coupling the protected amino acid (1) with the N-methyl-N-methoxyamine hydrochloride (2) utilizing EDC (1-(3-dimethylaminopropyl)-3-ethylcarbodiimide as its HCl salt) in the presence of hydroxybenzyl triazole (HOBt) and triethylamine ($Et_3N$); the reaction is conducted in $CH_2Cl_2$ at room temperature under anhydrous conditions. Upon completion of the coupling reaction, the amine-protecting group is removed by reaction with 4 N HCl in dioxane to yield compound (3). The resulting N-methyl-N-methoxyamide derivatives (sometimes referred to as a Weinreb amide) are coupled to a N-protected dipeptide (4) to produce the analogous N-methyl-N-methoxyamide intermediates (5) which are reduced to the desired aldehydes using standard reduction conditions, e.g., by the use of lithium aluminum hydride ($LiAlH_4$) in tetrahydrofuran (THF) at about 0° C. in an inert atmosphere (Ar or $N_2$) under anhydrous conditions. After the reaction is complete, about 30 min, the reaction is quenched by the addition of, for example, 10% potassium hydrogen sulfate and then water.

In Reaction Scheme B, the intermediates (A-4; compound 4 prepared in Scheme A) are coupled with an ester (derived by a standard Fischer esterification of (1)) and the resulting esters (B-3) are reduced to their corresponding alcohols (B-4) using lithium borohydride in THF at temperatures of about 0° C. to room temperature; the reduction, of course, being conducted under anhydrous conditions in an inert atmosphere. The resulting alcohols (B-4) are oxidized to the desired aldehydes using the well-known Swern oxidation procedure.

In Scheme C, the esters (1) are subjected to mild hydrolysis using LiOH and hydrogen peroxide in a methanol-water solvent according to known conditions. Using the same coupling procedure as described in Scheme A1, the resulting amino acids are coupled with propane sulfide to produce the thioesters (2) which are reduced to their corresponding aldehyde by using Pd on carbon with triethylsilane under anhydrous conditions at room temperature under an inert atmosphere.

Reaction Scheme D illustrates the preparation of precursor reactants which are amendable to substitutions on the α-carbon atom; these substituents not necessarily being residues of naturally occurring α-amino acids. In this scheme, N-(diphenylmethylene)glycine ethyl ester (1) is treated with lithium bis(trimethylsilyl)amide wherein the reaction is effected in THF under an inert atmosphere at temperatures of about −78° C. and the in situ generated base is reacted with the appropriate alkyl halide to effect a nucleophilic displacement. The so-alkylated intermediates (2) and (4) are subjected to hydrolysisto produce the amines (3) and (5) which are available for appropriate use in the construction of the desired dipeptides and tripeptides wherein $R_1$, $R_3$ or $R_5$ are side chains other than that of a naturally occurring α-amino acid. Similar such process may be useful in preparing compounds in which $R_2$, $R_4$ or $R_6$ is an alkylated product.

Reaction Scheme E illustrates the preparation of the $P_1$ moiety wherein X is nitrile. The synthesis is initiated by reacting an N-protected amino acid with iso-butyl chloroformate in the presence of 4-methylmorpholine at −78° C. under an inert atmosphere and the resulting mixed anhydride derivatives are treated with ammonia gas at −78° C. to form the corresponding amides (2). The amide is converted to its nitrile by dehydration with tosyl chloride in pyridine followed by the removal of the Boc protecting group by hydrolysis with 4 N HCl in dioxane. Following their preparation, the $P_1$ moieties are coupled with the appropriate $P_2P_3$ moiety (A-4), or with the appropriate $P_2$ moiety (J-5) to produce the nitriles of E-5 [or in the case of coupling with the $P_2$ moiety of J-5, the corresponding nitrile analogues to the aldehydes (J-7)].

Reaction Scheme F illustrates the preparation of compounds of a $P_1$ moiety wherein X is a C(O)W, defined as above, $C_{1-6}$ alkyl or aralkyl. In effecting the preparations, the N-methyl-N-methoxyamide derivative (1) is treated with a lithiothiazole nucleophile generated in situ to produce a ketothiazole which is deprotected by hydrolysis with 4 N HCl in dioxane to obtain compounds (2) which are then coupled to the appropriate $P_2P_3$ moieties to obtain the derivatives of compound (3) or with the appropriate $P_2$ moieties (i.e., $(R_A)CH(R_B)$—$C(O)N(R_4)$—$CH_2(R_3)C(O)$OH) to obtain the desired dipeptides. Of course, the lithio derivative of thiazole may be replaced with litho derivatives of other aryl, aralkyl and alkyl moieties and by following substantially the same procedures, the corresponding di- and tri-peptides may be obtained.

Reaction Scheme G illustrates the preparation of compounds of formulae I and II wherein the X moiety is a haloketone. The reaction is initiated by reacting an $R_1$-substituted nitromethane with a trifluoromethyl acetal (2) in DMF in the presence of potassium carbonate at about 60° C. to yield a 1,1,1-trifluoro-2-hydroxy-3-nitro derivative (3) which are reduced with $H_2$ in the presence of Raney Nickel to yield the corresponding amines (4). By appropriate coupling, the alcohols of (6) may be produced which would then be subjected to Dess-Martin oxidation to produce the desired $CF_3$ analogues (7). By use of mono- and di-fluoromethyl analogues of formula (2) and by following substantially the same procedures, there are produced the corresponding —$CH_2F$ and —$CHF_2$ ketone analogues.

Reaction Scheme H illustrates the preparation of compounds of formulae I and II wherein the X represents an α-ketoester or α-ketoamide (C(O)C(O)$OR_D$ or C(O)C(O)$NR_DR_D$, respectively). In this process, the peptides are subjected to a modified Dakin West reaction to generate an enol ester which is subjected to a basic hydrolysis to obtain the α-keto esters (2). To transform the α-keto esters to their corresponding amides, the ketone is protected by a ketal formation by reaction with $HSCH_2CH_2SH$ in the presence of a $BF_3$ etherate. Treatment with ethanol at 0° C. in the presence of the appropriate amines forms the amide moiety and deprotects the ketal to form the α-keto amide (4).

Alternatively, hydrolysis of intermediate (2) produces the α-keto acid (5).

Reaction Scheme I illustrates the preparation of compounds of formulae I and II wherein the X moiety is a diazomethane which may be converted to a halomethyl ketone. In this process the amine protected peptides are subjected to reaction with iso-butyl chloroformate in the presence of 4-methylmorpholine in $CH_2Cl_2$ at −78° C. The mixed anhydride derivatives are reacted with diazomethane according to standard procedures well known in the art. If desired, the diazoketones of formulae II may be treated with the appropriate acid (e.g., HF, HCl, HBr), in pyridine to afford the desired ketohalomethyl derivatives.

Reaction Scheme J illustrates the preparation of compounds of formulae I and II wherein the amino terminus of the peptide is modified to produce compounds embraced within the scope of the $[R_A(R_B)-CH-(Q)_n-]$ of formulae II as well as compounds which fall within the scope of $R_7-(Q)_n-$ of fomulae I wherein $(Q)_n$ is C(O). The scheme is initiated by the conversion of the acid (1) to its acid chloride. Treatment of the acid chloride with the appropriate chiral auxiliary (e.g., 4S,5R-(−)-4-methyl-5-phenyl-oxazolidinone) in the presence of triethylamine in $CH_2Cl_2$ produces the imides (2). These imides are treated with lithium bis(trimethylsilyl)amide in tetrahydrofuran at −78° C. (initially) and the resulting activated moiety, generated in situ, is subjected to a stereoselective alkylation using a haloelectrophile. The alkylation is completed as the mixture warms to room temperature to produce compounds (3) as pure enantiomers. Hydrolysis with lithium hydroxide in hydrogen peroxide produces the acids (4) which are coupled to an amino acid (in its ester form) using the described EDC, HOBt, $Et_3N$ coupling process, followed by hydrolysis of the ester. The hydrolyzed amino acid is subjected to another coupling reaction with an amino acid (in its ester form), and the ester of the resulting dipeptide is reduced with lithium borohydride to its corresponding alcohol (6). The alcohol is converted to its aldehyde using the Swern oxidation procedure. Of course, by selecting the appropriate chiral auxiliary and substantially following the outlined procedure, other stereospecific enantiomers may be produced.

Reaction Scheme K illustrates the formation of a dipeptide wherein $R_B$ may represent an aryloxy, aralkoxy or an alkoxy in an enantiomeric pure isomer. The reaction is initiated by a two step process wherein (a) compound (1) is hydrodeaminated by treatment with $NaNO_2$ in HCl and (b) an esterification of the acid with an alkyl halide in the presence of DMF and cesium carbonate to produce compounds (2). These are treated with a 2,2,2-trichloroacetimate derivatives in the presence of trifluoromethanesulfonic acid in $CH_2Cl_2$ to obtain the desired ester and the ester moiety is hydrolyzed with lithium hydroxide in peroxide and a methanol-water solvent to produce the enantiomers of formula (3). The isomers are coupled with the appropriate $P_2P_1$ moieties (as esters), the resulting esters (5) are reduced to their corresponding alcohols which are then oxidized to the corresponding aldehydes (6).

Reaction Scheme L illustrates the preparation of compounds of formulae I and II wherein the X is defined by the moiety $C(O)CH_2Y$. The N-protected diazoketone derivatives of compound (1) are subjected to an addition reaction with an hydrohalic acid, preferably HCl, in pyridine to produce halomethyl derivatives (2), which are subjected to a nucleophilic displacement reaction using an activated anion of the desired Y moiety, (e.g., $^-Y$), to afford compounds (3). Standard hydrolysis reactions remove the N-protecting group followed by the usual coupling procedures with the desired $P_2P_3$ moieties (e.g., compounds A-4) to produce the desired compounds (5).

Reaction Scheme M illustrates the preparation of compounds of formulae I and II wherein the X is defined by the moieties (a) $-CH(OH)-C(O)-NR_DR_D$ and (b) $-CH(OH)-C(O)OR_D$. The process conveniently starts with the obtention of the aldehyde (2) by reducing the N-methyl-N-methoxy amide derivative (1), followed by preparation of the cyanohydrin (3) which is hydrolyzed to its free acid (4) using standard and well known reaction techniques. Coupling of the desired dipeptides (i.e., the $P_2P_3$ moiety) to the acid (4) is effected by the use of an activated iso-butyl chloroformate in the presence of 4-methylmorpholine at −78° C. in an inert atmosphere under anhydrous conditions to afford the acid (5). The acids (5) may be esterified to its corresponding ester or may be coupled with an amine ($NR_DR_D$) to produce the desired amides (6). Of course, using substantially the same procedure but replacing the $P_2P_3$ moieties of formula A-4 with the appropriate $P_2$ moiety, analogous dipeptides may be prepared.

Alternatively, compounds (2) may be transformed to their N-protected (preferably a Boc group) alkyl ester by reaction with ethylacetate in the presence of LDA to produce compounds (8) which are hydrolyzed with 4 N HCl in dioxane to remove the protecting group to produce the corresponding β-hydroxy ethyl esters (9). These esters are then coupled with compounds (A-4) and the resulting compounds are hydrolyzed to their,β-hydroxy acids or they may be coupled to form their β-hydroxyamides of compounds (11).

Reaction Scheme N illustrates the process by which compounds of formulae I and II wherein the $R_2$, $R_4$, or $R_6$ represent an $R_D$ moiety other than H. In essence, the procedure utilizes standard N-protection, N-alkylation-esterfication and de-protection procedures such as those exemplified in the depicted schemes. Of course, although the reaction scheme depicts N-alkylation at the projected $P_1$ moiety, any of the $P_2$ and $P_3$ moieties may be similarly N-alkylated by appropriate selection of the starting materials followed by the coupling procedures required to construct the desired peptides of formulae I and II.

Throughout the above presentation of the methods useful for preparing the compounds herein, particularly as it relates to the foregoing reaction schemes, the full embodiment of the entire scope of the compounds (as defined in formulae I and II) was not depicted within all of the structures illustrated for each of the reactants and end-products. The state of the art is such that one of skill in the art would be able to extend these specific illustrations to embrace the implied generic teachings by the use of analogy reasoning to prepare the desired compounds embraced within the scope of formulae I and II. For example, in Reaction Scheme A it is to be noted that the final compounds (i.e., compounds (6) of that reaction scheme) are tripeptides. It can be seen that by substituting the reactant (4) with the appropriate α-amino acid, and by following the teachings herein, dipeptides would result. Similarly one of skill in the art could utilize the final product of Reaction Scheme D in preparing any of the compounds of formulae I and II bearing the $R_1$ side chain functionality, which is other than a residue of a naturally occurring α-amino acid. Similarly, in Reaction Scheme F, the preparation of a thiazole derivative is achieved by coupling the N-methoxy-N-methylamide derivative of a precursor for preparing a depicted tripeptide (3). A dipeptide bearing a thiazole derivative could be prepared by the application of the analogy reasoning possessed by a person of skill in the art. Similarly, lithio derivative of another heterocycle in which X is C(O)aryl and the aryl moiety is other than a thiazole embraced within the scope of the compounds herein could be prepared.

Thus, the scope of those compounds preparable by the methods of the foregoing reaction schemes is not limited to the specific compounds depicted but rather to those compounds defined by formulae I and II using the teachings already available in the art and which are exemplified to illustrate such teachings.

2. Procedures to effect the reaction schemes

The construction of the tri- and dipeptide analogs of Formulae I and II may be effected using procedures and techniques well known in the art and described herein. Many of the necessary starting materials and the reactants utilized are known and may also be commercially available. In those instances in which they are not generally available, they may readily be generated by analogous use of known chemical processes and techniques readily available in the scientific and patent literature or as described herein.

As the reaction schemes depicted herein (Schemes A–N) extensively utilize coupling and oxidation procedures, the following elaborates a variety of the procedures that may be functional alternatives to those specifically mentioned within the depicted schemes.

As a preferred oxidation procedure, the Swern oxidation is effected by reacting 2 to 10 equivalents of dimethyl sulfoxide (DMSO) with about 1 to 6 equivalents of trifluoroacetic anhydride [$(CF_3CO)_2$] or oxalyl chloride [$(COCl)_2$]. The reactants are dissolved in an inert solvent, e.g., methylene chloride ($CH_2Cl_2$), the reactor is under an inert atmosphere under anhydrous conditions at temperatures of about −80° C. to −50° C. to form an in situ sulfonium adduct to which is added about 1 equivalent of the alcohols (e.g., B-4). Preferably, the alcohols are dissolved in an inert solvent, e.g., $CH_2Cl_2$ or minimum amounts of DMSO, and the reaction mixture is allowed to warm to about −50° C. (for about 10–20 minutes) and then the reaction is completed by adding 3 to 10 equivalents of a tertiary amine, e.g., triethylamine, N-methyl morpholine, etc. Following oxidation, the desired intermediates are isolated and are ready for the next step in the reaction sequence.

A modified Jones oxidation procedure may conveniently be effected by reacting the alcohols with pyridinium dichromate by contacting the reactants in a water-trapping sieve powder, (e.g., a grounded 3 Angström molecular sieve) in the presence of glacial acetic acid at about 5° C. to 50° C., preferably at room temperature.

Alternatively, 1 to 5 equivalents of a chromic anhydride-pyridine complex [i.e., a Sarett reagent prepared in situ (see, e.g., Fieser and Fieser "Reagents for Organic Synthesis" Vol. 1, pp. 145 and Sarett, et al., *J.A.C.S.* 25, 422 (1953))] that is prepared in situ in an inert solvent (e.g., $CH_2Cl_2$) in an inert atmosphere under anhydrous conditions at about 0° C. to 50° C. to which complex is added 1 equivalent of the alcohols allowing the reactants to interact for about 1 to 15 hours, followed by the isolation of the desired product.

Another alternative process for the converting of alcohols to the desired ketones is an oxidation reaction that employs periodane [i.e., 1,1,1-triacetoxy-1,1-dihydro, 1,2-benzoxidol 3-(1-H)-one (see Dess Martin, *J. Org. Chem.* 48, 4155, (1983))]. This oxidation is effected by contacting 1 equivalent of the alcohols with 1 to 5 equivalents of periodane (preferably 1.5 equivalents) in suspension in an inert solvent (e.g., $CH_2Cl_2$) under an inert atmosphere (preferably nitrogen) under anhydrous conditions at about 0° C. to 50° C. (preferably room temperature), and allowing the reactants to interact for about 1 to 48 hours.

A solid phase sequential coupling procedure can be performed using established methods such as use of an automated peptide synthesizer. In this procedure, an amino protected amino acid is bound to a resin support at its carboxyl terminus, the protected amine is deprotected where the peptide linkage is desired, the amino group neutralized with a base and the next amino protected amino acid in the desired sequence is coupled in a peptide linkage. The deprotection, neutralization and coupling steps are repeated until the desired peptide is synthesized. The compounds provided herein are thus synthesized from their carboxyl terminal end to their amino terminal end. The amino protected amino acid can be a conventional amino acid, a derivative or isomer thereof, or a spacer group. The resin support employed can be any suitable resin conventionally employed in the art for the solid phase preparation of polypeptides. The preferred resin is polystyrene which has been cross-linked with from about 0.5 to about 3% divinyl benzene, which has been either benzhydrylamidated, chloromethylated or hydroxymethylated to provide sites for amide or ester formation with the initially introduced amino protected amino acid.

An example of a hydroxymethyl resin is described by Bodansky et al. [*Chem. Ind.* (London) 38, 1597–98 (1966)]. The preparation of chloromethyl and benzhydrylamine resins are described by Stewart et al. ["Solid Phase Peptide Synthesis," 2nd Edition, Pierce Chemical Co., Rockford, Ill. (1984). Chapter 2, pp. 54–55]. Many of these resins are available commercially. In general, the amino protected amino acid which is desired on the carboxyl-terminal end of the peptide is bound to the resin using standard procedures and practices as are well known and appreciated in the art. For example, the amino protected amino acid can be bound to the resin by the procedure of Gisin [*Helv. Chem. Acta*, 56, 1476 (1973)]. When it is desired to use a resin containing a benzhydrylamine moiety as the resin binding site an amino protected amino acid is coupled to the resin through an amide linkage between it α-carboxylic acid and the amino moiety of the resin. The coupling is effected using standard coupling procedures as described below. Many resin-bound amino acids are available commercially.

The α-amino protecting group employed with each amino acid introduced into the polypeptide sequence may be any such protecting group known in the art. Among the classes of amino protecting groups contemplated are: (1) acyl type protecting groups such as formyl, trifluoroacetyl, phthalyl, p-toluenesulfonyl (tosyl), benzenesulfonyl, nitrophenylsulfonyl, tritylsulfonyl, o-nitrophenoxyacetyl, and α-chlorobutryl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α,α-dimethyl-3,5-dimethoxybenzyloxycarbonyl, and benzhydryloxycarbonyl; (3) aliphatic urethane protecting groups such as t-butyloxycarbonyl (Boc), diisopropylmethoxycarbonyl, isopropyloxycarbonyl, ethoxycarbonyl, and allyloxycarbonyl; (4) cycloalkyl urethane type protecting groups such as cyclopentyloxycarbonyl,adamantyloxycarbonyl, andcyclohexyloxycarbonyl; (5) thiourethanetype protecting groups such as phenylthiocarbonyl; (6) alkyl type protecting groups such as triphenylmethyl (trityl) and benzyl (Bn); (7) trialkylsilane protecting groups such as trimethylsilane, 4-[-(4-chlorophenyl) sulfonylaminocarbonyl] phenyl carbonyl, and 4-[-(4-bromophenyl) sulfonylaminocarbonyl] phenyl carbonyl. The preferred α-amino protecting group is t-butyloxycarbonyl (Boc); its use as an α-amino protecting group for amino acids is well known to those of skill in the art ([see, e., by Bodansky et al. in "The Practice of Peptide Synthesis," Springer-Verlag, Berlin (1984), p.20].

Following the coupling of the amino protected amino acid to the resin support, the α-amino protecting group may be removed using any suitable procedure such as by using trifluoroacetic acid, trifluoroacetic acid in $CH_2Cl_2$, or HCl in dioxane. The deprotection is carried out at a temperature of between 0° C. and room temperature. Other standard cleaving reagents may be used for removal of specific amino protecting groups under conditions well known and appreciated in the art.

After removal and neutralization of the α-amino protecting group, the next desired amino-protected amino acid is coupled through a peptide linkage. This deprotection, neutralization and coupling procedure is repeated until a peptide of the desired sequence is obtained. Alternatively, multiple amino acid groups may be coupled by the solution method prior to coupling with the resin supported amino acid sequence.

The selection and use of an appropriate coupling reagent is within the skill of the skilled artisan. Particularly suitable coupling reagents where the amino acid to be added is Gln, Asn, or Arg include N,N-dicyclohexylcarbodiimide and 1-hydroxybenzotriazole. The use of these reagents prevents nitrile and lactam formation. Other coupling agents are (1) other carbodiimides (e.g., N-ethyl-N'-(γ-dimethylaminopropylcarbodiimide); (2) ketenimines; (3) isoxazolium salts (e.g., N-ethyl-5-phenylisoxazolium-3-sulfonate); (4) monocyclic nitrogen-containing heterocyclic amides of aromatic character containing one through four nitrogens in the ring such as imidazolides, pyrazolides, and 1,2,4-triazolides (specific heterocyclic amides that are useful include N,N-carbonyidiimidazole and N,N-carbonyl-di-1,2,4-triazole); (5) alkoxylated acetylene (e.g., ethoxyacetylene); (6) reagents which form a mixed anhydride with the carboxyl moiety of the amino acid (e.g., ethyl chloroformate and iso-butyl chloroformate) or the symmetrical anhydride of the amino acid to be coupled (e.g., Boc-Ala-O-Ala-Boc); (7) nitrogen-containing heterocyclic compounds having a hydroxyl group on one ring nitrogen (e.g., N-hydroxyphthalimide, N-hydroxysuccinimide, and 1-hydroxybenzotriazole). Other activating reagents and their use in peptide coupling are described by Kapoor [*J. Pharm. Sci.*, 59, 1–27 (1970)]. Use of the symmetrical anhydride as the coupling agent is the generally preferred amino acid coupling method herein.

The preferred coupling method for Gln, Asn and Arg is to react the protected amino acid, or derivatives or isomers thereof, with N,N-dicyclohexylcarbodiimide and 1-hydroxybenzotriazole (1:1) in N,N-dimethylformamide (DMF) in the presence of the resin or resin-bound amino acid or peptide. The preferred coupling method for other amino acids involves reacting the protected amino acid, or derivative or isomer thereof, with N,N-dicyclohexylcarbodiimide in $CH_2Cl_2$ to form the symmetrical anhydride. The symmetrical anhydride is then introduced into the solid phase reactor containing the resin or resin-bound amino acid or peptide, and the coupling is carried out in a medium of DMF, or $CH_2Cl_2$, or DMF: $CH_2Cl_2$ (1:1). A medium of DMF is preferred. The success of the coupling reaction at each stage of the synthesis is monitored by a ninhydrin test as described by Kaiser et al. [*Analyt. Biochem.* 34, 595 (1970)]. In cases where incomplete coupling occurs, the coupling procedure is repeated. If the coupling is still incomplete, the deprotected amine is capped with a suitable capping reagent to prevent its continued synthesis. Suitable capping reagents and the use thereof are well known and appreciated in the art. Examples of suitable capping reagents are acetic anhydride and acetylimidazole as described by Stewart et al. ["Solid Phase Peptide Synthesis," 2nd Ed., Pierce Chemical Co., Rockford, Ill. (1984), Chapter 2, p.73].

After the desired amino acid sequence has been obtained, the peptide is cleaved from the resin. This can be effected by procedures which are well known and appreciated in the art, such as by hydrolysis of the ester or amide linkage to the resin. It is preferred to cleave the peptide from the benzhydrylamine resin with a solution of dimethyl sulfide, p-cresol, thiocresol, or anisole in anhydrous hydrogen fluoride. The cleavage reaction is preferably carried out at temperatures between about 0° C. and about room temperature, and is allowed to continue preferably from between about 5 minutes to about 5 hours.

As is known in the art of solid phase peptide synthesis, many of the amino acids bear side chain functionalities requiring protection during the preparation of the peptide. The selection and use of an appropriate protecting group for these side chain functionalities is within the ability of those skilled in the art and will depend upon the amino acid to be protected and the presence of other protected amino acid residues in the peptide. The selection of such a side chain protection group is critical in that it must not be removed during the deprotection and coupling steps of the synthesis. For example, when Boc is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bn), or t-butylsulfonyl moieties can be used to protect the sulfide-containing side chains of amino acids such as cysteine, homocysteine, penicillamine and the like or derivatives thereof; benzyl or cyclohexyl ester moieties can be used to protect carboxylic acid side chains of amino acids such as Asp, Glu; a benzyl ether can be used to protect the hydroxyl-containing side chains of amino acids such as Ser and Thr; and a 2-bromocarbobenzoxy (2Br-Cbz) moiety can be used to protect the hydroxyl-containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin.

The compounds are then isolated and purified by standard techniques. The desired amino acids, derivatives and isomers thereof can be obtained commercially or can be synthesized according to standard practices and procedures well known in the art.

C. Identification of Preferred Compounds Using Assays That Identify Compounds That Modulate Processing of Amyloid Precursor Protein (APP)

Compounds provided herein modulate the processing of proteins, such as amyloid precursor protein (APP), involved in neurodegenerative diseases. The ability of compounds to modulate processing of APP can be demonstrated in a variety of ways. For example, compounds can be evaluated for the ability to modulate generation of Aβ or α-sAPP.

1. In vitro assays

The compounds provided herein yield a positive result in one or more in vitro assays that assess the effects of test compounds on processing of APP. In particular, in vitro assay systems for identifying such compounds are provided herein. These assays evaluate the effects of a test compound on processing of APP and use cultured human glioblastoma cell lines that have been transfected with DNA encoding either a wild-type 695 amino acid isoform of APP or a mutein of that APP that contains changes (in this case two or three amino acid changes have been made) that appear to make the molecule more susceptible to proteolytic cleavage that results in increased production of Aβ [see, e.g., Mullan et al. (1992) *Nature Genet.* 1:345–347].

In performing these assays, a test compound is added to the culture medium and, after a selected period of time, the culture medium and/or cell lysates are analyzed using immunochemical assays to detect the relative amounts of Aβ, total soluble APP (sAPP), a portion of sAPP designated α-sAPP, and C-terminal fragments of APP. In particular, the culture medium and cell lysates are analyzed by immunoblotting coupled with laser scanning densitometry and ELISAs using several different antibodies. A positive test, occurs when: (1) there is a decrease in the ~4-kDa amyloid β-protein (Aβ) in the medium relative to control cultures (4-kDa assay); and/or (2) the relative amount of total sAPP in the medium increases; and/or (3) there is a decrease in the amount of C-terminal amyloidogenic fragments larger than 9 kDa and smaller than 22 kDa in the cell lysate as a result of differential processing; and/or (4) there is an increase in the amount of α-sAPP in the medium relative to control cultures. Control cultures can be cultures that have not been contacted with the compound. The Aβ assay is done using cells (e.g., HGB 717/Swed) that have been transfected with DNA encoding the mutein APP; the other assays are performed using cells, such as HGB695 cells, that have been transfected with DNA encoding a wild-type APP.

Preferred compounds have activity that is at least 2-fold, preferably 5-fold, most preferably 10-fold greater activity than N-Acetylleucylleucyl-norleucinal [see, e.g., EP 0 504 938 A2; and Sherwood et al. (1993) *Proc. Natl. Acad. Sci. U.S.A.* 90:3353–3357] in at least one, preferably the Aβ assay, of these assays.

2. The amount of α-sAPP and the ratio of α-sAPP to total SAPP in cerebrospinal fluid (CSF) as an indicator of Alzheimer's Disease (AD) and the effectiveness of therapeutic intervention The relative amount of α-sAPP and the ratio of α-sAPP to total sAPP in CSF are shown herein to be useful markers in the detection of neurodegenerative disorders characterized by cerebral deposition of amyloid (e.g., AD) and in monitoring the progression of such disease. Furthermore, assay systems incorporating these markers can be used in monitoring therapeutic intervention of these diseases.

As shown in EXAMPLE 32, the amount of α-sAPP and the ratio of α-sAPP to total sAPP in CSF samples can be used as an indicator of Alzheimer's Disease and other neurodegenerative disorders. For purposes herein, this amount and/or the ratio can also be used to assess the effectiveness of compounds provided herein in treating Alzheimer's Disease and neurodegenerative disorders.

It has been found that patients with suspected Alzheimer's disease (as diagnosed by other indicia, or confirmed by autopsy) have a statistically significant lower ratio of α-sAPP to total sAPP in CSF and also have statistically significant lower levels of α-sAPP. Therefore, by comparison with non-Alzheimer's disease controls or by existence of a ratio lower than a predetermined standard, based, for example, on averages in samples from large numbers of unafflicted individuals, or an amount of α-sAPP lower than a predetermined standard, Alzheimer's disease or, depending upon other indications, another neurodegenerative disease is indicated.

Compounds, such as those provided herein, that alter this ratio or the level of α-sAPP closer to that of individuals who do not have a neurodegenerative disorder characterized by the cerebral deposition of amyloid are considered useful for treating these disorders.

3. In vivo assays

The ability of compounds to modulate processing of APP can also be evaulated in vivo [see, e.g., Kowall et al. (1991) *Proc. Natl. Acad. Sci. U.S.A.* 88:7247–7251]. Compounds can be administered through a canula implanted in the cranium of a rat or other suitable test animal [see, e.g., Lamb et al. (1993) *Nature Genet.* 5:22–29; Pearson et al. (1993) *Proc. Natl. Acad. Sci. U.S.A.* 90:10578–10582]. After a predetermined period of administration the rats are sacrificed. The hippocampi are evaluated in immunoblot assays or other suitable assays to determine the relative level of α-sAPP and C-terminal fragments of APP compared to untreated control animals. Compounds that result in relative increases in the amount of α-sAPP are selected.

D. Formulation of Pharmaceutical Compositions

Compositions are provided that contain therapeutically effective amounts of the compounds of formulae (I) and (II). The compounds are preferably formulated into suitable pharmaceutical preparations such as tablets, capsules or elixirs, for oral administration or in sterile solutions or suspensions for parenteral administration, as well as transdermal patch preparation. Typically the compounds described above are formulated into pharmaceutical compositions using techniques and procedures well known in the art.

About 10 to 500 mg of a compound or mixture of compounds for Formulae I and II or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained.

To prepare compositions, one or more compounds of formulae (I) and (II) are mixed with a suitable pharmaceutically acceptable carrier. Upon mixing or addition of the compound(s), the resulting mixture may be a solution, suspension, emulsion or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action or have other action. The compounds may be formulated as the sole pharmaceutically active ingredient in the composition or may be combined with other active ingredients.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations of the compounds are effective for delivery of an amount, upon administration, that ameliorates the symptoms of the disorder for which the compounds are administered. Typically, the compositions are formulated for single dosage administration.

The compounds of formulae (I) and (II) may be prepared with carriers that protect them against rapid elimination from the body, such as time release formulations or coatings. Such carriers include controlled release formulations, such as, but not limited to, microencapsulated delivery systems.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compositions can be enclosed in ampules, disposable syringes or multiple or single dose vials made of glass, plastic or other suitable material. Such enclosed compositions can be provided in kits.

The concentration of active compound in the drug composition will depend on absorption, inactivation and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as, but not limited to, gum tragacanth, acacia, corn starch or gelatin; an excipient such as microcrystalline cellulose, starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action.

Solutions or suspensions used for parenteral, intradermal, subcutaneous, or topical application can include any of the following components: a sterile diluent, such as water for injection, saline solution, fixed oil, a naturally occurring vegetable oil like sesame oil, coconut oil, peanut oil, cottonseed oil, etc. or a synthetic fatty vehicle like ethyl oleate or the like, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or multiple dose vials made of glass, plastic or other suitable material. Buffers, preservatives, antioxidants and the like can be incorporated as required.

If administered intravenously, suitable carriers include physiological saline or phosphate buffered saline (PBS), and solutions containing thickening and solubilizing agents, such as glucose, polyethylene glycol, and polypropyleneglycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, may be formulated as 0.01%–100% (weight to volume) isotonic solutions, pH about 5–7, with appropriate salts. The compounds may be formulated as aeorsols for topical application, such as by inhalation [see, e.g., U.S. Pat. Nos. 4,044,126, 4,414,209, and 4,364,923].

Finally, the compounds may be packaged as articles of manufacture containing packaging material, an acceptable composition containing a compound of formulae (I) and (II) provided herein, which is effective for treating the particular disorder, and a label that indicates that the compound or salt thereof is used for treating the disorder.

E. Methods of Use

The compounds for use in the the methods herein have the formulae (I) and (II):

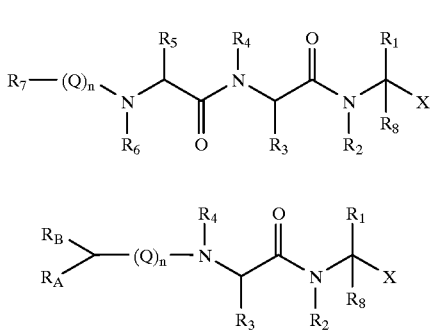

or the hydrates and isosteres, diastereomeric isomers and mixtures thereof, or pharmaceutically acceptable salts thereof in which $R_1$, $R_2$, $R_3$, $R_4$, $R_5$, $R_6$, $R_7$, $R_8$, $R_A$, $R_B$, X, Q and n are selected from among (i), (ii), (iii), (iv), (v), (vi), (vii) or (viii), as described above.

These compounds have pharmacological utility and also utility as reagents. It is recognized in this art that compounds that exhibit activities in assays that assess the ability of the compounds to alter or modulate the activity of proteins associated with the deposition of cerebral amyloid, are pharmacologically useful and potentially therapeutically useful in the treatment of disorders that involve such deposition.

The dose ranges, which can be established empirically, for use in the treatment of disease states will depend upon the etiology, nature, and severity of the disease state as well as such other factors as determined by the attending physcian. The broad range for effective treatment is about 0.01 to 10 mg per kilogram (kg) of body weight per day. The preferred range is about 0.1 to 10 mg/kg of body weight per day.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

Since, it is feasible to indirectly measure the presence of, and over the course of time, to determine the rate of increase of those protein segments believed to be critical to the formation of amyloid plaques located in the brain (see, e.g., U.S. Pat. No. 5,270,165) and the CSF assay provided herein and described above and in the EXAMPLES), dosages can be empirically determined by the physician. As the techniques involve the use of cerebrospinal fluids, such techniques, and other equivalently functioning procedures, will be useful to the attending physician in determining the need to modify the dosage for individual patients.

In treating these disease states, it is sufficient to start treating the patient as soon as the attending physician makes his or herdiagnosis that the patient is suffering from one of these diseases. Thus, although the progress of treatment of the patient may be monitored by the measurements of those biological factors which characterize the diseases, it is not necessary to so-evaluate such characteristics before treatment. Rather it is within the provence of the attending physician to determine when it is in the best interest of the patient to start treatment. Therefore, patients showing increased probabilities of the disease state, (e.g. by carrying known familial genetic markers that increase the probability of the incidence of neurodegenerative diseases as well as the patient's general behavioral characteristics and other indicia of these diseases) can be treated by the methods and with the compositions provided herein.

1. Treatment of neurodegenerative diseases

Amyloid plaques are believed to accompany and/or be involved in the process responsible for the development and progression of certain neurodegenerative disease states. Without being bound by any theory of action, it is believed that the compounds provided herein modulate the generation of amyloidogenic peptides to effectuate a beneficial result. Without any intent to limit -or restrict- the compounds and methods provided herein to any specific mechanism of action for the end-use applications, it is believed that the compounds effectuate a modulation of the processing of the amyloid precursor protein (APP), the progenitor of the deposited amyloidogenic Aβ peptides (39 to 43 amino acid residues) found in senile plaques in the brains of patients diagnosed with, for example, Alzheimer's disease. Thus, the compounds provided herein are useful in the treatment of such neurodegenerative disease states in which such amyloid plaques accumulate or are implicated in the etiology thereof, including, but not limited to: Alzheimer's disease, cognition deficits, Down's Syndrome, Parkinson's disease, cerebral hemorrhage with amyloidosis, dementia pugilistica, head trauma and in the treatment of conditions characterized by a degradation of the neuronal cytoskeleton resulting from a thrombolytic or hemorrhagic stroke.

For example, it is believed that the compounds can be used in the treatment of Alzheimer's patients through the modulation of APP processing to effectuate a beneficial result by: (a) decreasing the formation of Aβ; (b) modulating the generation of a mutually exclusive, alternative-processed form of APP that precludes Aβ formation (α-sAPP); and/or, (c) modulating the generation of partially processed C-terminal Aβ-containing amyloidogenic peptides.

In addition, these compounds may also beneficially modulate neurodegenerative abnormalities not thought to be associated with amyloid plaques, such as stroke, by beneficially affecting the rate of degeneration of the neuronal cytoskeleton that occurs as a result of thrombolytic or hemorrhagic stroke.

It is believed that the treatment of patients with such disorders with these compounds will result in a beneficial modulation of the causative factors involved in neurodegenerative disease states and will result in an enhanced lifestyle as well as to delay or obviate the need to institutionalize these patients.

The compounds can be administered to patients in need of such treatment in a dosage range of 0.01–10 mg per kg of body weight per day and s can be administered by any appropriate route, for example, orally, parenterally, intravenously, intradermally, subcutaneously, or topically, in liquid, semi-liquid or solid form and are formulated in a manner suitable for each route of administration. As stated above, the dose will vary depending on severity of disease, weight of patient and other factors which a person skilled in the art will recognize.

Patients include those with a neurodegenerative disease, including but not limited to Alzheimer's disease, cognition deficits, Down's Syndrome, Parkinson's disease, cerebral hemorrhage with amyloidosis, dementia pugilistica, and head trauma. Treatment is effected by administering to such patient a therapeutically effective amount of a compound of the formulae (I) and (II) defined as above. Particularly preferred for use in these methods are the compounds particularly provided herein of formulae (I) and (II) but with the proviso that, when the compounds have formula (I): (1) at least one of the amino acid residues in the resulting tri-peptide is a non-naturally-occurring α-amino acid or at least one of the $R_1$, $R_3$ and $R_5$ is not a side chain of a naturally-ocurring amino acid; and (2) when X is an aldehyde, the non-naturally occurring amino acid (or side chain thereof) is other than norleucine or norvaline, and when the compounds have formula (II) and X is an aldehyde, $R_1$ is not be norleucine or norvaline.

In some embodiments the compounds of formula (II) are also selected such that: (1) at least one of the amino acid residues in the resulting dipeptide is a non-naturally-occurring α-amino acid or at least one of the $R_1$ and $R_3$ is not a side chain of a naturally-ocurring amino acid; and (2) when X is an aldehyde, the non-naturally occurring amino acid (or side chain thereof) is other than norleucine or norvaline.

In certain preferred embodiments, the compounds have formulae I or II, particularly formula I, as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) when $R_1$ is the side chain from a non-naturally occuring amino acid, it is not the side chain of norleucine or norvaline.

In other preferred embodiments, the compounds have formulae I or II, particularly formula I, as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) none of $R_1$, $R_3$ and $R_5$ is the side chain of norleucine or norvaline.

2. Treatment of diseases characterized by degeneration of the cytoskeleton

Also provided are methods of treating a patient suffering from a disease state characterized by the degeneration of the cytoskeleton arising from a thrombolytic or hemorrhagic stroke by administering a therapeutically effective amount of a compound of the formulae (I) and (II), particularly the compounds of formulae (I), with the proviso that when the compounds have formula (I): (1) at least one of the amino acid residues in the resulting tri-peptide is a non-naturally-occurring α-amino acid or at least one of the $R_1$, $R_3$ and $R_5$ is not a side chain of a naturally-ocurring amino acid; and (2) when X is an aldehyde, the non-naturally occurring amino acid (or side chain thereof) is other than norleucine or norvaline, and when the compounds have formula (II) and X is an aldehyde, $R_1$ cannot be norleucine or norvaline.

In certain preferred embodiments, the compounds for use in this method of treatment have formulae I or II, particularly formula I, as defined above, but with the proviso that: (1) at least one of the amino acid residues in the resulting tri-peptide is a non-naturally-occurring α-amino acid or at least one of the $R_1$, $R_3$ and $R_5$ is not a side chain of a naturally-ocurring amino acid; and (2) when $R_1$ is the side chain from a non-naturally occuring amino acid, it is not the side chain of norleucine or norvaline.

In some embodiments the compounds of formula (II) are also selected such that: (1) at least one of the amino acid residues in the resulting dipeptide is a non-naturally-occurring α-amino acid or at least one of the $R_1$ and $R_3$ is not a side chain of a naturally-ocurring amino acid; and (2) when X is an aldehyde, the non-naturally occurring amino acid (or side chain thereof) is other than norleucine or norvaline.

In other preferred embodiments, the compounds have formulae I or II, particularly formula I, as defined above, but with the proviso that: (1) at least one of the amino acid residues in the resulting di or tri-peptide is a non-naturally-occurring α-amino acid or at least one of the $R_1$, $R_3$ and $R_5$ is not a side chain of a naturally-ocurring amino acid; and (2) none of $R_1$, $R_3$ and $R_5$ is the side chain of norleucine or norvaline.

3. Protease inhibition

The compounds provided herein have activity as inhibitors of proteases, such cysteine proteases, including calpain. It is believed by those of skill in this art that excessive activation of the $Ca^{2+}$-dependent protease calpain plays a role in the pathology of a variety of disorders, including cerebral ischaemia, cataract, myocardial ischaemia, muscular dystrophy and platelet aggregation. Thus, compounds that have activity as calpain inhibitors are considered by those of skill in this art to be useful [see, e.g., U.S. Pat. No. 5,081,284, Sherwood et al. (1993) *Proc. Natl. Acad. Sci. U.S.A.* 90:3353–3357]. Assays that measure the anti-calpain activity of selected compounds are known to those of skill in the art (see, e.g., U.S. Pat. No. 5,081,284). Activities of inhibitors in such in vitro assays at concentrations ($IC_{50}$) in the nanomolar range or lower are indicative of therapeutic activity. Such compounds also have utility in the purification of proteinases, such as cysteine proteases, on affinity columns of these compounds (see, U.S. Pat. No. 5,081,284). Also, calpain inhibitors, such as N-Acetylleucylleucyinorleucinal [see, e.g., EP 0 504 938 A2; and Sherwood et al. (1993) *Proc. Natl. Acad. Sci. U.S.A.* 90:3353–3357], which is commercially available, are used as reagents in the study of protein trafficking and other cellular processes [see, e.g., Sharma et al. (1992) *J. Biol. Chem.* 267:5731–5734]. Finally, inhibitors of cysteine proteases strongly inhibit the growth of *Plasmodium falciparum* and *Schistosoma mansoni* [see, e.g., Scheibel et al. (1984) *Protease inhibitors and antimalarial effects. In: Malaria and the Red Cell, Progress in CLinical and Biolgoical Research,* Alan R. Liss, Inc., NY, pp. 131–142].

The following specific examples further illustrate the methods by which compounds of formulae I and II may be prepared but are not meant to limit the scope of this invention to the specific compounds. Thus, the following examples are included for illustrative purposes only and are not intended to limit the scope of the invention.

EXAMPLE 1

Preparation of N-L-(methyl)Nle N-methoxy-N-methylamide Hydrochloride

To a stirred solution of N-Boc-L-Nle-OH (5.0 g, 22.0 mmol) in anhydrous methylene chloride ($CH_2Cl_2$) (25 mL) under Argon (Ar) at room temperature (R.T.) were added successively hydroxybenzotriazole hydrate (HOBT) (5.8 g, 43.0 mmol), 1-(3-dimethylaminopropyl)-3-ethylcarbodiimide hydrochloride (EDC) (4.1 g, 22.0 mmol) N,O-dimethylhydroxylamine hydrochloride (1.9 g, 20.0 mmol) and triethylamine ($Et_3N$) (3 mL, 22.0 mmol). The reaction mixture was stirred for 16 h. Additional $CH_2Cl_2$ (25 mL) was added and the mixture was washed with saturated aqueous sodium hydrogen carbonate (sat. $NaHCO_3$) (2×10 mL), 10% aqueous hydrogen chloride (10% HCl) (2×10 mL), saturated aqueous sodium chloride (sat. NaCl) (2×10 mL), dried over anhydrous magnesium sulfate (MgSO$_4$), filtered and concentrated. The resultant residue was purified by flash chromatography on silica gel (ethyl acetate:hexane (EA:H); 1:3) to give N-Boc-L-Nle N-methoxy-N-methylamide as a colorless oil (4.1 g, 69.3%): $^1$H NMR (CDCl$_3$, 300 MHz) δ 0.87–0.92 (m, 3H), 1.24–1.72 (m, 15H), 3.21 (s, 3H), 3.78 (s, 3H), 4.66–4.68 (m, 1H), 5.16 (d, 1H, J=9.0 Hz) ppm.

To a stirred solution of the N-Boc-L-Nle N-methoxy-N-methylamide (1.59 g, 5.5 mmol) in 20:1 anhydrous tetrahydrofuran:dimethylformamide (THF:DMF) (22 mL) at 0° C. under Ar was added methyl iodide (0.68 mL, 11.0 mmol) and 60% sodium hydride (NaH) in oil dispersion (0.25 g, 6.0 mmol). The reaction mixture was refluxed for 16 h. The mixture was poured onto 10% HCl and was extracted with EA (3×20 mL). The combined organic extracts were washed with sat. NaCl (2×10 mL), dried (MgSO$_4$), filtered and concentrated in vacuo to afford N-Boc- L-(methyl)Nle N-methoxy-N-methylamide derivative as a yellow oil (0.86 g, 54.5%): $^1$H NMR (CDCl$_3$, 300 MHz) δ 0.87–0.93 (m, 3H), 1.25–1.48 (m, 13H), 1.71–1.73 (m, 2H), 2.83–2.85 (m, 3H), 3.19 (s, 3H), 3.69–3.74 (d, 3H, J=15.0 Hz), 4.80–4.95 (broad (b)-m, 1H) ppm.

N-Boc- L-(methyl)Nle N-methoxy-N-methylamide (0.84 g, 2.9 mmol) was treated with 4 N HCl in dioxane (15 mL) at R.T. The reaction mixture was stirred for 1.5 h then concentrated in vacuo. The solid was treated with anhydrous ether (3×10 mL) and concentrated in vacuo. The resulting N-L-(methyl)Nle N-methoxy-N-methylamide hydrochloride was isolated as a white solid (0.47 g, 85.7%): $^1$H NMR (CDCl$_3$, 300 MHz) δ 0.91–0.95 (m, 3H), 1.73 (m, 4H), 2.06–2.08 (m, 2H), 2.27–2.29 (m, 6H), 3.71–4.09 (m, 3H) ppm.

EXAMPLE 2
Preparation of N-Cbz-L-Leu-L-Leu-DL-(methyl) norleucinal

To a stirred solution of N-L-(methyl)Nle N-methoxy-N-methylamide hydrochloride isolated above in Example 1 (0.87 g, 2.3 mmol) in anhydrous CH$_2$Cl$_2$ (20 mL) under Ar at R.T. were added HOBT (0.62 g, 4.6 mmol), EDC (0.44 g, 2.3 mmol), N-Cbz-L-Leu-L-Leu-OH (0.47 g, 2.1 mmol) and Et$_3$N (0.3 mL, 2.3 mmol). The reaction mixture was stirred for 16 h then taken up in additional CH$_2$Cl$_2$ (20 mL). The mixture was washed with sat. NaHCO$_3$ (2×10 mL), 10% HCl (2×10 mL), sat. NaCl (2×10 mL), dried (MgSO$_4$), filtered and concentrated. The resulting crude was purified by flash chromatography on silica gel (EA:H, 1:3) to yield N-Cbz-L-Leu-L-Leu- L-(methyl)Nle N-methoxy-N-methylamide as a colorless oil (0.4 g, 34.9%): $^1$H NMR (CDCl$_3$, 300 MHz) δ 0.87–1.01 (m, 3H), 1.16–1.95 (m, 12H), 2.95–3.21 (m, 6H), 3.65–3.82 (m, 3H), 4.23 (m,1H), 4.97–5.52 (m, 5H), 6.72–6.75 (m, 1H), 7.30–7.36 (m, 5H) ppm.

To a stirred solution of N-Cbz-L-Leu-L-Leu-L-(methyl) Nle N-methyloxy-N-methylamide (0.33 g, 0.55 mmol) in anhydrous THF (3 mL) under Ar at −78° C. was added a solution of 1.0 M diiso-butylaluminum hydride (DIBAL) in hexanes (2.7 mL, 2.7 mmol). The reaction mixture was stirred for 1 h at −78° C. then quenched by adding a saturated aqueous Rochelle salt solution (15 mL). The mixture was extracted with EA (3×20 mL). The combined organic extracts were dried (MgSO$_4$), filtered, concentrated and purified on silica gel (EA:H; 2:3) to afford the title compound N-Cbz-L-Leu-L-Leu- DL-(methyl)norleucinal as a colorless oil (0.12 g, 45%): Reporting a mixture of diastereomers $^1$H NMR (CDCl$_3$, 300 MHz) δ 0.93–1.01 (overlapping (ol)-m, 15H), 1.25–1.71 (ol-m, 12H), 4.24 (ol-m, 1H),4.52 (ol-m, 1H), 5.03–5.13 (ol-m, 3H), 7.32–7.36 (ol-m, 5H), 9.50–9.56 (ol-m, 1H) ppm.

EXAMPLE 3
Preparation of N-Ac-L-Leu-L-Leu-DL-cyclohexylalaninal

To a stirred solution of N-Ac-L-Leu-OH (5.0 g, 28.9 mmol) in anhydrous CH$_2$Cl$_2$ (50 mL) at R.T. under Ar were added HOBT (7.9 g, 57.7 mmol), EDC (5.5 g, 28.9 mmol), H-L-Leu-OBn p-TsOH (9.9 g, 24.9 mmol) and Et$_3$N (4 mL, 28.9 mmol). The reaction mixture was stirred for 16 h then taken up in additional CH$_2$Cl$_2$ (20 mL). The organic was washed with sat. NaHCO$_3$ (2×10 mL), 1 N HCl (2×10 mL), sat. NaCl (2×10 mL), dried (MgSO$_4$), filtered and concentrated to afford N-Ac-L-Leu-L-Leu-OBn as an oil (9.0 g, 96%): $^1$H NMR (CDCl$_3$, 300 MHz) δ 0.87–0.90 (m, 12H), 1.43–1.68 (m, 6H), 1.94, +1.96 (s+s, 3H), 4.51–4.63 (m, 2H), 5.09–5.19 (m, 2H), 6.61–6.64 (d, 1H, J=9.0 Hz), 6.95–6.97 (d, 1H, J=6.0 Hz), 7.28–7.39 (m, 5H) ppm.

To a stirred solution of N-Ac-L-Leu-L-Leu-OBn (9.09 g, 23.9 mmol) in EA (100 mL) at R.T. was added 20% palladium hydroxide on carbon (Pd (OH)$_2$/C) (0.9 g, 10% by weight). The reaction mixture was placed under 20 psi hydrogen (H$_2$). After 1 h the reaction mixture was filtered through celite and concentrated in vacuo to give N-Ac-L-Leu-L-Leu-OH as a white solid (6.0 g, 87.67%): $^1$H NMR (300 MHz, CDCl$_3$) δ 0.82–0.90 (m, 12H), 1.39–1.82 (m, 9H), 4.18–4.34 (m, 2H), 7.94–8.13 (m, 2H) ppm.

To a stirred solution of N-Ac-L-Leu-L-Leu-OH (1.0 g, 3.5 mmol) in anhydrous CH$_2$Cl$_2$ (10 mL) at R.T. under Ar was added 1,1-carbonyldiimidazole (CDI) (0.68 g, 4.2 mmol). Then Et$_3$N (1.0 mL, 7.0 mmol) and cyclohexylalanine hydrochloride (0.73 g, 3.5 mmol) were successively added. After 16 h of stirring the reaction mixture was concentrated. The residue was titrated with 1 N aqueous hydrogen chloride (1 N HCl), washed with water and dried in vacuo to afford the N-Ac-L-Leu-L-Leu-L-Ala(cyclohexyl)-OH acid as a white solid (0.66 g, 42.5%): $^1$H NMR (CDCl$_3$, 300 MHz) δ 0.90–0.98 (m, 12H), 1.15–1.82 (m, 19H), 1.95–1.98 (m, 3H), 4.36–4.46 (m, 3H) ppm.

To a stirred solution of N-Ac-L-Leu-L-Leu-L-Ala (cyclohexyl)-OH (0.6 g, 1.2 mmol) in anhydrous DMF (10 mL) at R.T. under Ar were added HOBT (0.26 g, 1.3 mmol), 4-dimethylaminopyridine (DMAP) (0.05 g) and 1-thiol propane (0.12 mL, 1.3 mmol). The reaction mixture was stirred for 16 h, then poured onto EA/10% HCl (30 mL/10 mL). The organic layer was separated and washed with sat. NaCl (2×10 mL), dried (MgSO$_4$), filtered and concentrated. Purification by flash chromatography on silica gel (EA:H; 1:3) afforded the N-Ac-L-Leu-Leu-L-Ala(cyclohexyl)-SCH$_2$CH$_2$CH$_3$ as a white solid (0.3 g, 44.4%): $^1$H NMR (CDCl$_3$, 300 MHz) δ 0.86–0.98 (m, 15H), 1.49–2.07 (m, 24H), 2.76–2.87 (m, 2H), 4.64–4.80 (m, 3H) ppm.

To a solution of the thiol ester (0.27 g, 0.52 mmol) in anhydrous CH$_2$Cl$_2$ at R.T. under Ar were added 10% palladium on carbon (Pd/C) (27 mg, 10% by weight) and triethylsilane (Et$_3$SiH) (0.43 mL, 2.6 mmol). The mixture was stirred for 16 h, then filtered through celite and concentrated. The residue was purified by flash chromatography on silica gel (EA:H; 1:3→EA) to afford the title compound N-Ac-L-Leu-L-Leu-DL-cyclohexylalaninal as a white solid (0.12 g, 54.79%): Reporting a mixture of diastereomers $^1$H NMR (CDCl$_3$, 300 MHz) δ 0.85–1.98 (ol-m, 31H), 1.97+ 1.98 (s+s, 3H), 4.25–4.38 (ol-m, 2H), 4.60–4.78 (ol-m, 1H), 7.00–8.00 (ol-m, 3H), 9.48+9.54 (s+s, 1H) ppm.

EXAMPLE 4
Preparation of (2S)-N-Ac-L-Leu-L-Leu N-[2-(hexanenitrile)]amide

To a stirred solution of N-Boc-L-Nle-OH (0.5 g, 2.2 mmol) in anhydrous THF (15 mL) under Ar at −23° C. was added 4-methylmorpholine followed by iso-butyl chloroformate (0.21 mL, 2.2 mmol). The reaction mixture was then treated with gaseous $NH_3$ for 1 h. Stirring was continued at −23° C. for an additional 2 h. The mixture was warmed to R.T. and then poured onto 10% aqueous citric acid (20 mL). The mixture was extracted with EA (3×50 mL). The combined organics were washed with sat. $NaHCO_3$ (3×25 mL), sat. NaCl (2×25 mL), dried ($MgSO_4$), filtered and concentrated to afford N-Boc-L-Nle-$NH_2$ as a white solid (0.48 g, 91%): $^1H$ NMR ($CDCl_3$, 300 MHz) δ 0.84–0.92 (m, 3H), 1.22–1.31 (m, 4H), 1.41 (s, 9H), 1.49–1.59 (m, 1H), 1.74–2.01 (m, 1H), 4.03–4.1 (m, 1H), 5.06 (d, 1H), 5.75 (s, 1H), 6.25 (s, 1H) ppm.

To a stirred solution of the amide (N-Boc-L-Nle-$NH_2$) (0.16 g, 0.67 mmol) in anhydrous $CH_2Cl_2$ (4 mL) at R.T. under Ar were added anhydrous pyridine (0.27 mL, 3.4 mmol) and p-toluenesulfonyl chloride (0.26 g, 1.34 mmol). The reaction mixture was stirred for 3 days, then treated with sat. $NaHCO_3$ (4 mL). The mixture was stirred for 1 h. The organic was separated and the aqueous was extracted with $CH_2Cl_2$ (2×10 mL). The combined organics were washed with 1 N HCl (2×5 mL), dried ($MgSO_4$), filtered and concentrated to give a crude residue. Purification by flash chromatography on silica gel (EA) afforded (2S)-N-Boc-2-amino-hexanenitrile as an oil (0.14 g, 100%): $^1H$ NMR ($CDCl_3$, 300 MHz) δ 0.93 (t, 3H, J=7.3 Hz), 1.25–1.52 (m, 13H), 1.75–1.91 (m, 2H), 4.50–4.61 (m, 1H), 4.82 (bs, 1H) ppm.

To the nitrile (1.0 g, 4.71 mmol) was added 4 N HCl/dioxane (10 mL). The reaction mixture was stirred at R.T. for 30 min. The resultant precipitate was filtered and washed with hexanes (3×5 mL) to afford (2S)-2-amino-hexanenitrile hydrochloride as a white solid (0.68 g, 97.59%): $^1H$ NMR ($CD_3OD$, 300 MHz) δ 0.95–0.99 (m, 3H), 1.10–1.60 (m, 4H), 1.89–2.00 (m, 2H), 4.20–4.30 (m, 1H) ppm.

To a stirred solution of N-Ac-L-Leu-L-Leu-OH (0.87 g, 3.0 mmol) in anhydrous $CH_2Cl_2$ (50 mL) at R.T. under Ar was added EDC (0.58 g. 3.0 mmol), HOBT (0.81 g, 6.0 mmol) and $Et_3N$ (0.41 mL). After 16 h, the reaction mixture was washed with sat. $NaHCO_3$ (2×10 mL), 1 N HCl (2×10 mL), sat. NaCl (2×10 mL), dried ($MgSO_4$), filtered and concentrated. Purification by flash chromatography on silica gel (EA) gave the title compound as a white solid (0.42 g, 35%): $^1H$ NMR ($CDCl_3$, 300 MHz) δ 0.82–0.92 (m, 15H), 1.21–1.99 (m, 12H), 2.02 (s, 3H), 4.51 (m, 1H), 4.64 (m, 1H), 6.78 (m, 1H), 7.50 (m, 1H), 8.06 (m, 1H) ppm.

EXAMPLE 5
Preparation of N-Cbz-L-Leu-L-Leu-DL-Nle-$CO_2$Et

To a stirred solution of N-Cbz-L-Leu-L-Leu-L-Nle-OH (1.0 eq) in anhydrous THF at R.T. under Ar is added DMAP (cat.), pyridine (1.0 eq), ethyl oxalyl chloride (2.0 eq). The mixture is gently refluxed for 3 h. The mixture is treated with water, stirred for 30 min. at R.T. and then extracted with EA. The organic extracts are dried ($MgSO_4$), filtered and concentrated to afford enol ester product as a crude residue. To a stirred suspension of the crude residue (1.0 eq) in anhydrous ethanol at R.T. under Ar is added dropwise a solution of sodium ethoxide in anhydrous ethanol. The reaction mixture is stirred for 3 h. The ethanol is then removed and the residue is treated with ether. The ether solution is washed with water, dried ($MgSO_4$) and evaporated to give a crude residue. This residue is purified by flash chromatography on silica gel to give the peptide ketoester N-Cbz-L-Leu-L-Leu-DL-Nle-$CO_2$Et.

EXAMPLE 6
Preparation of N-Cbz-L-Leu-L-Leu-DL-Nle-$CO_2$H

To a stirred solution of N-Cbz-L-Leu-L-Leu-DL-Nle-$CO_2$Et (1.0 eq), as prepared in Example 5, in methanol at R.T. is added 1 N NaOH (1.1 eq). The mixture is stirred for 6 h. The reaction mixture is cooled to 0° C., acidified with 1 N HCl (pH=3) and extracted with EA. The organic extracts are washed with water, dried ($MgSO_4$), filtered and concentrated to give a crude residue. Trituration with hexane and drying in vacuo gives the title compound, N-Cbz-L-Leu-L-Leu-DL-Nle-$CO_2$H.

EXAMPLE 7
Preparation of N-Cbz-L-Leu-L-Leu-DL-Nle-CONHEt

To a stirred solution of N-Cbz-L-Leu-L-Leu-DL-Nle-$CO_2$Et (1.0 eq), as prepared in Example 5, in anhydrous $CH_2Cl_2$ at R.T. is added 1,2-ethanedithiol (2.2 eq), followed by boron trifluoride etherate (0.1 eq). The mixture is stirred for 16 h. Water and ethyl ether are added. The organic layer is separated, washed with water, sat. NaCl, dried ($MgSO_4$), filtered and concentrated to afford the protected α-ketoester.

The protected α-ketoester is dissolved in ethanol (5 mL) and cooled to 0° C., and ethylamine is bubbled through the solution. The mixture is warmed to R.T., stirred overnight, filtered and concentrated. The crude residue is purified by flash chromatography on silica gel to give the title compound N-Cbz-L-Leu-L-Leu-DL-Nle-CONHEt.

EXAMPLE 8
Preparation of the Precursor Ethyl 2-amino-4-methyl-4-pentenoate Hydrochloride To a solution of N-(diphenylmethylene)glycine ethyl ester (6.6 g, 24.7 mmol) in anhydrous THF at −78° C. under Ar was slowly added 1.0 M lithium bis(trimethylsilyl)amide (LiHMDSi) in THF (24.7 mL, 24.7 mmol) over 15 min. Stirring was continued for 30 min at −78° C., then 3-bromo-2-methylpropene (2.5 mL, 25.0 mmol) was added. The mixture was gradually warmed to R.T. then stirred for 1 h at R.T. The reaction mixture was treated with water and then concentrated. The residue was taken up in EA (50 mL). The organic layer was washed with sat. NaCl (2×10 mL), dried ($MgSO_4$), filtered and concentrated. The crude was purified by flash chromatography on silica gel (EA:H; 1:4) to give ethyl 4-methyl-2-[(diphenylmethylene)amine]-4-pentenoate as a colorless oil (6.4 g, 89.3%): $^1H$ NMR ($CDCl_3$, 300 MHz) δ 1.23–1.29 (t, 3H, J=6.0 HZ), 1.48–1.49 (m, 3H), 2.55–2.69 (m, 2H). 4.11–4.24 (m, 3H), 4.71–4.75 (m, 2H), 7.16–7.83 (m, 10H) ppm.

To a stirred solution of the above ethyl ester (6.4 g, 20.0 mmol) in anhydrous ether (15 mL) at R.T. was added 1 N HCl (70 mL). After 40 min, the two phases were separated, and the aqueous layer was washed with ether (3×10 mL). The aqueous layer was adjusted with 1 N NaOH (pH=10), then extracted with ether (3×20 mL). The combined organic extracts were dried ($MgSO_4$), filtered and then adjusted with 4 N HCl/dioxane (pH=3) and concentrated in vacuo to afford ethyl 2-amino-4-methyl-4-pentenoate hydrochloride as an oil (3.11 g, 79.4%): $^1H$ NMR ($CDCl_3$, 300 MHz) δ 1.25–1.32 (t, 3H, J=6.0 Hz), 1.81 (s, 3H), 2.74–2.81 (m, 2H), 4.22–4.29 (m, 2H), 4.98 (d, 2H, J=12.0 Hz) ppm.

EXAMPLE 9
Preparation of (2SR)-N-Cbz-L-Leu-L-Leu N-[2-(4-methyl-4-pentenal)]amide To a stirred solution of N-Cbz-L-Leu-OH (5.6 g, 20.7 mmol) in anhydrous $CH_2Cl_2$ (50 mL) at R.T. under Ar were added successively HOBT (5.6 g, 41.5 mmol), EDC (4.0 g, 20.7 mmol), H-L-Leu-$OCH_3$ HCl (3.4 g, 18.8 mmol) and $Et_3N$ (2.9 mL, 20.7 mmol). The reaction mixture was stirred for 16 h. The mixture was taken up in additional $CH_2Cl_2$ (30 mL), washed with sat. NaCl (2×10 mL), dried (MgSO$_4$), filtered and concentrated. The resulting residue was purified by flash chromatography on silica gel (EA:H; 1:2) to afford the dipeptide N-Cbz-L-Leu-L-Leu-OCH$_3$ as a white solid (6.0 g, 64.1%): $^1$H NMR (CDCl$_3$, 300 MHz) δ 0.86–0.95 (ol-t, 12H, J=6.0 Hz), 1.48–1.74 (m, 6H), 3.73 (s, 3H), 4.20–4.25 (m, 1H), 4.56–4.63 (m, 1H), 5.11 (s, 2H), 5.20 (d, 1H, J=6.0 Hz), 6.36 (d, 1H, J=6.0 Hz), 7.31–7.39 (m, 5H) ppm.

To a stirred solution of N-Cbz-L-Leu-L-Leu-OCH$_3$ (6.0 g, 14.6 mmol) in MeOH/H$_2$O (3:1) (60 mL) at R. T. was added lithium hydroxide monohydrate (LiOH.H$_2$O) (1.0 g, 43.9 mmol) and hydrogen peroxide H$_2$O$_2$ (30% weight in H$_2$O) (4.5 mL, 43.9 mmol). The reaction mixture was stirred for 3.5 h and then quenched with 10% HCl. The resulting mixture was extracts with EA (3×20 mL). The combined organic extracted were washed with sat. NaCl (2×10 mL), dried (MgSO$_4$) and concentrated in vacuo to afford N-Cbz-L-Leu-L-Leu-OH as a white solid (5.0 g, 90.5%): $^1$H NMR (CDCl$_3$, 300 MHz) δ 0.89–0.92 (t, 12H, J=3.0 Hz), 1.48–1.71 (m, 6H), 4.11–4.13 (m, 1H), 4.55–4.62 (m, 1H), 5.09 (s, 2H), 5.64 (d, 1H, J=9.0 Hz), 6.83 (d, 1H, J=9.0 Hz), 7.33–7.40 (m, 5H) ppm.

To a stirred solution of N-Cbz-L-Leu-L-Leu-OH (3.2 g, 8.5 mmol) in anhydrous CH$_2$Cl$_2$ (35 mL) at R. T. under Ar were added HOBT (2.3 g, 17.1 mmol), EDC (1.6 g, 8.5 mmol), ethyl 2-amino-4-methyl-4-pentenoate hydrochloride, as prepared in Example 8, (1.5 g, 7.8 mmol) and Et$_3$N (1.2 mL, 8.5 mmol). The reaction mixture was stirred for 16 h at R.T. The mixture was taken up in CH$_2$Cl$_2$ (30 mL). The organic layer was washed with sat. NaHCO$_3$ (2×10 mL), 10% HCl (2×10 mL), sat. NaCl (2×10 mL), dried (MgSO$_4$), filtered and concentrated. The residue was purified by flash chromatography on silica gel (EA:H; 1:4) to afford (2SR)-N-Cbz-L-Leu-L-Leu N-[2-[ethyl (4-methyl-4-pentenoate)]amide as a white solid (1.9 g, 47.3%): Reporting a mixture of diastereomers $^1$H NMR (CDCl$_3$, 300 MHz) δ 0.88–0.92 (ol-m, 12H), 1.21–1.29 (ol-m, 3H), 1.51–1.71 (ol-m, 9H), 2.39–2.52 (ol-m, 2H), 4.13–4.21 (ol-m, 3H), 4.47–4.82 (ol-m, 4H), 5.10 (ol-m, 2H), 5.32 (d, 1H, J=9.0 Hz), 6.44–6.77 (m, 2H), 7.29–7.36 (ol-m, 5H) ppm.

To a stirred solution of the above ethyl ester (1.9 g, 3.6 mmol) in anhydrous THF (10 mL) at 0° C. under Ar was added lithium borohydride (LiBH$_4$) (0.16 g, 7.1 mmol). Stirring was continued for 30 min at 0° C. then the mixture was warmed to R. T. After 1 h, 1 N HCl (1 mL) was added to the reaction mixture, and then extracted with EA (3×20 mL). The combined organic extracts were washed with sat. NaCl (2×10 mL), dried (MgSO$_4$), filtered and concentrated in vacuo to afford the crude residue. The residue was purified by flash chromatography on silica gel (EA:H; 1:3) to yield the alcohol as a white solid (1.4 g, 85.6%): Reporting a mixture of diastereomers $^1$H NMR (CDCl$_3$, 300 MHz) δ 0.88–0.95 (ol-m, 12H), 1.47–1.73 (ol-m, 9H), 2.16–2.27 (ol-m, 2H), 3.54–3.67 (ol-m, 2H), 4.12 (ol-m, 2H), 4.33–4.40 (ol-m, 1H), 4.74–4.80 (ol-m, 2H), 5.03–5.37 (ol-m, 3H), 6.34–6.37 (ol-m, 2H), 7.30–7.40 (ol-m, 5H) ppm.

To a stirred solution of anhydrous dimethyl sulfoxide (DMSO) (0.18 mL, 2.25 mmol) in anhydrous THF (5 mL) at −78° C. under Ar was added oxalyl chloride (0.24 mL, 2.25 mmol) dropwise over 5 min. After 30 min, the reaction mixture was treated with a solution of the alcohol (0.5 g, 1.0 mmol) in anhydrous THF (5 mL). Stirring was continued at −78° C. for an additional 30 min, then Et$_3$N (0.65 mL, 4.7 mmol) was added. The reaction mixture was warmed to 0° C. and stirred for 15 min. EA (50 mL) was added to the mixture and the organic layer was washed with sat. NaHCO$_3$ (2×10 mL), 10% HCl (2×10 mL) and sat. NaCl (2×10 mL). The organic layer was dried (MgSO$_4$), filtered and concentrated to afford a crude residue. Purification of the crude by flash chromatography on silica gel (kieselgel 60 silanisiert) (EA:H; 1:5) yielded the title compound as a white solid (0.23 g, 47.8%): Reporting a mixture of diastereomers $^1$H NMR (CDCl$_3$, 300 MHz) δ 0.88–0.98 (ol-m, 12H), 1.52–1.73 (ol-m, 9H), 2.29–2.58 (ol-m, 2H), 4.19 (ol-m, 1H), 4.49–4.51 (ol-m, 2H), 4.76–4.86 (ol-m, 2H), 5.00–5.09 (ol-m, 2H), 5.39–5.42 (ol-m, 1H), 6.70–7.14 (ol-m, 2H), 7.34–7.42 (ol-m, 5H) ppm.

EXAMPLE 10

Preparation of (2S)-N-Cbz-L-Leu-L-Leu N-[2-(thiazole-oxo-pentyl)]amide

To a stirred solution of thiazole (0.11 mL, 1.55 mmol) in anhydrous ether (8 mL) at −78° C. under Ar was slowly added 1.8 M N-butyllithium in hexanes (nBuLi) (1.0 mL, 1.7 mmol). After an additional 20 min of stirring at −78° C. N-Boc-L-Nle N-methoxy-N-methylamide (0.17 g, 0.62 mmol) in anhydrous ether (5 mL) was added. Stirring was continued for 1 h at −78° C. then gradually warmed to R. T. The resulting mixture was treated with 1 N HCl (1 mL), 1 N NaOH (pH=9), and extracted with ether (3×10 mL). The combined organic layers were washed with sat. NaHCO$_3$ (2×10 mL), sat. NaCl (2×10 mL), dried (MgSO$_4$), filtered and concentrated. Purification by flash chromatography on silica gel (EA:H; 1:5) afforded the (2S)-N-Boc-2-amino-thiazole-oxo-pentyl derivative as a white solid (0.14 g, 76%): $^1$H NMR (CDCl$_3$, 300 MHz) δ 0.86 (t, 3H, J=6.0 Hz), 1.23–1.62 (m, 13H), 1.66–1.75 (m, 2H), 5.32–5.46 (m, 2H), 7.70 (d, 1H, J=3.0 Hz), 8.03 (d, 1H, J=6.0 Hz) ppm.

The above derivative (0.13 g, 0.44 mmol) was treated with 4 N HCl/dioxane (5 mL) at R. T. After 30 min the reaction mixture was concentrated in vacuo. The resulting solid was recrystallized (MeOH/Ether) to give the hydrochloride as a white solid (0.1 gr, 75%): $^1$H NMR (CD$_3$OD, 300 MHz) δ 0.64–0.73 (t, 3H, J=6.0 Hz), 1.17–1.21 (m, 4H), 1.76–1.99 (m, 2H), 4.86–4.91 (m, 1H), 7.72–7.98 (m, 2H) ppm.

To the resulting hydrochloride (0.09 g, 0.33 mmol) in anhydrous CH$_2$Cl$_2$ (10 mL) at R. T. under Ar was added HOBT (0.1 g, 0.73 mmol), EDC (0.07 g, 0.36 mmol), N-Cbz-L-Leu-L-Leu-OH (0.09 g, 0.33 mmol) and Et$_3$N (0.09 mL, 0.66 mmol). After 16 h CH$_2$Cl$_2$ (20 mL) was added, and the organic layer was washed with sat. NaHCO$_3$ (2×10 mL), 1 N HCl (2×10 mL), sat. NaCl (2×10 mL), dried (MgSO$_4$), filtered and concentrated. Purification by flash chromatography on silica gel (EA:H;1:1) afforded the title compound as a white solid (0.16 gr, 88%): $^1$H NMR (CDCl$_3$, 300 MHz) δ 0.83–1.06 (m. 15H), 1.20–2.15 (m, 12H), 4.10–4.30 (m, 1H), 4.48–4.61 (m, 1H), 5.11 (s, 2H), 5.15–5.25 (m, 1H), 5.60–5.70 (m, 1H), 6.32–6.50 (m, 1H), 7.30–7.40 (m, 5H), 7.70 (dd, 1H, J=6.0, 3.0 Hz), 8.05 (dd, 1H, J=6.0, 3.0 Hz) ppm.

EXAMPLE 11

Preparation of N-Ac-L-Leu-L-Leu-L-Nle-COCHN$_2$

To a stirred solution of N-Ac-L-Leu-L-Leu-L-Nle-OH (0.3 g, 0.77 mmol), in anhydrous THF (10 mL) at −23° C. were added 4-methylmorpholine (0.1 mL, 0.85 mmol) and iso-butyl chloroformate (0.11 mL, 0.85 mmol). The mixture was stirred at −23° C. for 20 min. The resulting mixture was added to a solution of diazomethane (10.0 mmol) in anhydrous ether (5 mL) at 0° C. The mixture was stirred at 0° C. for an additional 1 h then gradually warmed to R. T., and stirred for an addition 3 h at R. T. The reaction mixture was taken up in $CH_2Cl_2$ (30 mL) and the organic layer was washed with sat. $NaHCO_3$ (2×10 mL), sat. NaCl (2×10 mL), dried ($MgSO_4$) and concentrated. Recrystallization (EA/H) afforded the desired diazomethyl ketone (N-Ac-L-Leu-L-Leu-L-Nle-COCHN$_2$) as a white solid (0.33 g, 92%): $^1$H NMR (CDCl$_3$, 300 MHz) δ 0.88–0.99 (m, 15H), 1.23–1.90 (m, 12H), 2.00 (s, 3H), 4.53–4.68 (m, 1H), 4.72–4.79 (m, 2H), 5.86 (s, 1H), 7.71 (broad doublet (bd) 1H), 7.96 (bd, 1H), 8.16 (bd, 1H) ppm.

EXAMPLE 12
Preparation of (3SR)-N-Ac-L-Leu-L-Leu N-[3-(1,1,1-trifluoro-2-oxoheptyl)]amide To a stirred solution of 1-nitropentane (1.0 g, 8.5 mmol) and trifluoroacetaldehyde ethyl hemiacetal (1.2 mL, 8.5 mL) was added potassium carbonate ($K_2CO_3$) (0.06 g, 0.43 mmol). The reaction mixture was heated at 60° C. under Ar for 3 h. The mixture was cooled to R.T., then taken up in EA (50 mL). The organic layer was washed with 1 N HCl (2×10 mL), sat. NaCl (2×10 mL), dried ($MgSO_4$), filtered and concentrated to give (2SR)-(3SR)-3-nitro-1,1,1-trifluoro-2-heptanol as a crude oil (1.7 g, 93%): $^1$H NMR (CDCl$_3$, 300 MHz) δ 0.91 (t, 3H, J=7.2 Hz), 1.24–1.43 (m, 4H), 2.04–2.11 (m, 2H), 4.08–4.77 (m, 3H) ppm.

To a stirred solution of the nitro-alcohol derivative (1.6 g, 7.4 mmol) in methanol (10 mL) was added Raney Nickel (0.16 g, 10% by weight). The mixture was placed under 35 psi of $H_2$ for 16 h, and then was filtered through celite. The celite was washed with methanol (3×10 mL). The combined organics were concentrated to give (2SR)-(3SR)-3-amino-1,1,1-trifluoro-2-heptanol as an oil (0.8 g, 64.9%): $^1$H NMR (CD$_3$OD, 300 MHz) δ 0.89–0.95 (m, 3H), 1.20–2.10 (m, 6H), 3.30–4.40 (m, 4H) ppm.

To a stirred solution of (2SR)-(3SR)-3-amino-1,1,1-trifluoro-2-heptanol (0.36 g, 2.14 mmol) in anhydrous $CH_2Cl_2$ (20 mL) were added N-Ac-Leu-Leu-OH (0.67 g, 2.4 mmol), HOBT (0.33 g, 2.4 mmol), EDC (0.46 g, 2.4 mmol) and Et$_3$N (0.33 mL, 2.4 mmol). The reaction mixture was stirred for 18 h then washed with sat. $NaHCO_3$ (2×10 mL), 1 N HCl (2×10 mL), sat. NaCl (2×10 mL), dried ($MgSO_4$), filtered and concentrated. Purification by flash chromatography on silica gel (EA:H; 1:2) afforded the trifluoromethyl alcohol peptide derivative as a white solid (0.85 g, 88.8%): Reporting a mixture of diastereomers $^1$H NMR (DMSO-d$_6$, 300 MHz) δ 0.89–0.95 (ol-m, 15H), 1.05–1.90 (ol-m, 12H), 1.95 (s, 3H), 3.91–4.50 (ol-m, 4H) ppm.

To a stirred solution of the above product (0.20 g, 0.44 mmol) at R.T. under Ar (0.2 g, 0.44 mmol) in anhydrous 1:1 THF/$CH_2Cl_2$ (40 mL) were added trifluoroacetic acid (TFA) (0.10 mL, 1.32 mmol) and the Dess-Martin reagent (0.56 g, 1.32 mmol). The reaction mixture was stirred for 24 h then concentrated in vacuo. The residue was treated with a mixture of EA (20 mL), sat. $NaHCO_3$ (5 mL) and saturated aqueous sodium thiosulfate (sat. $Na_2S_2O_3$) (5 mL). The organic layer was separated and washed with a sat. $NaHCO_3$ (2×5 mL), sat. $Na_2S_2O_3$ (2×5 mL), sat. NaCl (2×5 mL), dried ($MgSO_4$), filtered and concentrated. The residue was recrystallized (EA/H) to give the title compound as a white solid (0.11 g, 55%): Reporting a mixture of diastereomers $^1$H NMR (DMSO-d$_6$, 300 MHz) δ 0.81–0.87 (ol-m, 15H), 1.09–1.56 (ol-m, 12H), 1.98 (ol-s, 3H), 3.90–4.0 (ol-m, 1H), 4.20–4.32 (ol-m, 2H) ppm.

EXAMPLE 13
Preparation of (2SR)-H-L-Leu N-[2-(ethyl 4-methyl-4-pentenoate)]amide Hydrochloride To a stirred solution of ethyl 2-amino-4-methyl-4-pentenoate hydrochloride (as prepared in Example 8) (0.70 g, 3.6 mmol) in $CH_2Cl_2$ (10 mL) at R.T. under Ar were added N-Boc-L-Leu-OH (1.0 g, 4.0 mmol), HOBT (1.19 g, 7.9 mmol), EDC (0.76 g, 4.0 mmol) and Et$_3$N (0.55 mL, 4.0 mmol). The reaction mixture was taken up in additional $CH_2Cl_2$ (20 mL) and washed with sat. $NaHCO_3$ (2×10 mL), 1 N HCl (2×10 mL), sat. NaCl (2×10 mL), dried ($MgSO_4$), filtered and concentrated. The resulting residue was purified by flash chromatography on silica gel (EA:H; 1:1) to afford the dipeptide ethyl ester as a white solid (1.05 g, 78.6%): $^1$H NMR (CDCl$_3$, 300 MHz) δ 0.92–0.97 (m, 6H), 1.25–1.30 (t, 3H, J=6 Hz), 1.44–1.74 (m, 15H), 2.37–2.57 (m, 2H), 4.15–4.22 (m, 2H), 4.64–4.94 (m, 4H) ppm.

To the above ester (1.0 g, 2.7 mmol) was added 4 N HCl/dioxane (15 mL), stirred at R.T. for 4 h, then the solvent was removed. Co-evaporation with ether (3×5 mL) yielded the title compound as a white solid (0.8 g, 96.3%): $^1$H NMR (CDCl$_3$, 300 MHz) δ 0.89–1.00 (m, 6H), 1.21–1.31 (m, 3H), 1.44–1.84 (m, 6H), 2.34 (m, 2H), 4.16–4.75 (m, 4H) ppm.

EXAMPLE 14
Preparation of (2SR)-N-[(2S)-2-benzoxy-4-methylpentanoyl]-L-Leu N-[2-(4-methyl-4-pentenal)]amide To a stirred solution of L-Leu-OH (5.0 g, 38.2 mmol) in 1 N $H_2SO_4$ (50 mL) at 0° C. was slowly added over 1½ h a solution of sodium nitrite (NaNO$_2$) (7.5 g, 0.11 mmol) in water (20 mL) while maintaining the temperature at 0° C.. The reaction mixture was gradually warmed to R.T., stirred for 24 h, and concentrated to give a white solid. The solid was extracted with ether (5×50 mL). The combined organic layers were dried ($MgSO_4$), filtered and concentrated to give (2S)-2-hydroxy-4-methylpentanoic acid as an oil (4.1 g, 81.2%): $^1$H NMR (CDCl$_3$, 300 MHz) δ 0.98 (d, 6H, J=12.0 Hz), 1.57–1.67 (m, 2H), 1.82–1.93 (m, 1H), 4.36 (t, 1H, J=6.0 Hz) ppm.

To a stirred solution of the acid (4.0 g, 30.5 mmol) in anhydrous DMF (20 mL) at R.T. under Ar was added cesium carbonate (Cs$_2$CO$_3$) (12.9 g, 40.0 mmol) and methyl iodide (5.7 g, 40.0 mmol). The reaction mixture was stirred for 16 h then taken up in EA (100 mL). The organic layer was washed with sat. $NaHCO_3$ (3×20 mL), 1 N HCl (2×20 mL), dried ($MgSO_4$), filtered and concentrated. Purification by flash chromatography on silica gel (EA:H; 1:4) gave methyl (2S)-2-hydroxy-4-methylpentanoate as a colorless oil (2.5 g, 57%): $^1$H NMR (CDCl$_3$, 300 MHz) δ 0.94–1.01 (m, 6H), 1.56–1.74 (m, 2H), 1.87–1.96 (m, 1H), 3.79 (s, 3H), 4.24 (q, 1H, J=6.0 Hz) ppm.

To a stirred solution of methyl (2S)-2-hydroxy-4-methylpentanoate (0.5 g, 3.4 mmol) in anhydrous $CH_2Cl_2$ (10 mL) at R.T. under Ar was added benzyl 2,2,2-trichloroacetimidate (1.4 mL, 6.8 mmol) and trifluoromethylsulfonic acid (25 μl). After 30 min the reaction mixture was taken up in $CH_2Cl_2$ (20 mL). The organic layer was washed with sat. NaCl (2×10 mL), 1 N HCl (2×10 mL), sat. NaCl (2×10 mL), dried ($MgSO_4$). filtered and concentrated. Purification by flash chromatography on silica gel (EA:H; 1:10) afforded methyl (2S)-2-benzoxy-4-methylpentanoate as an oil (0.6 g, 73.5%): $^1$H NMR (CDCl$_3$, 300 MHz) δ 0.80–0.98 (m, 6H), 1.40–1.58 (m, 1H), 1.69–1.87 (m, 2H), 3.74 (s, 3H), 3.93–4.06 (m, 1H), 4.42 (d, 1H, J=12.0 Hz), 4.68–4.80 (m, 1H), 7.14–7.32 (m, 5H) ppm.

To the above methyl (2S)-2-benzoxy-4-methylpentanoate (0.69 g, 2.92 mmol) in MeOH/$H_2O$ (5 mL/1 mL) was added LiOH.$H_2O$ (0.28 g, 11.7 mmol) and 30% $H_2O_2$ (0.3 mL, 11.7 mmol). After stirring the reaction mixture for 24 h, the mixture was treated with 1 N HCl (pH=3) and the methanol was removed in vacuo. The aqueous layer was extracted with EA (4×15 mL). The combined organic layers were washed with 1 N HCl (2×10 mL), sat. NaCl (2×10 mL), dried (MgSO$_4$), filtered and concentrated. (2S)-2-benzoxy-4-methylpentanoic acid was isolated as a colorless oil (0.65 g, 100%): $^1$H NMR (CDCl$_3$, 300 MHz) δ 0.82–1.60 (m, 6H), 1.53–1.62 (m, 1H), 1.73–1.90 (m, 2H), 3.99–4.50 (m, 1H), 4.46 (d, 1H, J=12.0 Hz), 4.72 (d, 1H, J=12.0 Hz) 7.10–7.26 (m, 5H) ppm.

To a solution of the product from Example 13 (0.5 g, 1.63 mmol) in anhydrous CH$_2$Cl$_2$ (10 mL) at R.T. under Ar was added the above acid (0.4 g, 1.8 mL), HOBT (0.24 g, 1.8 mmol), EDC (0.35 g, 1.8 mmol) and Et$_3$N (0.25 mL, 1.8 mmol). After 16 h the reaction mixture was washed with sat. NaHCO$_3$ (2×10 mL), 1 N HCl (2×10 ml), sat. NaCl (2×10 mL) dried (MgSO$_4$), filtered and concentrated. Purification by flash chromatography afforded the ethyl ester (0.5 g, 62.5%): Reporting a mixture of diastereomers $^1$H NMR (CDCl$_3$, 300 MHz) δ 0.76 (t, 3H, J=6.0 Hz), 0.91–0.99 (ol-m, 12H), 1.22–1.9 (ol-m, 9H), 2.05–2.18 (ol-m, 1H), 2.34–2.43 (ol-m, 1H), 3.71–4.95 (ol-m, 9H), 7.20–7.38 (ol-m, 5H) ppm.

To a solution of the ester (0.5 g, 1.0 mmol) in anhydrous THF (10 mL) at R.T. under Ar was added LiBH$_4$ (0.02 g, 1.0 mmol). Reaction mixture was stirred for 4 h then quenched by the addition of 1 N HCl (1 mL), concentrated, and extracted with EA (3×10 mL). The combined organic layers were washed with sat. NaHCO$_3$ (2×10 mL), 1 N HCl (2×10 mL), sat. NaCl (2×10 mL), dried (MgSO$_4$), filtered and concentrated. Purification by flash chromatography on silica gel (EA:H; 1:3) gave the alcohol as an oil (0.13 g, 30%): Reporting a mixture of diastereomers $^1$H NMR (CDCl$_3$, 300 MHz) δ 0.72–0.98 (ol-m, 2H), 1.10–2.21 (ol-m, 11H), 3.58–4.92 (ol-m, 9H), 7.0–7.50 (ol-m, 7H) ppm.

To anhydrous DMSO (51.1 μl, 0.72 mmol) in anhydrous THF (10 mL) at −78° C. under Ar was slowly added oxalyl chloride (39.3 μl, 0.45 mmol). The mixture was stirred at −78° C. under Ar for 30 min. The alcohol (0.13 g, 3.0 mmol) in anhydrous THF (5 mL) was slowly added, and stirred for an additional 1½ h. Et$_3$N (0.18 mL, 1.4 mmol) was then added, and mixture was gradually warmed to R.T. Stirring was continued for 2 h at R.T. The reaction mixture was taken up in EA (50 mL). The organic layer was washed with sat. NaCl (2×10 mL), 1 N HCl (2×10 mL), sat. NaHCO$_3$ (2×10 mL), sat. NaCl (2×10 mL), dried (MgSO$_4$), and concentrated. Purification by flash chromatography on silica gel (EA:H; 1:4) afforded the desired title aldehyde (0.13 g, 99%): Reporting a mixture of diastereomers $^1$ H NMR (CDCl$_3$, 300 MHz) δ 0.72–0.91 (ol-m, 12H), 1.10–2.30 (ol-m, 11H), 4.0–5.01 (ol-m, 7H), 7.0–7.30 (ol-m, 7H), 9.8+9.76 (s+s, 1H) ppm.

EXAMPLE 15

Preparation of (2SR)-(3S)-N-Cbz-L-Leu-Leu N-[3-(2-hydroxy-heptanoic acid)]amide

To a stirred solution of N-Boc-L-Nle N-methoxy-N-methylamide (1.0 eq) in anhydrous THF (10 mL) at 0° C. under Ar is added LiAlH$_4$ (1.0 eq), and stirred for 3 h at 0° C. followed by the addition of 1 N HCl (1 mL). The mixture is taken up in EA then washed with sat. NaHCO$_3$, 1 N HCl, sat. NaCl, dried (MgSO$_4$), filtered and concentrated to afford the N-Boc-L-norleucinal as a crude residue. To the residue is added an ice-cold solution of NaHSO$_3$ (8 eq) and the mixture is stirred for 24 h at 5° C. To the resulting suspension is added EA and an aqueous potassium cyanide solution (KCN) (8 eq). The reaction mixture is stirred at R.T. for 4 h. The organic phase is washed with water and concentrated to give the cyanohydrin.

The cyanohydrin is hydrolyzed in 4 N HCl/dioxane under reflux for 12 h. The solvent is removed and the residue is washed with anhydrous ether to give the hydrolyzate. To a stirred solution of N-Cbz-L-Leu-Leu-OH (1.0 eq) in anhydrous CH$_2$Cl$_2$ under Ar at R.T. is added CDI (1.1 eq). After 30 min of stirring Et$_3$N (2 eq) and the hydrolyzate (1.0 eq) are added. The mixture is stirred for 6 h, then concentrated. The residue is triturated with 1 N HCl washed with water and dried in vacuo to afford the title compound.

EXAMPLE 16

Preparation of (2SR)-(3S)-N-Cbz-L-Leu-L-Leu N-[3-(methyl 2-hydroxy-heptanoate)]amide To the product obtained from Example 15 in anhydrous ether at 0° C. is added diazomethane. After 3 h the solvent is removed and the residue is purified by flash chromatography on silica gel to give the desired product.

EXAMPLE 17

Preparation of (2SR)-(3S)-N-Cbz-L-Leu-L-Leu N-[3-(benzyl 2-hydroxy-heptamide)]amide To the product of Example 15 in anhydrous CH$_2$Cl$_2$ under Ar at R.T. is added HOBT (1.0 eq), EDC (1.0 eq), Et$_3$N (1.0 eq) and benzylamine (1.0 eq). After 6 h the reaction mixture is washed with sat. NaHCO$_3$, sat. 1 N HCl, sat. NaCl, dried (MgSO$_4$), filtered and concentrated. The residue is purified by flash chromatography on silica gel to afford the desired product.

EXAMPLE 18

Preparation of (3SR)-(4S)-N-Cbz-L-Leu-L-Leu N-[4-(benzyl 3-hydroxy-octamide)]amide To a solution of N-Boc-L-norleucinal (1.0 eq), prepared by reducing N-Boc-L-Nle N-methoxy-N-methylamide as described in Example 15, in THF at −78° C. under Ar is added ethyl lithioacetate (2.2 eq) prepared in situ by the addition of nBuLi (2.2 eq) to excess anhydrous ethyl acetate. After 3 h, the reaction mixture is treated with 1 N HCl, and the organic layer is washed with 1 N HCl, sat. NaHCO$_3$. sat. NaCl, dried (Mg SO$_4$), filtered and concentrated. Purification by flash chromatography on silica gel gives the ester.

The ester is treated with 4 N HCl/dioxane for 30 min, and then concentrated in vacuo. The resulting solid is taken up in anhydrous ether and concentrated in vacuo to give the hydrochloride. The hydrochloride is used without further purification in the next step.

To the hydrochloride (1.0 eq) in anhydrous CH$_2$Cl$_2$ at R.T. under Ar is added HOBT (2.0 eq), EDC (1.0 eq), Et$_3$N (1.0 eq) and N-Cbz-L-Leu-Leu-OH (1.1 eq). After 6 h, the organic layer is washed with sat. NaHCO$_3$, 1 N HCl, dried (MgSO$_4$), filtered and concentrated. Purification by flash chromatography on silica gel gives the ester.

To a stirred solution of the above ester (1.0 eq) in MeOH-H$_2$O is added LiOH.H$_2$O (2 eq) and H$_2$O$_2$ (1.0 eq). After 4 h the reaction is quenched by the addition of 10% HCl and then extracted with EA (2×). The combined organic layers are washed with sat. NaCl, dried (MgSO$_4$) and concentrated to give the acid.

To a solution of the acid (1.0 eq) in anhydrous CH$_2$Cl$_2$ at R.T. under Ar is added EDC (1.0 eq), HOBT (1.0 eq), Et$_3$N (1.0 eq) and benzylamine (1.1 eq). The reaction mixture is stirred for 3 h, washed with sat. NaHCO$_3$, 1 N HCl, sat. NaCl, dried (MgSO$_4$), filtered and concentrated. Purification by flash chromatography on silica gel affords the title compound.

EXAMPLE 19

Preparation of (3S)-N-Cbz-L-Leu-L-Leu N-[3-(1-furfylthio-2-oxoheptane)]amide

To the N-Boc-L-Nle-CHN$_2$ (1.0 eq) is added HCl(g) and pyridine (5 mL). The mixture is taken up in EA and washed with 1 N HCl, sat. NaHCO$_3$, sat. NaCl, dried (MgSO$_4$), filtered and concentrated to give the chloromethyl ketone.

To a solution of the chloromethyl ketone (1.0 eq) in anhydrous THF under Ar at R.T. is added furfuryl mercaptan (2.0 eq) and Et$_3$N (2.0 eq). The reaction mixture is stirred at R.T. for 16 h, and extracted with EA. The combined organic layers are washed with sat. NaCl, sat. NaHCO$_3$, 1 N HCl, dried (MgSO$_4$), filtered and concentrated. Purification by flash chromatography on silica gel affords the furfurylthio-derivative. The derivative is treated with 4 N HCl/dioxane to yield the hydrochloride salt.

To a solution of the above salt (1.0 eq) in anhydrous CH$_2$Cl$_2$ at R.T. under Ar is added HOBT (2.0 eq), EDC (1.0 eq), Et$_3$N (1.0 eq) and N-Cbz-L-Leu-L-Leu-OH (1.1 eq). After 6 h the reaction mixture is washed with sat. NaHCO$_3$, 1 N HCl, sat. NaCl, dried (MgSO$_4$) filtered and concentrated. Purification by flash chromatography on silica gel gives the title compound.

EXAMPLE 20

Preparation of (2SR)-N-[(2R)-[2-(1'-phenyl-1'-propene)-4-methylpentanoyl]-L-Leu N-[2-(4-methyl-4-pentenal)]amide To a stirred solution of 4-methylvaleric acid (10.8 mL, 86.1 mmol) in anhydrous CH$_2$Cl$_2$ (25 mL) was added thionyl chloride (25 mL, 0.34 mmol). The mixture was placed under reflux for 24 h. Then solvent and excess thionyl chloride were removed in vacuo to give the acid chloride as an oil (10.2 g, 90%). The acid chloride was used directly in the next step.

To the acid chloride (2.7 g, 20.3 mmol) in anhydrous CH$_2$Cl$_2$ (50 mL) at R.T. under Ar was added DMAP (0.10 g), Et$_3$N (4.6 mL, 33.8 mmol) and (4S, 5R)-(−)-4-methyl-5-phenyl-2-oxazolidinone (3.0 g, 16.9 mmol). The reaction mixture was stirred for 16 h then washed with 1 N HCl (2×10 mL), sat. NaHCO$_3$ (2×10 mL), sat. NaCl (2×10 mL), dried (MgSO$_4$), filtered and concentrated. Purification by flash chromatography on silica gel (EA:H; 1:20) afforded the imide as an oil (2.8 g, 61 %): $^1$H NMR (CDCl$_3$, 300 MHz) δ 0.80–1.10 (m, 9H), 1.60–1.90 (m, 3H), 2.40–2.55 (m, 2H), 4.80–4.90 (m, 1H), 5.70–5.80 (m, 1H), 7.20–7.50 (m, 5H) ppm.

To a solution of the imide (2.5 g, 9.14 mmol) in anhydrous THF (40 mL) at −78° C. under Ar was slowly added a 1.5 M solution of lithium diisopropylamide (LDA) in anhydrous THF (6.0 mL, 9.14 mmol) followed by cinnamyl bromide (1.8 g, 9.14 mL) in anhydrous THF (10 mL). The reaction mixture was stirred at −78° C. for 1 h then gradually warmed to R.T. Stirring was continued at R.T. for 1 h then the mixture was treated with 1 N HCl (5 mL). The solvent was removed and the aqueous was taken up in EA (70 mL). The aqueous was separated and the organic was washed with sat. NaCl (2×10 mL), 1 N HCl (2×10 mL), sat. NaHCO$_3$ (2×10 mL), sat. NaCl (2×10 mL), dried (MgSO$_4$) filtered and concentrated. Purification by flash chromatography on silica gel (EA:H; 1:4) afforded the alkylated derivative as an oil (3.5 g, 98.7%): $^1$H NMR (CDCl$_3$, 300 Mhz) δ 0.73 (d, 3H, J=6.0 Hz), 0.80–0.92 (m, 6H), 1.14–1.40 (m, 1H), 1.48–1.79 (m, 1H), 1.75–1.84 (m, 1H), 2.42 (m, 2H), 4.10–4.20 (m, 1H), 4.71–4.78 (m, 1H), 5.28 (d, 1H, J=9.0 Hz), 6.35 (m, 1H), 6.45 (m, 1H), 7.21–7.25 (m, 5H) ppm.

To a solution of the above product (0.65 g, 1.66 mmol) in 3:1 MeOH:H$_2$O (20 mL) at R.T. were added LiOH.H$_2$O (0.61 g, 4.98 mmol) and 30% H$_2$O$_2$ (0.83 mL). The reaction mixture was stirred for 4 h. The mixture was cooled to 0° C. and quenched by the addition of 1 M Na$_2$S$_2$O$_3$ (1.6 mL) and allowed to warm to R.T. After 14 h the resulting solution was poured onto sat. NaHCO$_3$ (20 mL). The aqueous was extracted with CH$_2$Cl$_2$ (3×30 mL) then acidified with 1 N HCl (pH=3). The aqueous was then extracted with CH$_2$Cl$_2$ (3×20 mL) and the combined organics were dried (MgSO4), filtered and concentrated. The residue was purified by flash chromatography on silica gel (EA:H; 1:1) to give (2S)-2-(1'-phenyl-1'-propene)-4-methylpentanoic acid as an oil (0.30 g, 78.0%): $^1$H NMR (CDCl$_3$, 300 MHz) δ 0.88–1.01 (m, 6H), 1.29–1.42 (m, 3H), 1.59–1.70 (m, 2H), 2.55 (m, 3H), 6.13 (m, 1H), 6.47 (d, 1H, J=6.0 Hz), 7.31–7.40 (m, 5 H) ppm.

To a stirred solution of L-Leu-OMe HCl (0.14 g, 0.70 mmol) and (2S)-2-(1'-phenyl-1'-propene)-4-methylpentanoic acid (0.16 g, 0.69 mmol) in anhydrous CH$_2$Cl$_2$ (15 mL) at R.T. were added HOBT (0.19 g, 1.38 mmol), EDC (0.15 g, 0.78 mmol) and Et$_3$N (0.91 mL, 0.70 mmol). After 16 h the reaction mixture was washed with sat. NaHCO$_3$ (2×10 mL), 1 N HCl (×10 mL), sat. NaCl (2×10 mL), dried (MgSO$_4$), filtered and concentrated. Purification of the crude residue by flash chromatography on silica gel (EA:H; 1:1) afforded the methyl ester as an oil (0.24 g, 95%): $^1$H NMR (CDCl$_3$, 300 MHz) δ 0.76–0.78 (d, 3H, J=6.0 Hz), 0.82–1.06 (m, 3H), 1.26–1.41 (m, 1H), 1.44–1.72 (m, 2H), 2.22–2.30 (m, 2H), 2.35–2.46 (m, 1H) 3.72 (s, 3H), 4.57 (m, 1H), 6.16 (m, 1H), 6.43 (m, 1H), 7.25–7.41 (m, 5H) ppm.

To the above methyl ester (0.28 g, 0.78 mmol) in MeOH-H$_2$O (15 mL-5 mL) with stirring at 0° C. was added 1 N LiOH.H$_2$O (0.95 mL) and 30% H$_2$O$_2$ (1.4 mL). After 2 h 1 N HCl (4 mL) was added and the aqueous layer was extracted with EA (3×30 mL). The combined organics were washed with sat. NaCl (2×20 mL), dried (MgSO$_4$), filtered and concentrated to give a crude residue. Purification by flash chromatography on silica gel (EA:H; 1:1) afforded the acid as an oil (0.21 g, 0.61 mmol): $^1$H NMR (CDCl$_3$, 300 MHz) δ 0.59–1.10 (m, 12H), 1.12–1.71 (m, 6H), 2.60–2.63 (m, 3H), 4.45 (m, 1H), 6.21 (m, 1H) 6.40 (m, 1H), 7.25–7.41 (m, 5H) ppm.

To a stirred solution of the acid (0.25 g, 0.72 mmol) and ethyl 2-amino-4-methyl-4-pentenoate (0.16 g, 0.8 mmol) in anhydrous CH$_2$Cl$_2$ (15 mL) at R.T. were added HOBT (0.19 g, 1.44 mmol), EDC (0.15 g, 0.79 mmol) and Et$_3$ N (0.12 mL, 0.80 mmol). After 4 h the reaction mixture was washed with sat. NaHCO$_3$ (2×10 mL), 1 N HCl (2×10 mL), sat. NaCl (2×10 mL), dried (MgSO$_4$), filtered and concentrated. The residue was purified by flash chromatography on silica gel (EA:H; 1:1) to give (2SR)-[(2R)-[2-(1'-phenyl-1'-propene)-4-methyl pentanoyl]]-L-Leu N-[2-(ethyl 4-methyl-4-pentenoate)]amide as a solid (0.18 g, 51%): $^1$H NMR CDCl$_3$, 300 MHz) δ 0.81–1.10 (m, 12H), 1.30–1.73 (m, 15H), 2.27–2.51 (m, 2H), 4.14–4.17 (m, 2H), 4.22–4.49 (m, 2H), 4.59 (m, 1H), 6.21 (m, 1H), 6.43 (m, 1H), 7.17–7.19 9 m, 2H), 7.25 –7.41 (m, 5H) ppm.

To the above ethyl ester (0.3 g, 0.62 mmol) in anhydrous THF (20 mL) at 0° C. under Ar with stirring was added LiBH$_4$ (47 mg, 2.15 mmol).

After 30 min at 0° C. the reaction mixture was warmed to R.T. Stirring was continued for 2 h then quenched with 1 N HCl (2 mL). The mixture was extracted with EA (3×10 mL). The combined organics were washed with sat. NaHCO$_3$ (2×10 mL), 1 N HCl (2×10 mL), sat. NaCl (2×10 mL), dried (MgSO$_4$), filtered and concentrated. Purification by flash chromatography on silica gel (EA) gave the alcohol as an oil (0.24 g, 87%): $^1$H NMR (CDCl$_3$, 300 MHz) δ 0.72–1.02 (m, 12H), 1.20–1.86 (m, 13H), 2.21–2.56 (m, 4H), 3.60–3.68 (m, 2H), 4.21–4.25 (m, 1H), 4.80–4.85 (m 1H), 6.10–6.15 (m, 1H), 6.45–6.50 (m, 1H), 7.17–7.19 (m, 2H), 7.25–7.35 (m, 5H) ppm.

To anhydrous DMSO (0.08 mL, 1.08 mmol) in anhydrous CH$_2$Cl$_2$ (5 mL) at −78° C. under Ar with stirring was added oxalyl chloride (0.06 mL, 0.68 mmol). The mixture was stirred for 30 min then the alcohol (0.19 g, 0.45 mmol) in anhydrous $CH_2Cl_2$ (5 mL) was added. Stirring was continued at −78° C. for 2 h. $Et_3N$ (0.29 mL) was then added to the reaction mixture and the mixture was allowed to gradually warm to R.T. Stirring was continued for 1 h. The reaction mixture was taken up in additional $CH_2Cl_2$ (20 mL). The organic was washed with sat. $NaHCO_3$ (2×10 mL), 1 N HCl (2×10 mL), sat. NaCl (2×10 mL), dried ($MgSO_4$), filtered and concentrated to give a crude residue. Purification by flash chromatography on silica gel (EA:H;1:1) afforded the title compound as an oil (20.0 g, 10%): Reporting a mixture of diastereomers $^1H$ NMR ($CDCl_3$, 300 MHz) δ 0.78–1.79 (ol-m, 23H), 1.96–2.66 (ol-m, 2H), 4.11–4.93 (ol-m, 4H), 5.77–6.43 (ol-m, 3H), 7.19–7.25 (ol-m, 5H), 7.97–8.06 (ol-m, 2H), 9.56+9.57 (s+s, 1H) ppm.

EXAMPLE 21
Preparation of N-Cbz-L-Pro-L-Leu-L-norleucinal

The title compound was isolated as a colorless oil (0.13 g) using the methodology outlined in Example 2: $^1H$ NMR ($CDCl_3$, 300 MHz) δ 0.80–0.91 (m, 9H), 1.24–2.22 (m, 3H), 3.45–3.60 (m, 2H), 4.11–4.43 (m, 3H), 5.06–5.16 (m, 2H), 6.40–7.00 (m, 2H), 7.30–7.40 (m, 5H), 9.5 (s,1H) ppm.

EXAMPLE 22
Preparation of N-Cbz-L-Leu-L-Leu-DL-cyclohexylglycinal

Using the procedure set forth in Example 3 the title compound was isolated as a yellowish solid (50.0 mg): Reporting a mixture of diastereomers $^1H$ NMR ($CDCl_3$, 300 MHz) δ 0.87–1.72 (ol-m, 29H), 1.99+2.00 (s+s, 3H), 4.35–4.75 (ol-m, 3H), 6.57–7.82 (ol-m, 3H), 9.56–9.63 (ol-m, 1H) ppm.

EXAMPLE 23
Preparation of N-Fmoc-L-Leu-L-Leu-DL-norleucinal

The title compound was prepared from the corresponding propane thiol ester using substantially the same procedure described in Example 3. N-Fmoc-L-Leu-L-Leu-DL-norleucinal was isolated as a colorless oil (15 mg): Reporting a mixture of diastereomers $^1H$ NMR ($CDCl_3$, 300 MHz) δ 0.52–0.61 (ol-m, 3H), 0.80–1.05 (ol-m, 16H), 1.22–1.26 (ol-m, 2H), 2.02–2.10 (ol-m, 4H), 4.04–4.69 (ol-m, 5H), 5.21–5.27 (ol-m, 1H), 7.23–7.84 (ol-m, 8H), 9.50–9.56 (ol-m, 1H) ppm.

EXAMPLE 24
Preparation of (2SR)-N-Ac-L-Leu-L-Leu N [2-(trans-4-hexenal)]amide The title compound was isolated as a white solid (0.48 g) following the procedure set forth in Example 9: Reporting a mixture of diastereomers $^1H$ NMR ($CDCl_3$, 300 MHz) δ 0.89–1.26 (ol-m, 12H), 1.51–1.74 (ol-m, 9H), 1.93 (s, 3H), 2.40–2.61 (ol-m, 2H), 3.40–4.01 (ol-m, 0.3H), 4.35–4.61 (ol-m, 3H), 5.30–5.37 (ol-m, 1H), 5.49–5.50 (ol-m, 1H), 6.70–7.71 (ol-m, 3H), 9.50–9.56 (ol-m, 0.7H) ppm.

EXAMPLE 25
Preparation of N-Ac-L-Leu-L-Phe-DL-norleucinal

N-Ac-L-Leu-L-Leu-DL-norleucinal was isolated as a white solid (0.12 g) using similar methodology that is set forth in Example 3: Reporting a mixture of diatereomers $^1H$ NMR ($CDCl_3$, 300 MHz) δ 0.81–0.88 (ol-m, 9H), 1.23–1.83 (ol-m, 8H), 1.94–1.96 (s+s, 3H), 2.96–3.21 (ol-m, 0.4H), 3.31–3.47 (ol-m, 2H), 4.02–5.10 (ol-m, 3H), 7.05–7.20 (ol-m, 5H) 9.20–9.49 (ol-m, 0.6H) ppm.

EXAMPLE 26
Preparation of N-Cbz-L-Leu-L-Leu-L-norleucinal

Using the procedure set forth in Example 2 the title compound was isolated as a colorless oil (0.22 g): $^1H$ NMR ($CDCl_3$, 200 MHz) δ 0.86–0.93 (m, 9H), 1.23–1.86 (m, 9H), 2.37 (m, 0.2H), 3.90 (s, 2H), 4.39–4.51 (m, 1H), 4.57–4.61 (m, 1H), 5.08 (m, 2H), 5.94 (hs, 1H), 7.12–7.23 (m, 2H), 7.23–7.32 (m, 5H), 9.49 (s, 0.8H) ppm.

EXAMPLE 27
Preparation of (2SR)-N-Ac-L-Leu-L-Leu N-[2-(4-methyl-4-pentenal)]amide The title compound was isolated as a white solid (0.2 g) following substantially the same procedure described in Example 9: Reporting a mixture of diastereomers $^1H$ NMR ($CDCl_3$, 300 MHz) δ 0.81–0.88 (ol-m, 12H), 1.31–1.90 (ol-m, 8H), 1.92 (ol-m, 3H) 2.23–2.56 (ol-m, 2H), 4.70–4.80 (ol-m, 1H), 4.78–5.00 (ol-m, 3H), 7.70–7.80 (ol-m, 1H), 8.01–8.60 (ol-m, 2H), 9.43+9.52 (s+s, 1H) ppm.

EXAMPLE 28
Preparation of N-Cbz-L-Leu-L-(methyl)Leu-DL-norleucinal

Following the procedures set forth in Examples 1 and 2 the title compound was isolated as a colorless oil (0.14 g): Reporting a mixture of diastereomers $^1H$ NMR ($CDCl_3$, 300 MHz) δ 0.86–1.02 (ol-m, 15H), 1.26–1.98 (ol-m, 12H), 2.80–3.00 (ol-s, 3H), 4.30–4.80 (ol-m, 3H), 4.95–5.20 (ol-m, 2H), 7.29–7.36 (ol-m, 5H), 9.51 (ol-s, 1H) ppm.

EXAMPLE 29
Preparation of N-Dansyl-L-Leu-L-Leu-DL-norleucinal

The title compound was isolated as a pale yellow solid (0.13 g) using the methodology described in Example 9: Reporting a mixture of diastereomers $^1H$ NMR ($CDCl_3$, 300 MHz) δ 0.58–2.50 (ol-m, 23H), 2.89 (ol-s, 6H), 3.30–3.70 (ol-m, 1H), 4.38–4.52 (ol-m, 2H), 4.81–4.94 (ol-m, 1H), 5.30–5.71 (ol-m, 1H), 6.75–6.96 (ol-m, 1H), 7.19–7.36 (ol-m, 2H), 7.50–7.65 (ol-m, 2H), 8.20–8.30 (ol-m, 2H), 8.56–8.61 (ol-m, 1H), 9.52–9.61 (ol-s, 1H) ppm.

EXAMPLE 30
Preparation of N-Ac-L-Phe-L-Leu-DL-norleucinal

The title compound N-Ac-L-Phe-L-Leu-DL-norleucinal was obtained as a white solid (0.19 g) following substantially the same procedure described in Example 9: Reporting a fully hydrated amino-aldehyde $^1H$ NMR ($CDCl_3$, 300 MHz) δ 0.64–1.01 (ol-m, 9H), 1.51–1.71 (ol-m, 9H), 1.87–1.95 (ol-s, 3H), 2.79–3.17 (ol-m, 2H), 3.34–3.41 (ol-s, 3H), 3.85–4.68 (ol-m, 4H), 7.16–7.29 (ol-m, 5H) ppm.

EXAMPLE 31

ASSAYS FOR IDENTIFICATION OF COMPOUNDS HAVING ACTIVITY AS MODULATORS OF THE PROCESSING OF Aβ

A. Immunoblot assay for APP peptide

Human glioblastoma cells (ATCC Accession No. HTB16) were stably transfected with a DNA expression vector encoding a 695 amino acid isoform variant of the amyloid precursor protein (APP) containing the familial Swedish double mutations at codons 670 and 671 (K to N and M to L, respectively; see Mullan et al. (1992) *Nature Genet.* 1:345–347) and an additional mutation at codon 717 (V to F; see Murrell et al. (1991) *Science* 254:97–99) to produce cells designated HGB 717/Swed. High levels of Aβ are detectable in the conditioned medium isolated from HGb 717/Swed cultured cells. The medium also contains larger secreted fragments, α-sAPP$_{695}$, which are alternatively processed APP fragments whose generation precludes Aβ formation.

HGB 717/Swed cells were grown at 37° C. under a 5% carbon dioxide atmosphere in Dulbecco's modified eagle medium (DMEM; Gibco) supplemented with 10% heat-inactivated fetal calf serum, 0.45% glucose, 2 mM L-glutamine, 100 units/ml penicillin, and 100 µg/ml streptomycin sulfate (Gemini Bioproducts). Approximately $1 \times 10^6$ cells were incubated overnight in 5 ml of DMEM containing varying µM final concentrations of desired test compounds or a DMSO control. Conditioned medium was collected, and unwanted cells and debris were removed by sedimentation at 3,000 rpm at 4° C.

Aβ peptides were isolated from the medium by immunoaffinity purification using an Aβ-specific antibody. To reduce the interaction of non-specific binding of unrelated proteins, such as serum proteins, to the Aβ antibody, the medium was pre-treated with rabbit antisera and Protein A Sepharose (Pharmacia) for 4 hours at 4° C. The sepharose-bound material was removed by centrifugation at 3,000 rpm at 4° C. for 10 min, and Aβ peptides were immunoaffinity purified from the clarified medium by incubation overnight with an affinity purified polyclonal rabbit antibody (referred to as 2939) prepared against a synthetic Aβ peptide corresponding to amino acids 1 to 28. Protein A-conjugated sepharose was added to immobilize the Aβ-antibody complexes, and the resin was pelleted by centrifugation at 3,000 rpm at 4° C. for 10 min. The Aβ-antibody complexes were eluted from the matrix by denaturing the complex by boiling in the presence of SDS.

Equal portions of each sample were loaded on 16% Tricine gels (Novex), and subjected to electrophoresis. Resolved proteins were transferred from the gel to Hybond nitrocellulose (Amersham, Arlington Heights, Ill.) by electroblotting, and incubated with the commercially available monoclonal antibody 6E10 (obtained from Drs. Kim and Wisniewski, Institute for Basic Research, NY, see, published International PCT application WO 90/12871), which specifically recognizes Aβ residues 1 to 17. Specifically bound antibody was detected using a biotinylated goat anti-mouse IgG secondary antibody (Sigma), followed by the addition of streptavidin conjugated to horseradish pre-oxidase (Amersham, Arlington Heights, Ill.), and documented by luminescent detection (Amersham). Levels of Aβ peptides were determined by laser densitometry of visualized films. A positive result in the assay is a decrease in the formation of the 4-kDa Aβ peptides relative to the DMSO control. The values for the relative percent inhibition of Aβ formation for several of the compounds are shown in Table I:

INHIBITION OF Aβ FORMATION

| COMPOUND | % INHIBITION OF Aβ |
|---|---|
| Ac—L—L—NI—(DM) | 87[a] |
| Cbz—L—L—[CH3]—NI—(H) | 97[b] |
| Ac—L—L—NI—(CN) | 94[a] |
| Cbz—L—F—Lene—(H) | 69[c] |
| Ac—L—L—Chg—(H) | 99[a] |
| Cbz—L—F—Cha—(H) | 100[b] |
| Ac—L—L—Cha—(H) | 46[c] |
| Ac—L—L—Nlene—(H) | 96[a] |
| Cbz—P—L—NI—(H) | 80[b] |
| Cbz—L—L—Lene—(H) | 95[c] |
| Cbz—L—[CH3]—L—NI—(H) | 77[b] |
| 2S-benzoxyvaleric-L—Lene—(H)* | 85[b] |
| Ac—L—L—NI—(TFMK) | 50[a] |
| Fmoc—L—L—NI—(H) | 89[d] |

B. ELISA assay for total sAPP

Human glioblastoma cells (ATCC Acession No. HTB16) were stably transfected with a DNA expression vector encoding the 695 amino acid isoform of the amyloid precursor protein ($APP_{695}$). The resulting cells are designated HGB695 cells. High levels of secreted proteolytic processed fragments of $APP_{695}$ (sAPP) are detectable in the culture medium ($sAPP_{695}$).

Approximately $1 \times 10^5$ cells were plated into 12-well dishes and were grown for 72 hours at 37° C. under a 5% carbon dioxide atmosphere in 1 ml of Dulbecco modified eagle medium (DMEM) supplemented with 10% heat-inactivated fetal calf serum, 0.45% glucose, and 100 units/ml penicillin, 100 µg/ml streptomycin sulfate and 2 mM L-glutamine. Following incubation, the medium was removed and 1 ml of supplemented DMEM medium containing 5 µl of DMSO or DMSO containing the desired test compound within a range about 5 to 100 µM (final concentration in the well), was added to each well, and incubation was continued for 24 hours. Unwanted cells and debris were removed by sedimentation at 3,000×g for 10 min at room temperature. Supernatants were stored at −20° C. for analysis.

In order to determine the amount of sAPP in the supernatants, a capture antibody, such as monoclonal antibody P2-1, which recognizes an epitope located in the amino terminus of APP (see, e.g., U.S. Pat. No. 5,270,165) was attached to the wells of a 96-well microtiter plate by incubating the antibody in the plate for 60 min at 37° C. The plates were washed three times with 0.3 ml of 0.1% Tween-20 in phosphate-buffered saline (PBS). The non-specific interaction of unrelated proteins (such as serum proteins that may interfere with the analysis) with the antibody was reduced by incubating the pre-treated wells for 30 min at 37° C. with a solution of 0.5% casein in PBS (150 µl/well). Wells were washed thoroughly with 0.1% Tween-20 in PBS prior to analysis of samples.

The conditioned medium supernatant was diluted 1:20 in 0.95 ml of 0.1% CHAPS (3-[(3-cholamidopropyl)-dimethylammonio]-1-propanesulfonate) in PBS. Supernatant samples (100 µl/well) or sAPP standards (100 µl/well) of a range about 5 to 50 ng/ml were added to the pre-treated wells and incubated for 60 min at 37° C. The supernatant was removed and each sample well was washed as described above. A horseradish peroxidase (HRP) conjugated goat affinity purified antibody, raised against $sAPP_{695}$, was diluted in 0.1% Tween-20 in PBS and 10% goat serum and employed as the "signal antibody". The unbound antibody was removed by washing, and to each well, 0.1 ml of the chromagenic substrate K-Blue Solution (Elisa Technologies, Lexington, Ky.) was added and samples were incubated for 15 min at ambient temperature. Reactions were stopped by the addition of 0.1 ml of a 9.8% solution of phosphoric acid. The optical density of samples was measured by spectrophotometry at 450 nm. The concentration of $sAPP_{695}$ peptides in the conditioned medium was estimated from the $sAPP_{695}$ standard curve. Samples were analyzed in duplicate with the appropriate standards and reference controls [i.e., a known protease inhibitor compound, such as N-acetylleucylleucyinorleucinalof given potency and concentration].

C. CELL LYSATE ASSAY

In this assay, the effect of compounds on the modulation of the generation of partially processed C-terminal Aβ-containing amyloidogenic peptides is examined. HGB695 human glioblastoma cells were employed and grown in 12-well dishes essentially as described in Example 31B with the following modifications. The DMEM growth media were supplemented with varying μM concentrations of compounds or DMSO control and 100 μM leupeptin and 1 μM PMA phorbol ester and were incubated with cell cultures for 16 hours and cells were grown to approximately 2.5×10$^6$ cells per well.

Harvested cells from each well were lysed in 100 μl of lysis buffer containing 50 mM Tris-HCl, pH 7.8, 150 mM NaCl, 1% NP-40, 0.1% SDS and 0.5% deoxycholate supplemented with 1 mM PMSF. Equal volumes of cell lysates in Laemmli SDS buffer were loaded onto 16% SDS-Tricine polyacrylamide gels (Novex) and subjected to electrophoresis. Separated proteins were transferred to supported nitrocellulose (BioRad) by electroblotting. Nonspecific binding of proteins to the nitrocellulose membrane was blocked by incubating in a solution of 5% non-fat dried milk in PBS. The nitrocellulose membrane was washed three times in PBS and then incubated in PBS containing a 1:5000 dilution of a rabbit polyclonal antibody raised against the C-terminal 19 amino acids of APP (provided by S. Gandy, Rockefeller University, NY). The nitrocellulose membrane was washed as described above and incubated with a secondary biotinylated goat anti-rabbit IgG antibody. Specifically bound antibody was detected using a streptavidin horseradish peroxidase conjugate, and visualized in combination with an enhanced chemoluminescent detection kit (Amersham). Potentially amyloidogenic peptides greater than 9 and less than 22 kDa were quantitated by densitometric scans of developed films within the linear range as described in Example 31B. A positive result for a compound in the cell lysate assay is denoted by a decrease in the levels of the protein bands greater than 9 and less than 22 kDa relative to the appropriate control samples.

D. ELISA ASSAY FOR α-sAPP

Human HGB695 glioblastoma cells transfected with DNA encoding the 695 amino acid isoform of APP were grown and treated with test compound or DMSO as described in Example 31B. Medium from the cultured cells was obtained as described in Example 31B and analyzed for α-sAPP in an ELISA assay as follows. The wells of a 96-well microtiter plate were coated with a monoclonal antibody that specifically recognizes the amino terminus of human sAPP (e.g., monoclonal antibody P2-1) by incubating the antibody in the plate for 60 min at 37° C. The plates were washed three times with 0.3 ml of 0.1% Tween-20 in PBS. The non-specific interaction of unrelated proteins (e.g., serum peptides that may interfere with the analysis) with the antibody was reduced by incubating the pre-treated wells with a solution of 0.5% casein in PBS for 30 min at 37° C. Wells were washed with 0.1% Tween-20 in PBS prior to analysis of media samples.

The conditioned media were diluted 1:20 in 0.95 ml of 0.1% CHAPS in PBS. Media samples (100 μl/well) or α-sAPP standards (100 μl/well) in a range of about 3 to 18 ng/ml were added to the wells for a 60 min incubation at 37° C. The solution was then removed and each sample well was washed as described above. A horseradish peroxidase-conjugated rabbit affinity purified antibody raised against a synthetic peptide consisting of the first 15 amino acids of Aβ (referred to as antibody 3369) was diluted in 0.1% Tween-20 in PBS plus 10% normal rabbit serum and added to the wells as the signal antibody. The plates were incubated for 60 min at 37° C. and then washed to remove unbound antibody. The chromogenic substrate K-Blue Solution (Elisa Technologies, Lexington Ky.) was added to the wells (0.1 ml/well) and allowed to incubate for 15 min at ambient temperature. The reactions were stopped by addition of 0.1 ml of a 9.8% solution of phosphoric acid. The optical density of the samples was measured by spectrophotometry at 450 nm. The concentration of α-sAPP in the media was estimated from the α-sAPP standard curve. Samples were analyzed in duplicate.

EXAMPLE 32

METHOD OF INDICATING ALZHEIMER'S DISEASE

Total s-APP and α-sAPP levels in cerebrospinal fluid (CSF) of normal subjects and members of a Swedish family carrying mutations of the APP gene at codons 670 and 671 (APP$_{670/671}$) were measured and compared. The APP$_{670/671}$ mutation in the Swedish family is associated with a high incidence of early onset Alzheimer's disease (AD). The clinical diagnosis of AD in the Swedish family harboring the mutation was based on NINCDS-ADRDA criteria [McKhann, et al. (1984) *Neurology* 34:939–944]. The diagnosis was confirmed by neuropathologic examination of the brain of one deceased mutation carrier [Lannfelt, et al. (1994) *Neurosci. Lett.* 168:254–256]. Cognitive functioning was assessed with the Mini Mental State Examination (MMSE) [Folstein, et al. (1975) *J. Psychiatry Res.* 12:189–198]. The presence or absence of the APP$_{670/671}$ mutation was determined by polymerase chain reaction (PCR) nucleic acid amplification and restriction enzyme digestion according to a previously established procedure [Lannfelt, et al. (1993) *Neurosci. Lett.* 153:85–87].

Lumbar CSF was obtained from eight normal non-carriers in the family, two presymptomatic healthy mutation carriers, and four mutation carriers clinically symptomatic for AD. CSF samples were placed on ice, aliquoted and stored at –20° C. until tested.

A. Measurement of APP Levels

Total sAPP and α-sAPP levels in the CSF samples were quantitated using a sandwich enzyme-linked immunosorbent assay (ELISA) and immunoblotting followed by laser-scanning densitometry, respectively.

Standards used in the assays were obtained by isolation of total sAPP and α-sAPP from medium conditioned by human neuroblastoma IMR32 cells [ATCC Accession No. CCL127] or the HGB695 cells, described above in Example 31B, as follows. Conditioned medium was filtered to remove large cell debris, and sAPP was extracted by passing the media over an anion exchange column using Toyopearl DEAE 650C resin (Toso-Hass, Philadelphia, Pa.). The bound sAPP was eluted from the column using a linear gradient of 0 to 0.6 M NaCl in 50 mM sodium phosphate, pH 7.5. All sAPP-containing eluate fractions were pooled and loaded onto an immunoaffinity column containing a monoclonal antibody that specifically recognizes an amino-terminal epitope of human APP (for example, monoclonal antibody P2-1 raised against native human PN-2) [see, e.g., U.S. Pat. No. 5,213,962] linked to Toyopearl AF-Tresyl 650 M resin (Toso-Hass). Bound sAPP was eluted from the column with 0.1 M sodium citrate, pH 2.0. To separate α-sAPP from the other soluble forms of sAPP contained in total sAPP that do not contain at least the amino-terminal portion of Aβ, the total sAPP was loaded onto a Sepharose 4B immunoaffinity adsorption column containing a monoclonal antibody that recognizes an epitope within the first ~17 amino acids of Aβ (for example, monoclonal antibody 6E10). Specifically bound α-sAPP was eluted from the column with 0.1 M sodium citrate, pH 3.0. The solution pH of the purified sAPPs was adjusted to 7.2 and 1-ml aliquots were stored at –70° C.

B. Quantitation of Total sAPP

The ELISA used to quantitate total sAPP levels in CSF samples employed a monoclonal antibody, such as P2-1, discussed above, that specifically recognizes an amino-terminal epitope of human APP as the capture antibody. The capture antibody was attached to the wells of a 96-well microtiter plate by incubating the plate with the antibody (that had been diluted in PBS, pH 7.2) for 60 min at 37° C. The plates were then washed three times with 0.3 ml of 0.1% Tween-20 in PBS. The wells were also incubated with a solution of 0.5% casein in PBS (150 μl/well) for 30 min. at 37° C.

CSF samples (100 μl diluted 1:20) or sAPP standards (100 μl) containing a range of 5 to 50 ng/ml were added to the wells and allowed to incubate for 60 min at 37° C. Following incubation, the wells were washed thoroughly with 0.1% Tween-20 in PBS. A goat anti-human APP polyclonal antibody raised against immunopurified APP from medium conditioned by cultured IMR32 human neuroblastoma cells (American Type Culture Collection Accession No. 127) conjugated to horseradish peroxidase was used as the signal antibody. The antibody was diluted 1:500 in PBS and 10% normal goat serum, pH 7.2, containing 0.1% Tween-20, added to the wells, and incubated for 60 min at 37 ° C. Unbound antibody was removed by washing as described above. To detect the bound antibody, 0.1 ml of the chromogenic substrate K-Blue Solution (Elisa Technologies, Lexington Ky.) was added to the wells and allowed to incubate for 15 min at ambient temperature. Reactions were stopped by addition of 0.1 ml of a 9.8% solution of phosphoric acid. The optical density of the samples was measured by spectrophotometry at 450 nm. The concentration of sAPP peptides in the CSF sample was estimated from the standard curve. Samples were analyzed in duplicate.

Total sAPP levels were also measured using quantitative immunoblotting essentially as described below for measurement of α-sAPP, except using a monoclonal antibody raised against a recombinant APP-containing fusion protein (e.g., 22C11 available from Boehringer Mannheim, Indianapolis, Ind.) at a concentration of 0.3 μg/ml to specifically detect sAPP and using purified sAPP as a standard. Quantification of total sAPP by quantitative immunoblot gave a 95% correlation to quantification by ELISA.

C. Quantitation of α-sAPP

For immunoblot assays of α-sAPP contained in the CSF samples, 5–10 μl of sample and purified standard α-sAPP of known concentrations were analyzed by sodium dodecyl sulfate polyacrylamide gel electrophoresis (SDS-PAGE) under reducing conditions. Samples were diluted into Laemmli sample buffer and loaded onto 7.5% SDS-PAGE gel. After separation, the proteins were transferred to polyvinylidene difluoride membranes (PVDF Immobilon, Millipore, Bedford, Mass.) in CAPS transfer buffer (5 mM 3-[cyclohexylamine]-1-propanesulfonic acid, pH 11.0, 5% (v/v) methanol). Nonspecific binding of protein to membranes was blocked with PBS containing 5% (w/v) non-fat dried milk and then incubated for 1 hr with a monoclonal antibody (20 ml of 0.2 μg/ml) directed against the amino-terminus of Aβ (e.g., 6E10), and washed three times for one min each time in 20 ml of PBS and 0.1% Tween. Specifically bound antibody was detected using a biotinylated goat anti-mouse secondary antibody (Sigma) and a streptavidin-peroxidase conjugate (Amersham, Arlington Heights, Ill.) in combination with an enhanced chemiluminescence detection system (Amersham, Arlington Heights, Ill.). The blots were exposed to Kodak Scientific Imaging film X-OMAT AR and developed using a Kodak X-OMAT developer. Quantitation of the α-sAPP protein in the blots was performed by laser-scanning densitometry. Developed films within the linear range (or multiple exposures) were scanned at 50 μM pixel size using a densitometer (Molecular Dynamics, Sunnyvale, Calif.), and the data were quantified using the ImageQuaNT software system (Molecular Dynamics). Quantified volumes of α-sAPP standard were used to generate standard curves. From the standard curves, the levels of α-sAPP in ng/ml were determined.

D. Comparison of sAPP and α-sAPP Levels in CSF of Normal Subjects and Mutation Carriers Assays of sAPP and α-sAPP levels in CSF from normal subjects and Swedish mutation carriers were performed. Mann-Whitney non-parametric statistics were used for comparison of the data from the experimental groups. Correlations were investigated with Pearson's and Spearman's rank correlation coefficients. Significance levels were set at p<0.05. The CSF of diseased carriers had lower levels of α-sAPP than the CSF samples of non-carriers, with no overlap between the two groups (z=−2.72; p=0.007). The CSF obtained from the four AD subjects had lower levels of α-sAPP than that of the two pre-symptomatic AD carriers. There was a strong inverse correlation between α-sAPP concentration and age in the mutation carriers (R=0.94; p=0.005). In the mutation carriers, ~25% of the total sAPP in CSF was α-sAPP compared to 33% in CSF of non-carriers. This was a statistically significant difference.

The results indicate that α-sAPP and the ratio of α-sAPP to total sAPP in CSF are useful markers in the detection of neurodegenerative disorders characterized by cerebral deposition of amyloid (e.g., AD) and in monitoring the progression of such disease. Furthermore, this assay system can be used in monitoring therapeutic intervention of these diseases.

Since modifications will be apparent to those of skill in this art, it is intended that this invention be limited only by the scope of the appended claims.

We claim:

1. A method of modulating the processing of amyloid precursor protein (APP), comprising contacting a composition containing APP under conditions in which APP is processed with a compound of the formula:

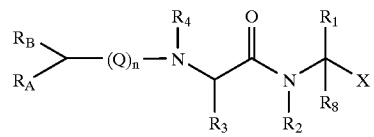

or a hydrate, isostere, stereoisomer or mixture thereof, or a pharmaceutically acceptable salt thereof, with the proviso that: (1) at least one of $R_1$ and $R_3$ is not a side chain of a naturally-occurring α-amino acid; and (2) when X is an aldehyde, $R_1$ cannot be the side chain of norleucine or norvaline, wherein:

$R_1$, $R_2$, $R_3$, $R_4$, $R_8$, $R_A$, $R_B$, X, Q and n are selected from among (i), (ii) or (iii) as follows:

(i) $R_1$, $R_3$ and $R_B$ are each independently selected from the group consisting of a side chain of a naturally occurring α-amino acid, H, alkyl, alkenyl, alkynyl, aryl, aralkyl, aralkenyl, aralkynyl, heteroaryl, heteroaralkyl, heteroaralkenyl, Y-substituted aryl, aralkyl, aralkenyl, aralkynyl, and Z-substituted heteroaryl, heteroaralkyl, heteroaralkenyl, in which Y is selected from the group consisting of halogen, lower alkyl, alkoxy, OH, haloalkyl, nitrile, S-alkyl, phenyl, and —NRR, R is H, alkyl, lower alkyl, OH or halo-lower alkyl, Z is lower alkyl or halo lower alkyl;

$R_2$, $R_4$ and $R_8$ are each independently selected from H and lower alkyl;

Q is selected from the group consisting of —C(O)—, —O—C(O)—, —S(O)$_2$— and —HN—C(O)—;

n is zero or one;

$R_A$ is —(T)$_m$—(D)$_m$—$R_1$ in which T is O or NH, and D is $C_{1-4}$ alkyl or $C_{2-4}$ alkene; and m is zero or one;

X is selected from the group consisting of —(CH$_2$)$_r$C(O)H, —(CH$_2$)$_r$C(O)haloalkyl, —(CH$_2$)$_r$C(O)(CH$_2$)$_r$CHN$_2$, —(CH$_2$)$_r$C≡N, —C(CH$_2$)$_r$(O)C(CH$_2$)$_r$(O)OR$_D$, —(CH$_2$)$_r$C(O)(CH$_2$)$_r$C(O)NR$_D$R$_D$, —(CH$_2$)$_r$CH(OH)(CH$_2$)$_r$C(O)U, —(CH$_2$)$_r$CH(OH)CH$_2$C(O)U, —(CH$_2$)$_r$C(O)W and —(CH$_2$)$_r$C(O)CH$_2$W, in which: $R_D$ is selected from H, alkyl, phenyl, benzyl and phenethyl; U is —OR$_D$ or —NR$_D$R$_D$, and W is —OR$_D$, —SR$_D$, —NR$_D$R$_D$, or a heterocyclic moiety, and r is 0–5; or (ii) $R_3$, $R_4$, $R_A$, $R_B$, Q, X and n are as defined in (i), $R_8$ is H; and $R_1$ and $R_2$ are each independently selected as follows:
(a) from lower alkyl, lower alkyl linked to a heteroatom, or a heteroatom, with the proviso when more than one heteroatom is present, there is at least one carbon atom between each heteroatom, and
(b) $R_1$ and $R_2$ are unsubstituted or substituted with Y, and
(c) together with the atoms to which they are attached form a 4–6 membered heterocyclic moiety; or (iii) $R_1$, $R_2$, $R_8$, X, Q and n are as defined in (i);

$R_3$ and $R_4$ are each independently selected as follows:
(a) from lower alkyl, lower alkyl linked to a heteroatom, or a heteroatom, with the proviso when more than one heteroatom is present, there is at least one carbon atom between each heteroatom, and
(b) $R_3$ and $R_4$ are unsubstituted or substituted with Y, and
(c) together with the atoms to which they are attached form a 4–6 membered heterocyclic moiety;

whereby:
(a) the formation of Aβ peptide is decreased, or
(b) the formation of α-sAPP is increased, relative to the amounts formed in the absence of the compound.

2. The method of claim 1, wherein at least one of $R_1$ and $R_3$ is $C_{2-6}$ alkenyl or $C_{2-6}$ alkynyl.

3. The method of claim 1, wherein at least one of $R_1$ and $R_3$ is $C_{2-6}$ alkenyl.

4. The method of claim 1, wherein at least one of $R_1$ and $R_3$ is 2-methylpropenyl or 2-butenyl.

5. The method of claim 1, wherein at least one of $R_1$ and $R_3$ is 2-methylpropenyl.

6. The method of claim 1, wherein $R_1$ is $C_{2-6}$ alkenyl.

7. The method of claim 1, wherein $R_1$ is 2-methylpropenyl or 2-butenyl.

8. The method of claim 1, wherein $R_1$ is 2-methylpropenyl.

9. The method of claim 1, wherein at least one of $R_1$ and $R_3$ is 2-methylpropenyl or 2-butenyl; and X is selected from the group consisting of aldehyde, α-ketoester and α-ketoamide.

10. The method of claim 1, wherein the compound is selected from the group consisting of (2SR)-N-[(2S)-2-benzoxy-4-methylpentanoyl]-L-Leu-[2-(4-methyl-4-pentenal)]amide and (2SR)-N-[(2R)-[2-(1'-phenyl-1'-propene)-4-methylpentanoyl]]-L-Leu-N-[2-(4-methyl-4-pentenal)]amide.

11. The method of claim 1, wherein the compound is a mixture of diastereomers of (2SR)-N-[(2S)-2-benzoxy-4-methylpentanoyl]-L-Leu-[2-(4-methyl-4-pentenal)]amide.

12. The method of claim 1, wherein the composition comprises a protease that processes APP.

13. The method of claim 12, wherein the protease is a cysteinyl protease.

14. The method of claim 1, whereby processing of APP results in a decrease in formation of amyloid β-protein compared to the amount formed in the absence of the compound.

15. The method of claim 1, whereby upon processing of the APP formation of a product designated α-sAPP is increased compared to the amount formed in the absence of the compound.

16. The method of claim 1, wherein the compound is (2S)-N-[(2S)-2-benzoxy-4-methylpentanoyl]-L-Leu-[2-(4-methyl-4-pentenal)]amide.

17. The method of claim 1, wherein the compound is (2R)-N-[(2S)-2-benzoxy-4-methylpentanoyl]-L-Leu-[2-(4-methyl-4-pentenal)]amide.

\* \* \* \* \*

UNITED STATES PATENT AND TRADEMARK OFFICE
CERTIFICATE OF CORRECTION

PATENT NO.: 5,962,419

DATED: Oct. 5, 1999

INVENTOR(S): McDonald et al.

It is certified that error appears in the above-identified patent and that said Letters Patent is hereby corrected as shown below:

IN THE TITLE PAGES:

In item [54], please replace "PEPTIDE AND PEPTIDE ANALOG PROTEASE INHIBITORS" with —METHODS OF TREATING NEURODEGENERATIVE DISORDERS USING PROTEASE INHIBITORS—;

In item [56] entitled References Cited, in the OTHER PUBLICATIONS, please add the following references:

—English Language Abstract of German Patent No. 4331134 A1, issued 03/16/1995 (Dialog(R)File 351:Derwent).

Nymox Corporation Internet Home Page, http://www.nymox.com/.

Nymox Corporation Press Releases, Feb. 13, 1997-Sept. 17, 1998, http://www.nymox.com/press.htm.—; and In *Attorney, Agent, or Firm*, please replace "Stephanine" with —Stephanie—.

IN THE SPECIFICATION:

at column 2, line 22, please delete "is";

Signed and Sealed this

Twenty-fifth Day of July, 2000

*Attest:*

Q. TODD DICKINSON

*Attesting Officer*    Director of Patents and Trademarks

UNITED STATES PATENT AND TRADEMARK OFFICE
CERTIFICATE OF CORRECTION

PATENT NO.: 5,962,419

DATED: Oct. 5, 1999

INVENTOR(S): McDonald et al.

It is certified that error appears in the above-identified patent and that said Letters Patent is hereby corrected as shown below:

at columns 29 and 30, line 65, please insert the following reaction scheme:

REACTION SCHEME K

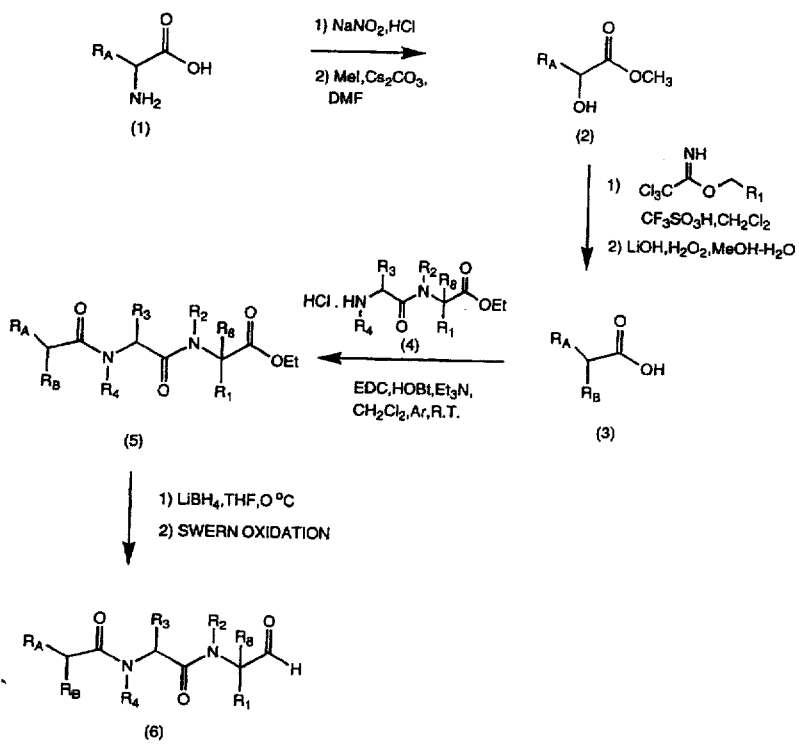

wherein the $R_1, R_2, R_3, R_4, R_8, R_A$ and $R_B$ are as defined above.

UNITED STATES PATENT AND TRADEMARK OFFICE
CERTIFICATE OF CORRECTION

PATENT NO.: 5,962,419

DATED: Oct. 5, 1999

INVENTOR(S): McDonald et al.

It is certified that error appears in the above-identified patent and that said Letters Patent is hereby corrected as shown below:

at column 48, line 3, please replace "provence" with —province—;

at column 50, line 17, please insert —as— between "such" and "cysteine";

at column 54, line 27, please replace "Precusor" with —Precursor—; and at column 56, line 67, please replace "addition" with —additional—.